US011882815B2

(12) United States Patent
Rivera-Perez et al.

(10) Patent No.: US 11,882,815 B2
(45) Date of Patent: Jan. 30, 2024

(54) RECOMBINANT ADENO-ASSOCIATED VIRUSES FOR DELIVERING GENE EDITING MOLECULES TO EMBRYONIC CELLS

(71) Applicant: University of Massachusetts, Boston, MA (US)

(72) Inventors: Jaime Antonio Rivera-Perez, Shrewsbury, MA (US); Guangping Gao, Westborough, MA (US)

(73) Assignee: University of Massachusetts, Boston, MA (US)

( * ) Notice: Subject to any disclaimer, the term of this patent is extended or adjusted under 35 U.S.C. 154(b) by 1181 days.

(21) Appl. No.: 16/310,381

(22) PCT Filed: Jun. 15, 2017

(86) PCT No.: PCT/US2017/037796
§ 371 (c)(1),
(2) Date: Dec. 14, 2018

(87) PCT Pub. No.: WO2017/218852
PCT Pub. Date: Dec. 21, 2017

(65) Prior Publication Data
US 2019/0141968 A1   May 16, 2019

Related U.S. Application Data

(60) Provisional application No. 62/350,358, filed on Jun. 15, 2016.

(51) Int. Cl.
*A01K 67/027* (2006.01)
*C12N 15/864* (2006.01)
*C12N 5/073* (2010.01)
*C12N 15/85* (2006.01)
*C12N 9/22* (2006.01)

(52) U.S. Cl.
CPC ........ *A01K 67/0275* (2013.01); *C12N 5/0604* (2013.01); *C12N 9/22* (2013.01); *C12N 15/8509* (2013.01); *C12N 15/8645* (2013.01); *A01K 2217/075* (2013.01); *C12N 2015/8527* (2013.01); *C12N 2750/14143* (2013.01)

(58) Field of Classification Search
CPC .......... A01K 67/0275; A01K 2217/075; C12N 5/0604; C12N 9/22; C12N 15/8509; C12N 15/8654; C12N 2015/8527; C12N 2750/14143
USPC .................. 435/455, 456; 800/13; 514/44 R
See application file for complete search history.

(56) References Cited

U.S. PATENT DOCUMENTS

| | | |
|---|---|---|
| 5,478,745 A | 12/1995 | Samulski et al. |
| 5,871,982 A | 2/1999 | Wilson et al. |
| 6,156,303 A | 12/2000 | Russell et al. |
| 6,177,403 B1 | 1/2001 | Stedman |
| 6,251,677 B1 | 6/2001 | Wilson et al. |
| 6,485,966 B2 | 11/2002 | Gao et al. |
| 6,498,244 B1 | 12/2002 | Patel et al. |
| 6,544,786 B1 | 4/2003 | Xiao et al. |
| 6,953,690 B1 | 10/2005 | Gao et al. |
| 6,962,815 B2 | 11/2005 | Bartlett |
| 7,022,519 B2 | 4/2006 | Gao et al. |
| 7,198,951 B2 | 4/2007 | Gao et al. |
| 7,235,393 B2 | 6/2007 | Gao et al. |
| 7,282,199 B2 | 10/2007 | Gao et al. |
| 7,427,396 B2 | 9/2008 | Arbetman et al. |
| 7,456,015 B2 | 11/2008 | Bohn et al. |
| 7,906,111 B2 | 3/2011 | Wilson et al. |
| 8,222,221 B2 | 7/2012 | Corey et al. |
| 8,524,446 B2 | 9/2013 | Gao et al. |
| 8,734,809 B2 | 5/2014 | Gao et al. |
| 9,249,424 B2 | 2/2016 | Wolf et al. |
| 9,701,984 B2 | 7/2017 | Gao et al. |
| 2001/0016355 A1 | 8/2001 | Samulski et al. |
| 2002/0164783 A1 | 11/2002 | Feldhaus |
| 2002/0192823 A1 | 12/2002 | Bartlett |
| 2003/0103939 A1 | 6/2003 | Engelhardt et al. |
| 2003/0110526 A1 | 6/2003 | Brown et al. |
| 2003/0138772 A1 | 7/2003 | Gao et al. |
| 2003/0228282 A1 | 12/2003 | Gao et al. |
| 2004/0101514 A1 | 5/2004 | Liu et al. |
| 2005/0014262 A1 | 1/2005 | Gao et al. |
| 2005/0197313 A1 | 9/2005 | Roelvink |
| 2005/0255086 A1 | 11/2005 | Davidson et al. |
| 2005/0255089 A1 | 11/2005 | Chiorini et al. |
| 2005/0287122 A1 | 12/2005 | Bartlett et al. |
| 2006/0018841 A1 | 1/2006 | Arbetman et al. |

(Continued)

FOREIGN PATENT DOCUMENTS

| | | |
|---|---|---|
| EP | 2261242 A1 | 12/2010 |
| EP | 2468891 A2 | 6/2012 |

(Continued)

OTHER PUBLICATIONS

Ahmed et al. (2014) BMC Neuroscience, vol. 5(4), http://www.biomedcentral.com/1471-2202/5/4, pp. 1-11.*
Grimm et al. (1998) Human Gene Therapy, vol. 9, 2745-2760.*
Wu et al. (2013) Cell Stem Cell, vol. 13, 659-662.*
Tabebordbar et al. (Jan. 22, 2016) Science, vol. 351 (6271) 407-411, and Supplemental materials.*
Rutledge et al. (1998) J. Virol., vol. 72(1), 309-319.*
Sternberg et al. (1986) JBC, vol. 187(2), 197-212.*
Keiser et al. (2001) Cloning, vol. 3(1), 23-30.*
Sato et al. (2016) Biology Direct, vol. 11(16), doi:10.1186/s13062-016-0115-8, pp. 1-12.*

(Continued)

*Primary Examiner* — Anne Marie S Wehbe
(74) *Attorney, Agent, or Firm* — Wolf, Greenfield & Sacks, P.C.

(57) ABSTRACT

The disclosure, in some aspects, relates to methods and compositions for recombinant adeno-associated virus (rAAV)-mediated delivery of genome editing molecules to a pre-implantation embryo.

11 Claims, 33 Drawing Sheets

Specification includes a Sequence Listing.

(56) References Cited

U.S. PATENT DOCUMENTS

| | | |
|---|---|---|
| 2006/0063174 A1 | 3/2006 | Turner et al. |
| 2006/0093589 A1 | 5/2006 | Warrington et al. |
| 2006/0153826 A1 | 7/2006 | Arnould et al. |
| 2006/0189564 A1 | 8/2006 | Burright et al. |
| 2006/0228800 A1 | 10/2006 | Lin et al. |
| 2006/0292117 A1 | 12/2006 | Loiler et al. |
| 2007/0036760 A1 | 2/2007 | Wilson et al. |
| 2007/0243526 A1 | 10/2007 | Kay et al. |
| 2008/0075737 A1 | 3/2008 | Gao et al. |
| 2008/0292595 A1 | 11/2008 | Arbetman et al. |
| 2009/0042828 A1 | 2/2009 | Xu et al. |
| 2009/0111766 A1 | 4/2009 | Atkinson et al. |
| 2009/0149409 A1 | 6/2009 | Bohn et al. |
| 2009/0197338 A1 | 8/2009 | Vandenberghe et al. |
| 2009/0215879 A1 | 8/2009 | DiPrimio et al. |
| 2010/0104561 A1 | 4/2010 | Zhong et al. |
| 2010/0323001 A1 | 12/2010 | Pachuk |
| 2011/0171262 A1 | 7/2011 | Bakker et al. |
| 2011/0172293 A1 | 7/2011 | Fish et al. |
| 2011/0212520 A1 | 9/2011 | Davidson et al. |
| 2011/0258716 A1 | 10/2011 | Baltimore et al. |
| 2012/0077870 A1 | 3/2012 | Blanks et al. |
| 2012/0137379 A1 | 5/2012 | Gao et al. |
| 2012/0270930 A1 | 10/2012 | Van Der Maarel et al. |
| 2012/0309050 A1 | 12/2012 | Kumon et al. |
| 2013/0030042 A1 | 1/2013 | Couto |
| 2013/0101558 A1 | 4/2013 | Gao et al. |
| 2013/0109742 A1 | 5/2013 | Hewitt et al. |
| 2013/0142861 A1 | 6/2013 | Tsou et al. |
| 2013/0195801 A1 | 8/2013 | Gao et al. |
| 2013/0323226 A1 | 12/2013 | Wilson et al. |
| 2014/0142161 A1 | 5/2014 | Flotte et al. |
| 2014/0142288 A1 | 5/2014 | Davidson et al. |
| 2014/0147418 A1 | 5/2014 | Chiorini et al. |
| 2014/0179770 A1 | 6/2014 | Zhang et al. |
| 2014/0201857 A1 | 7/2014 | Fahrenkrug et al. |
| 2014/0335054 A1 | 11/2014 | Gao et al. |
| 2014/0359799 A1* | 12/2014 | Wang ............ C12N 15/8509 435/456 |
| 2015/0065560 A1 | 3/2015 | Bjorklund et al. |
| 2015/0258180 A1 | 9/2015 | Mahuran et al. |
| 2016/0017005 A1 | 1/2016 | Asokan et al. |
| 2016/0060624 A1 | 3/2016 | Davidson et al. |
| 2016/0076054 A1 | 3/2016 | Auricchio et al. |
| 2016/0153005 A1 | 6/2016 | Zhang et al. |
| 2016/0185832 A1 | 6/2016 | Drivas et al. |
| 2016/0194374 A1 | 7/2016 | Wijnholds et al. |
| 2016/0272976 A1 | 9/2016 | Kaspar |
| 2016/0340661 A1* | 11/2016 | Cong ............... A61K 48/005 |
| 2017/0029785 A1 | 2/2017 | Zhao et al. |
| 2017/0114340 A1 | 4/2017 | Mueller et al. |
| 2017/0165377 A1 | 6/2017 | Gao et al. |

FOREIGN PATENT DOCUMENTS

| | | |
|---|---|---|
| JP | 2008-538286 | 10/2008 |
| WO | WO 2003/042397 | 5/2003 |
| WO | WO 2004/108922 A2 | 12/2004 |
| WO | WO 2005/033321 | 4/2005 |
| WO | WO 2006/031267 A2 | 3/2006 |
| WO | WO 2006/066066 A2 | 6/2006 |
| WO | WO 2006/119432 A2 | 11/2006 |
| WO | WO 2008/125846 A2 | 10/2008 |
| WO | WO 2008/150897 A2 | 12/2008 |
| WO | WO 2009/043936 | 4/2009 |
| WO | WO 2009/146178 A1 | 12/2009 |
| WO | WO 2010/027446 A2 | 3/2010 |
| WO | WO 2010/071454 A1 | 6/2010 |
| WO | WO 2010/099383 A2 | 9/2010 |
| WO | WO 2010/129021 A1 | 11/2010 |
| WO | WO 2010/138263 A2 | 12/2010 |
| WO | WO 2011/094198 A1 | 8/2011 |
| WO | WO 2012/123430 A1 | 9/2012 |
| WO | WO 2013/055865 A1 | 4/2013 |
| WO | WO 2013/123503 A1 | 8/2013 |
| WO | WO 2013/170078 A1 | 11/2013 |
| WO | WO 2013/190059 A1 | 11/2013 |
| WO | WO 2014/160092 A1 | 10/2014 |
| WO | WO 2014/186746 A1 | 11/2014 |
| WO | WO 2014/197748 A2 | 11/2014 |
| WO | WO 2015/121501 A1 | 8/2015 |
| WO | WO 2015/164786 | 10/2015 |
| WO | WO 2015/168666 A2 | 11/2015 |
| WO | WO 2016/065001 A1 | 4/2016 |
| WO | WO 2017/023724 A1 | 2/2017 |

OTHER PUBLICATIONS

Takahashi et al. (2015) Scientific Reports, vol. 5:11406, doi:10.1038/srep11406, p. 1-11.*

Adachi et al., Drawing a high-resolution functional map of adeno-associated virus capsid by massively parallel sequencing. Nat Commun. 2014;5:3075. doi: 10.1038/ncomms4075.

Afione et al., In vivo model of adeno-associated virus vector persistence and rescue. J Virol. May 1996;70(5):3235-41.

Ahmed et al., A Single Intravenous rAAV Injection as Late as P20 Achieves Efficacious and Sustained CNS Gene Therapy in Canavan Mice. Mol Ther. Jul. 2, 2013. doi: 10.1038/mt.2013.138. [Epub ahead of print].

Akache et al., The 37/67-kilodalton laminin receptor is a receptor for adeno-associated virus serotypes 8, 2, 3, and 9. J Virol. Oct. 2006;80(19):9831-6.

Arbetman et al., Novel caprine adeno-associated virus (AAV) capsid (AAV-Go.1) is closely related to the primate AAV-5 and has unique tropism and neutralization properties. J Virol. Dec. 2005;79(24):15238-45.

Arbuthnot et al., Hepatic delivery of RNA interference activators for therapeutic application. Curr Gene Ther. Apr. 2009;9(2):91-103.

Asokan et al., The AAV vector toolkit: poised at the clinical crossroads. Mol Ther. Apr. 2012;20(4):699-708. doi: 10.1038/mt.2011.287. Epub Jan. 24, 2012.

Baek et al., AAV-mediated gene delivery in adult GM1-gangliosidosis mice corrects lysosomal storage in CNS and improves survival. PLoS One. Oct. 18, 2010;5(10):e13468. doi: 10.1371/journal.pone.0013468.

Bals et al., Transduction of well-differentiated airway epithelium by recombinant adeno-associated virus is limited by vector entry. J Virol. Jul. 1999;73(7):6085-8.

Berns et al., Biology of adeno-associated virus. Curr Top Microbiol Immunol. 1996;218:1-23.

Berns et al., Detection of adeno-associated virus (AAV)-specific nucleotide sequences in DNA isolated from latently infected Detroit 6 cells. Virology. Dec. 1975;68(2):556-60.

Beutler et al., AAV for pain: steps towards clinical translation. Gene Ther. Apr. 2009;16(4):461-9. Epub Mar. 5, 2009.

Bish et al., Adeno-associated virus (AAV) serotype 9 provides global cardiac gene transfer superior to AAV1, AAV6, AAV7, and AAV8 in the mouse and rat. Hum Gene Ther. Dec. 2008;19(12):1359-68. doi: 10.1089/hum.2008.123.

Borel et al., Recombinant AAV as a platform for translating the therapeutic potential of RNA interference. Mol Ther. Apr. 2014;22(4):692-701. doi:10.1038/mt.2013.285. Epub Dec. 19, 2013.

Bourdenx et al., Systemic gene delivery to the central nervous system using Adeno-associated virus. Front Mol Neurosci. Jun. 2, 2014;7:50. doi: 10.3389/fnmol.2014.00050. eCollection 2014.

Brantly et al., Phase I trial of intramuscular injection of a recombinant adeno-associated virus serotype 2 alphal-antitrypsin (AAT) vector in AAT-deficient adults. Hum Gene Ther. Dec. 2006;17(12):1177-86.

Buning et al., Receptor targeting of adeno-associated virus vectors. Gene Ther. Jul. 2003;10(14):1142-51.

Calcedo et al., Worldwide epidemiology of neutralizing antibodies to adeno-associated viruses. J Infect Dis. Feb. 1, 2009;199(3):381-90.

Carter et al., Adeno-associated virus gene expression and regulation. CRC Handbook of parvoviruses. 1990:227-54.

(56) References Cited

OTHER PUBLICATIONS

Carter, in "Handbook of Parvoviruses", ed., P. Tijsser, CRC Press, pp. 155-168 (1990).
Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.
Cearley et al., Transduction characteristics of adeno-associated virus vectors expressing cap serotypes 7, 8, 9, and Rh10 in the mouse brain. Mol Ther. Mar. 2006;13(3):528-37. Epub Jan. 18, 2006.
Chadderton et al., Improved retinal function in a mouse model of dominant retinitis pigmentosa following AAV-delivered gene therapy. Mol Ther. Apr. 2009;17(4):593-9. Epub Jan. 27, 2009.
Chen et al., Comparative study of anti-hepatitis B virus RNA interference by double-stranded adeno-associated virus serotypes 7, 8, and 9. Mol Ther. Feb. 2009;17(2):352-9. Epub Dec. 9, 2008.
Chen et al., Efficient transduction of vascular endothelial cells with recombinant adeno-associated virus serotype 1 and 5 vectors. Hum Gene Ther. Feb. 2005;16(2):235-47.
Chen et al., Molecular signatures of disease brain endothelia provide new sites for CNS-directed enzyme therapy. Nat Med. Oct. 2009;15(10):1215-8. doi: 10.1038/nm.2025. Epub Sep. 13, 2009.
Cheng et al., Development of optimized AAV3 serotype vectors: mechanism of high-efficiency transduction of human liver cancer cells. Gene Ther. Apr. 2012;19(4):375-84. doi: 10.1038/gt.2011.105. Epub Jul. 21, 2011.
Chiorini et al., Cloning and characterization of adeno-associated virus type 5. J Virol. Feb. 1999;73(2):1309-19.
Chirmule et al., Humoral immunity to adeno-associated virus type 2 vectors following administration to murine and nonhuman primate muscle. J Virol. Mar. 2000;74(5):2420-5.
Choudhury et al., Identification of Novel vectors capable of CNS transduction in adult mice after single round selection using DNA shuffled AAV capsid library. Mol Ther. May 1, 2013;21(1):S1/.
Cideciyan et al., Human RPE65 gene therapy for Leber congenital amaurosis: persistence of early visual improvements and safety at 1 year. Hum Gene Ther. Sep. 2009;20(9):999-1004.
Conlon et al., Efficient hepatic delivery and expression from a recombinant adeno-associated virus 8 pseudotyped alpha1-antitrypsin vector. Mol Ther. Nov. 2005;12(5):867-75. Epub Aug. 8, 2005.
Conlon et al., Ribozyme Approaches towards Down-Regulation of Pi*Z Mutant Human a-1 Anti-Trypsin. Mol. Therapy. 2004;9:S333. Abstract 875.
Conrad et al., Safety of single-dose administration of an adeno-associated virus (AAV)-CFTR vector in the primate lung. Gene Ther. Aug. 1996;3(8):658-68.
Cruz et al., In vivo post-transcriptional gene silencing of alpha-1 antitrypsin by adeno-associated virus vectors expressing siRNA. Lab Invest. Sep. 2007;87(9):893-902. Epub Jun. 25, 2007.
Cruz et al., The promise of gene therapy for the treatment of alpha-1 antitrypsin deficiency. Pharmacogenomics. Sep. 2007;8(9):1191-8.
Davidoff et al., Sex significantly influences transduction of murine liver by recombinant adeno-associated viral vectors through an androgen-dependent pathway. Blood. Jul. 15, 2003;102(2):480-8. Epub Mar. 13, 2003.
Davidson et al., Recombinant adeno-associated virus type 2, 4, and 5 vectors: transduction of variant cell types and regions in the mammalian central nervous system. Proc Natl Acad Sci U S A. Mar. 28, 2000;97(7):3428-32.
Daya et al., Gene therapy using adeno-associated virus vectors. Clin Microbiol Rev. Oct. 2008;21(4):583-93. doi: 10.1128/CMR.00008-08.
Duque et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.
Ehlert et al., Cellular toxicity following application of adeno-associated viral vector-mediated RNA interference in the nervous system. BMC Neurosci. Feb. 18, 2010;11:20.

Fechner et al., Cardiac-targeted RNA interference mediated by an AAV9 vector improves cardiac function in coxsackievirus B3 cardiomyopathy. J Mol Med (Berl). Sep. 2008;86(9):987-97. doi: 10.1007/s00109-008-0363-x. Epub Jun. 12, 2008.
Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.
Fischer et al., Successful transgene expression with serial doses of aerosolized rAAV2 vectors in rhesus macaques. Mol Ther. Dec. 2003;8(6):918-26.
Fisher et al., Transduction with recombinant adeno-associated virus for gene therapy is limited by leading-strand synthesis. J Virol. Jan. 1996;70(1):520-32.
Flotte et al., Gene therapy for alpha-1 antitrypsin deficiency. Hum Mol Genet. Apr. 15, 2011;20(R1):R87-92. doi: 10.1093/hmg/ddr156. Epub Apr. 16, 2011.
Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.
Flotte, Recombinant adeno-associated virus (AAV) gene therapy vectors for, cystic fibrosis (CF), alpha-1-antitrypsin deficiency (AAT) and fatty oxidation disorders (FAO). Umass Medical School. Interdisciplinary Graduate Program. Last accessed at http://www.umassmed.edu/igp/faculty/flotte.cfm?start=0& on Aug. 27, 2009.
Foust et al., Intravascular AAV9 preferentially targets neonatal-neurons and adult-astrocytes. Nature Biotechnology, 27; 59-65 2009.
Foust et al., Over the barrier and through the blood: to CNS delivery we go. Cell Cycle. Dec. 15, 2009;8(24):4017-8.
Fraldi et al., Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.
Fu et al., Self-complementary adeno-associated virus serotype 2 vector: global distribution and broad dispersion of AAV-mediated transgene expression in mouse brain. Mol Ther. Dec. 2003;8(6):911-7.
Gadalla et al., Improved survival and reduced phenotypic severity following AAV9/MECP2 gene transfer to neonatal and juvenile male Mecp2 knockout mice. Mol Ther. Jan. 2013;21(1):18-30. doi:10.1038/mt.2012.200. Epub Sep. 25, 2012.
Gao et al., Adeno-associated viruses undergo substantial evolution in primates during natural infections. Proc Natl Acad Sci U S A. May 13, 2003;100(10):6081-6. Epub Apr. 25, 2003.
Gao et al., Adeno-associated virus-mediated gene transfer to non-human primate liver can elicit destructive transgene-specific T cell responses. Hum Gene Ther. Sep. 2009;20(9):930-42. doi: 10.1089/hum.2009.060.
Gao et al., Biology of AAV serotype vectors in liver-directed gene transfer to nonhuman primates. Mol Ther. Jan. 2006;13(1):77-87. Epub Oct. 10, 2005.
Gao et al., Clades of Adeno-associated viruses are widely disseminated in human tissues. J Virol. Jun. 2004; 78(12):6381-8.
Gao et al., Erythropoietin gene therapy leads to autoimmune anemia in macaques. Blood. May 1, 2004;103(9):3300-2. Epub Dec. 24, 2003.
Gao et al., Inadvertent gene transfer of co-packaged rep and cap sequences during the production of AAV vector and its potential impact on vector performance. Molecular Therapy. May 2008;16(Suppl. 1):S105-S106. Abstract 279.
Gao et al., New recombinant serotypes of AAV vectors. Curr Gene Ther. Jun. 2005;5(3):285-97.
Gao et al., Novel adeno-associated viruses from rhesus monkeys as vectors for human gene therapy. Proc Natl Acad Sci U S A. Sep. 3, 2002;99(18):11854-9. Epub Aug. 21, 2002.
Gao et al., RAAV-mediated targeting in adult mice and its potential in generating animal models of tissue-specific somatic transgenics or knock down. Molecular Therapy. May 2008;16(1):S118-S119. Abstract 316.
GENBANK Submission; Accession No. ADZ26851; Wilson et al.; Jun. 30, 2005.

(56) References Cited

OTHER PUBLICATIONS

GENBANK Submission; Accession No. AF028705.1; Rutledge et al.; Jan. 12, 1998.
GENBANK Submission; NCBI, Accession No. AAB95450; Rutledge et al.; Jan. 12, 1998.
GENBANK Submission; NCBI, Accession No. AAS99264; Gao et al.; Jun. 24, 2004.
GENBANK Submission; NCBI, Accession No. ABA71701; Schmidt et al.; May 10, 2006.
GENBANK Submission; NCBI, Accession No. ACB55301; Vandenberghe et al.; Jul. 31, 2008.
GENBANK Submission; NCBI, Accession No. ACB55310; Vandenberghe et al.; Jul. 31, 2008.
GENBANK Submission; NCBI, Accession No. AY530579.10; 2004.
GENBANK Submission; NCBI, Accession No. NP_049542; Xiao et al.; Mar. 11, 2010.
GENBANK Submission; NCBI, Accession No. YP_680426; Ruffing et al.; Nov. 19, 2010.
Grimm et al., Fatality in mice due to oversaturation of cellular microRNA/short hairpin RNA pathways. Nature. May 25, 2006;441(7092):537-41.
Grimm, Small silencing RNAs: state-of-the-art. Adv Drug Deliv Rev. Jul. 25, 2009;61(9):672-703. doi: 10.1016/j.addr.2009.05.002. Epub May 7, 2009.
Hauswirth et al., Treatment of leber congenital amaurosis due to RPE65 mutations by ocular subretinal injection of adeno-associated virus gene vector: short-term results of a phase I trial. Hum Gene Ther. Oct. 2008;19(10):979-90.
Hernandez et al., Latent adeno-associated virus infection elicits humoral but not cell-mediated immune responses in a nonhuman primate model. J Virol. Oct. 1999;73(10):8549-58.
Hildinger et al., Hybrid vectors based on adeno-associated virus serotypes 2 and 5 for muscle-directed gene transfer. J Virol. Jul. 2001;75(13):6199-203.
Iida et al., Systemic Delivery of Tyrosine-Mutant AAV Vectors Results in Robust Transduction of Neurons in Adult Mice. BioMed Res Int. 2013;2013.
Iwamoto et al., Global diffuse distribution in the brain and efficient gene delivery to the dorsal root ganglia by intrathecal injection of adeno-associated viral vector serotype 1. J Gene Med. Jun. 2009;11(6):498-505. doi: 10.1002/jgm.1325.
Jakobsson et al., Lentiviral vectors for use in the central nervous system. Mol Ther. Mar. 2006;13(3):484-93. Epub Jan. 3, 2006.
Janson et al., Clinical protocol. Gene therapy of Canavan disease: AAV-2 vector for neurosurgical delivery of aspartoacylase gene (ASPA) to the human brain. Hum Gene Ther. Jul. 20, 2002;13(11):1391-412.
Koornneef et al., Apolipoprotein B knockdown by AAV-delivered shRNA lowers plasma cholesterol in mice. Mol Ther. Apr. 2011;19(4):731-40. doi:10.1038/mt.2011.6. Epub Feb. 8, 2011.
Kota et al., AAV8-Mediated Delivery of miR-26a inhibits cancer cell proliferation and induces tumor-specific apoptosis in a liver cancer model. Mol. Therapy. May 2009. 17(1):S300. Abstract 783.
Kotin et al., Organization of adeno-associated virus DNA in latently infected Detroit 6 cells. Virology. Jun. 1989;170(2):460-7.
Kotin et al., Site-specific integration by adeno-associated virus. Proc Natl Acad Sci U S A. Mar. 1990;87(6):2211-5.
Lawlor et al., Efficient gene delivery and selective transduction of glial cells in the mammalian brain by AAV serotypes isolated from nonhuman primates. Mol Ther. Oct. 2009; 17(10):1692-702. doi: 10.1038/mt.2009.170.
Lebherz et al., Gene therapy with novel adeno-associated virus vectors substantially diminishes atherosclerosis in a murine model of familial hypercholesterolemia. J Gene Med. Jun. 2004;6(6):663-72.
Leone et al., Aspartoacylase gene transfer to the mammalian central nervous system with therapeutic implications for Canavan disease. Ann Neurol. Jul. 2000;48(1):27-38. Erratum in: Ann Neurol Sep. 2000;48(3):398. Bilianuk L [corrected to Bilaniuk L].
Li et al., Efficient and Targeted Transduction of Nonhuman Primate Liver With Systemically Delivered Optimized AAV3B Vectors. Mol Ther. Dec. 2015;23(12):1867-76. doi: 10.1038/mt.2015.174. Epub Sep. 25, 2015.
Li et al., Ex vivo transduction and transplantation of bone marrow cells for liver gene delivery of alpha1-antitrypsin. Mol Ther. Aug. 2010; 18(8):1553-8. Epub Jun. 15, 2010.
Li et al., Protein trans-splicing as a means for viral vector-mediated in vivo gene therapy. Hum Gene Ther. Sep. 2008; 19(9):958-64. doi: 10.1089/hum.2008.009.
Lin et al., Impact of preexisting vector immunity on the efficacy of adeno-associated virus-based HIV-1 Gag vaccines. Hum Gene Ther. Jul. 2008;19(7):663-9.
Liu et al., Biological Differences in rAAV Transduction of Airway Epithelia in Humans and in Old World Non-human Primates. Mol Ther. Dec. 2007;15(12):2114-23. Epub Jul. 31, 2007.
Liu et al., Comparative biology of rAAV transduction in ferret, pig and human airway epithelia. Gene Ther. Nov. 2007;14(21):1543-8. Epub Aug. 30, 2007.
Liu et al., Species-specific differences in mouse and human airway epithelial biology of recombinant adeno-associated virus transduction. Am J Respir Cell Mol Biol. Jan. 2006;34(1):56-64. Epub Sep. 29, 2005.
Loiler et al., Targeting recombinant adeno-associated virus vectors to enhance gene transfer to pancreatic islets and liver. Gene Ther. Sep. 2003;10(18):1551-8.
Lowenstein, Crossing the rubicon. Nat Biotechnol. Jan. 2009;27(1):42-4.
Lux et al., Green fluorescent protein-tagged adeno-associated virus particles allow the study of cytosolic and nuclear trafficking. J Virol. Sep. 2005;79(18):11776-87.
Ma et al., Therapeutic silencing of miR-10b inhibits metastasis in a mouse mammary tumor model. Nat Biotechnol. Apr. 2010;28(4):341-7. doi: 10.1038/nbt.1618. Epub Mar. 28, 2010.
Maguire et al., Directed evolution of adeno-associated virus for glioma cell transduction. J Neurooncol. Feb. 2010;96(3):337-47. doi: 10.1007/s11060-009-9972-7. Epub Jul. 19, 2009.
Maguire et al., Gene therapy for the nervous system: challenges and new strategies. Neurotherapeutics. Oct. 2014;11(4):817-39. doi: 10.1007/s13311-014-0299-5.
Manfredsson et al., AAV9: a potential blood-brain barrier buster. Mol Ther. Mar. 2009;17(3):403-5.
Manno et al., Successful transduction of liver in hemophilia by AAV-Factor IX and limitations imposed by the host immune response. Nat Med. Mar. 2006;12(3):342-7. Epub Feb. 12, 2006. Erratum in: Nat Med. May 2006;12(5):592. Rasko, John [corrected to Rasko, John JE]; Rustagi, Pradip K [added].
Matalon et al., Adeno-associated virus-mediated aspartoacylase gene transfer to the brain of knockout mouse for canavan disease. Mol Ther. May 2003;7(5 Pt 1):580-7.
McCarty et al., Adeno-associated virus terminal repeat (TR) mutant generates self- complementary vectors to overcome the rate-limiting step to transduction in vivo. Gene Ther. Dec. 2003;10(26):2112-8.
McCarty et al., Integration of adeno-associated virus (AAV) and recombinant AAV vectors. Annu Rev Genet. 2004;38:819-45.
McCarty et al., Self-complementary recombinant adeno-associated virus (scAAV) vectors promote efficient transduction independently of DNA synthesis. Gene Ther. Aug. 2001;8(16):1248-54.
McCarty, Self-complementary AAV vectors; advances and applications. Mol Ther. Oct. 2008;16(10):1648-56. Epub Aug. 5, 2008.
McCurdy et al., Sustained normalization of neurological disease after intracranial gene therapy in a feline model. Sci Transl Med. Apr. 9, 2014;6(231):231ra48. doi: 10.1126/scitranslmed.3007733.
Meijer et al., Controlling brain tumor growth by intraventricular administration of an AAV vector encoding IFN-beta. Cancer Gene Ther. Aug. 2009;16(8):664-71. doi: 10.1038/cgt.2009.8. Epub Feb. 6, 2009.
Mietzsch et al., OneBac 2.0: Sf9 Cell Lines for Production of AAV5 Vectors with Enhanced Infectivity and Minimal Encapsidation of Foreign DNA. Hum Gene Ther. Oct. 2015;26(10):688-97. doi:10.1089/hum.2015.050. Epub Aug. 6, 2015.

(56) References Cited

OTHER PUBLICATIONS

Mingozzi et al., CD8(+) T-cell responses to adeno-associated virus capsid in humans. Nat Med. Apr. 2007;13(4):419-22. Epub Mar. 18, 2007.
Moss et al., Repeated adeno-associated virus serotype 2 aerosol-mediated cystic fibrosis transmembrane regulator gene transfer to the lungs of patients with cystic fibrosis: a multicenter, double-blind, placebo-controlled trial. Chest. Feb. 2004;125(2):509-21.
Mueller et al., Development of Simultaneous Gene Augmentation and Reduction of Mutant Gene Expression with a Single Recombinant AAV for Alpha-1 Antitrypsin Disease. Molecular Therapy May 2009; 17(1):S391-S392. Abstract 1030.
Mueller et al., In Vivo AAV Delivered Allele Specific shRNA for the Knockdown of Alpha-1 Antitrypsin. Molecular Therapy May 2010;18(1):S22. Abstract 53.
Mueller et al., In Vivo Allele Specific Knockdown of Mutant Alpha-1 Antitrypsin Using Recombinant AAV Delivered shRNA. Molecular Therapy May 2009;17(1):S313. Abstract 817.
Mueller et al., Sustained miRNA-mediated knockdown of mutant AAT with simultaneous augmentation of wild-type AAT has minimal effect on global liver miRNA profiles. Mol Ther. Mar. 2012;20(3):590-600. Epub Jan. 17, 2012.
Mueller et al., The pros and cons of immunomodulatory IL-10 gene therapy with recombinant AAV in a Cftr-/- -dependent allergy mouse model. Gene Ther. Feb. 2009;16(2):172-83. Epub Sep. 25, 2008.
Mueller et al., Using rAAV Delivered miRNAs to Knockdown Misfolded Human Alpha 1 Antitrypsin in a Transgenic Mouse Model. Molecular Therapy May 2010;18(1):S21. Abstract 51.
NCBI BLAST Protein Sequence. RID-09JSKF33114. Alignment of Seq ID Nos. 87, 179. 2016.
O'Reilly et al., RNA interference-mediated suppression and replacement of human rhodopsin in vivo. Am J Hum Genet. Jul. 2007;81(1):127-35. Epub May 23, 2007.
Passini et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.
Pertin et al., Efficacy and specificity of recombinant adeno-associated virus serotype 6 mediated gene transfer to drg neurons through different routes of delivery. Poster sessions. Eur J. Pain. 2009;13:S74. Abstract 229.
Pfeifer et al., Pharmacological potential of RNAi—focus on miRNA. Pharmacol Ther. Jun. 2010;126(3):217-27. doi: 10.1016/j.pharmthera.2010.03.006. Epub Apr. 11, 2010.
Scallan et al., Human immunoglobulin inhibits liver transduction by AAV vectors at low AAV2 neutralizing titers in SCID mice. Blood. Mar. 1, 2006;107(5):1810-7. Epub Oct. 25, 2005.
Schattgen et al., Cutting Edge: DNA in the Lung Microenvironment during Influenza Virus Infection Tempers Inflammation by Engaging the DNA Sensor AIM2. J Immunol. Jan. 1, 2016;196(1):29-33. doi:10.4049/jimmunol.1501048.
Schnepp et al., Characterization of adeno-associated virus genomes isolated from human tissues. J Virol. Dec. 2005;79(23):14793-803.
Seiler et al., Adeno-associated virus types 5 and 6 use distinct receptors for cell entry. Hum Gene Ther. Jan. 2006;17(1):10-9.
Snyder et al., Comparison of adeno-associated viral vector serotypes for spinal cord and motor neuron gene delivery. Hum Gene Ther. Sep. 2011;22(9):1129-35. doi: 10.1089/hum.2011.008. Epub Jul. 25, 2011.
Sondhi et al., Enhanced survival of the LINCL mouse following CLN2 gene transfer using the rh. 10 rhesus macaque-derived adeno-associated virus vector. Mol Ther. Mar. 2007;15(3):481-91. Epub Dec. 19, 2006.
Song et al., Intramuscular administration of recombinant adeno-associated virus 2 alpha-1 antitrypsin (rAAV-SERPINA1) vectors in a nonhuman primate model: safety and immunologic aspects. Mol Ther. Sep. 2002;6(3):329-35.

Stoica et al., Targeting Human SOD1 Using AAV mediated RNAi in a mouse model of amyotrophic lateral sclerosis. Mol ther. Jun. 2013;21(1):S149.
Storek et al., Intrathecal long-term gene expression by self-complementary adeno-associated virus type 1 suitable for chronic pain studies in rats. Mol Pain. Jan. 30, 2006;2:4.
Storkebaum et al., Treatment of motoneuron degeneration by intracerebroventricular delivery of VEGF in a rat model of ALS. Nat Neurosci. Jan. 2005;8(1):85-92. Epub Nov. 28, 2004.
Tenenbaum et al., Recombinant AAV-mediated gene delivery to the central nervous system. J Gene Med. Feb. 2004;6 Suppl 1:S212-22.
Tomar et al., Use of adeno-associated viral vector for delivery of small interfering RNA. Oncogene. Aug. 28, 2003;22(36):5712-5.
Towne et al., Systemic AAV6 delivery mediating RNA interference against SOD1: neuromuscular transduction does not alter disease progression in fALS mice. Mol Ther. Jun. 2008;16(6):1018-25. doi: 10.1038/mt.2008.73. Epub Apr. 15, 2008.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.
Vandenberghe et al., Heparin binding directs activation of T cells against adeno-associated virus serotype 2 capsid. Nat Med. Aug. 2006;12(8):967-71. Epub Jul. 16, 2006.
Vandenberghe et al., Tailoring the AAV vector capsid for gene therapy. Gene Ther. Mar. 2009;16(3):311-9. Epub Dec. 4, 2008.
Vandendriessche et al., Efficacy and safety of adeno-associated viral vectors based on serotype 8 and 9 vs. lentiviral vectors for hemophilia B gene therapy. J Thromb Haemost. Jan. 2007;5(1):16-24. Epub Sep. 26, 2006.
Virella-Lowell et al., Enhancing rAAV vector expression in the lung. J Gene Med. Jul. 2005;7(7):842-50.
Vulchanova et al., Differential adeno-associated virus mediated gene transfer to sensory neurons following intrathecal delivery by direct lumbar puncture. Mol Pain. May 28, 2010;6:31. doi: 10.1186/1744-8069-6-31.
Wang et al., Neuroprotective effects of glial cell line-derived neurotrophic factor mediated by an adeno-associated virus vector in a transgenic animal model of amyotrophic lateral sclerosis. J Neurosci. Aug. 15, 2002;22(16):6920-8.
Wang et al., Rescue and replication of adeno-associated virus type 2 as well as vector DNA sequences from recombinant plasmids containing deletions in the viral inverted terminal repeats: selective encapsidation of viral genomes in progeny virions. J Virol. Mar. 1996; 70(3):1668-77.
Wang et al., Somatically Repairing Compound Heterozygous Recessive Mutations by Chromosomal Cut-and-Paste for in Vivo Gene Therapy. May 2016. 24(1):S289. Abstract 733.
Wang et al., Sustained correction of disease in naive and AAV2-pretreated hemophilia B dogs: AAV2/8-mediated, liver-directed gene therapy. Blood. Apr. 15, 2005;105(8):3079-86. Epub Jan. 6, 2005.
Wang et al., The design of vectors for RNAi delivery system. Curr Pharm Des. 2008;14(13):1327-40.
Wang et al., The potential of adeno-associated viral vectors for gene delivery to muscle tissue. Expert Opin Drug Deliv. Mar. 2014;11(3):345-64. doi: 10.1517/17425247.2014.871258. Epub Jan. 3, 2014.
Wang et al., Widespread spinal cord transduction by intrathecal injection of rAAV delivers efficacious RNAi therapy for amyotrophic lateral sclerosis. Hum Mol Genet. Feb. 1, 2014;23(3):668-81. doi: 10.1093/hmg/ddt454. Epub Sep. 18, 2013.
Weismann et al., Systemic AAV9 gene transfer in adult GM1 gangliosidosis mice reduces lysosomal storage in CNS and extends lifespan. Hum Mol Genet. Aug. 1, 2015;24(15):4353-64. doi: 10.1093/hmg/ddv168. Epub May 10, 2015.
Weismann, Approaches and Considerations Towards a Safe and Effective Adena-Associated Virus Mediated Therapeutic Intervention for GM 1-Gangliosidosis: A Dissertation. University Massachusetts Medical School. Aug. 5, 2014.
Wu et al., Alpha2,3 and alpha2,6 N-linked sialic acids facilitate efficient binding and transduction by adeno-associated virus types 1 and 6. J Virol. Sep. 2006;80(18):9093-103.
Xie et al., Isolation of transcriptionally active novel AAV capsid sequences from chimpanzee tissues for vector development. Meet-

(56) References Cited

OTHER PUBLICATIONS ing Abstract: 12th Annual Meeting of the American Society of Gene Therapy. May 1, 2009. Abstract 91.

Xie et al., 676. DNA Sequences Encoding shRNAs Can Replace Mutant ITR in scAAV Genome for Efficient Replication and Packaging and Transcribe shRNAs by pol III Promoter Activity of wt ITR for Efficient Gene Silencing Mol Therapy. May 2015;23(1):S269.

Xie et al., Characterization of positioning effect of pol III-shRNA transcription unit in scAAV vector genome on the packaging efficiency and functionality of shRNA silencing. Molecular Therapy. May 2010;18(1):S262. Abstract 671.

Xie et al., MicroRNA regulated tissue specific transduction by rAAV vector. Molecular Therapy. May 2009;17(1):S279. Abstract 732.

Xie et al., MicroRNA-regulated, systemically delivered rAAV9: a step closer to CNS-restricted transgene expression. Mol Ther. Mar. 2011;19(3):526-35. doi: 10.1038/mt.2010.279. Epub Dec. 21, 2010.

Xie et al., rAAV-mediated delivery of micro RNA scavengers leads to efficient and stable knock-down of cognate micro RNAs, upregulation of their natural target genes and phenotypic changes in mice. Molecular Therapy. May 2010;18(1): S140. Abstract 362.

Xie et al., Short DNA Hairpins Compromise Recombinant Adeno-Associated Virus Genome Homogeneity. Mol Ther. Jun. 7, 2017;25(6):1363-1374. doi: 10.1016/j.ymthe.2017.03.028. Epub Apr. 24, 2017.

Xu et al., Delivery of MDR1 small interfering RNA by self-complementary recombinant adeno-associated virus vector. Mol Ther. Apr. 2005;11(4):523-30.

Yan et al., Unique biologic properties of recombinant AAV1 transduction in polarized human airway epithelia. J Biol Chem. Oct. 6, 2006;281(40):29684-92. Epub Aug. 9, 2006.

Zabner et al., Adeno-associated virus type 5 (AAV5) but not AAV2 binds to the apical surfaces of airway epithelia and facilitates gene transfer. J Virol. Apr. 2000;74(8):3852-8.

Zhang et al., Characterization of 12 AAV vectors for intravascular delivery to target CNS and detarget non-CNS tissues by mirna regulation: implications in treatment of canavan disease. Molecular Therapy. May 2010;18(1): S174. Abstract 450.

Zhong et al., Chimpanzee-derived novel natural variants of aav9: vector development and interrogation of correlations between capsid structure and vector biology. Molecular Therapy. May 2010;18(1): S24. Abstract 58.

Zincarelli et al., Analysis of AAV serotypes 1-9 mediated gene expression and tropism in mice after systemic injection. Mol Ther. Jun. 2008;16(6):1073-80. doi: 10.1038/mt.2008.76. Epub Apr. 15, 2008.

Zolotukhin et al., Production and purification of serotype 1, 2, and 5 recombinant adeno-associated viral vectors. Methods. Oct. 2002;28(2):158-67.

PCT/US2017/037796, Oct. 27, 2017, International Search Report and Written Opinion.

* cited by examiner

| HDR | Dose | No. Embryos | Embryos with indels | Embryos with HDR | HDR Gene Editing Frequency (%) |
|---|---|---|---|---|---|
| Single Nucleotide Transversion | Low1 | 15 | 14 | 6 | 40 |
| BFP Insertion | Low2 | 8 | n.d. | 2 | 25 |
| | High3 | 7 | n.d. | 4 | 57 |

1 rAAV6-spCas9 (3 x 10⁸ GCs); rAAV6-sgTyr (3 x 10⁸ GCs); rAAV6-Tyr-SNT donor (3 x 10⁹ GCs).
2 rAAV6-spCas9 (3 x 10⁸ GCs); rAAV6-sgTyr (3 x 10⁸ GCs); rAAV6-Tyr-BFP donor (3 x 10⁹ GCs).
3 rAAV6-spCas9 (1.5 x 10⁹ GCs); rAAV6-sgTyr (1.5 x 10⁹ GCs); rAAV6-Tyr-BFP donor (3 x 10⁹ GCs).
n.d., not determined

FIG. 2F

| Vector Injected[1] | No. Litters | No. Pups[2] | Tyr Edited Pups (albino)[3] | Tyr Editing Frequency (%)[4] |
|---|---|---|---|---|
| rAAV6-SpCas9 + rAAV6-sgTyr | 5 | 29 | 3 (2) | 10 |

[1] Only left oviduct was injected
[2] Includes pups from injected and non-injected oviducts
[3] Gene editing evidence determined by assessing coat color and sequence analysis
[4] Approximate frequency; includes pups from treated and non-treated oviducts

FIG. 3F

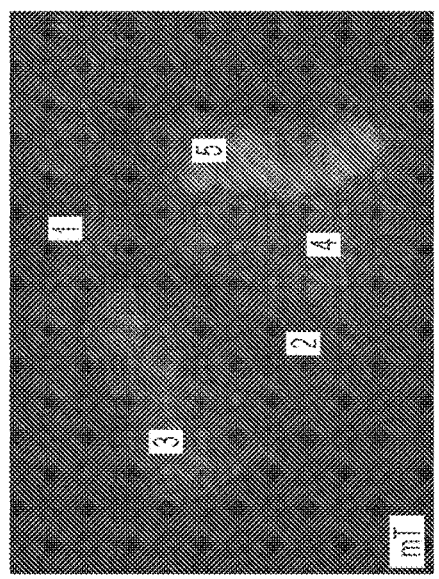
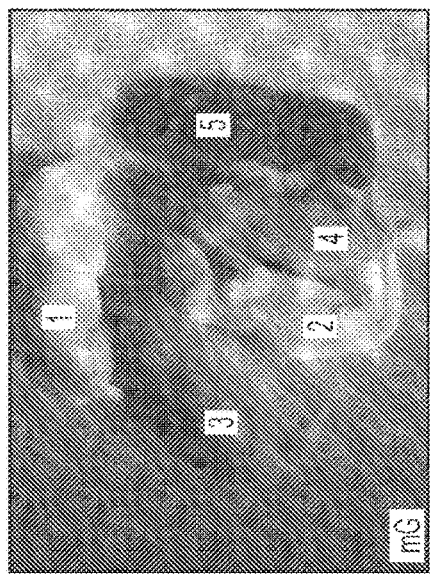
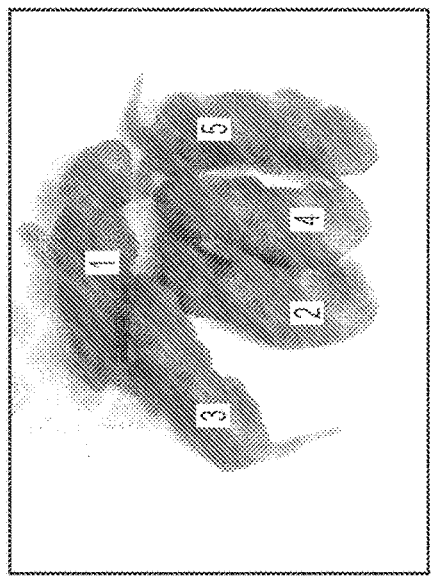
FIG. 5D

5' TTGTTGGCAAAAGAATGCTGCCCACCATGGATGGGTGATGGGAGTCCCTGCGGCCAGC
TTTCAGGCAGAGGTTCCTGCCAGGATATCCTTCTGTCCAGTGCACCATCTGGACCTCAGT
TCCCCTTCAAAGGGGTGGATGACCGTGAGTCCTGGCCCTCTGTGTTTTATAATAGGACCT
GCCAGTGCTCAGGCAACTTCATGGGTTTCAACTGCGGAAACTGTAAGTTTGGATTTGGGG
GCCCAAATTGTACAGAGAAGCGAGTCTTGATTAGAAGAAACATTTTTGATTTGAGTGTCT
CCGAAAAGAATAAGTTCTTTTCTTACCTCACTTTAGCAAAACATACTATCAGCTCAGTCT
ATGTCATCCCCACAGGCACCTATGGCCAAATGAACAATGGGTCAACACCCATGTTTAATG
ATATCAACATCTACGACCTCTTTGTATGGATGCATTACTATGTGTCAAGGGACACACTGC
TTGGGGGCTCTGAAATATGGAGGACATTGATTTTGCCCATGAAGC-3'

FIG. 7C

| ID | guide RNA and PAM | orientation | T7EI bands (bp) |
|----|---|---|---|
| 1 | TCAGTTCCCCTTCAAAGGGGTGG | sense | 394, 130 |
| 2 | GGTCCTATTATAAAACACAGAAGG | antisense | 364, 160 |
| 3 | GGTCATCCACCCCTTTGAAGGGG | antisense | 399, 125 |
| 4 | AACTTCATGGGTTTCAACTGCGG | sense | 315, 209 |
| 5 | GGGTGGATGACCGTGAGTCCTGG | sense | 377, 147 |

| Sample ID | Barcode & primer (5'→3') | Barcode alone (5'→3') |
|---|---|---|
| Tyr_Fwd_10 | GCGCTCTGTGTGCAGC TTGTTGGCAAAAGAATGCTG | GCGCTCTGTGTGCAGC |
| Tyr_Fwd_11 | TCATGAGTCGACACTA TTGTTGGCAAAAGAATGCTG | TCATGAGTCGACACTA |
| Tyr_Fwd_12 | TATCTATCGTATACGC TTGTTGGCAAAAGAATGCTG | TATCTATCGTATACGC |
| Tyr_Fwd_1 | ATCACACTGCATCTGA TTGTTGGCAAAAGAATGCTG | ATCACACTGCATCTGA |
| Tyr_Fwd_3 | ACGTACGCTCGTCATA TTGTTGGCAAAAGAATGCTG | ACGTACGCTCGTCATA |
| Tyr_Fwd_2 | TGTGAGTCAGTACGCG TTGTTGGCAAAAGAATGCTG | TGTGAGTCAGTACGCG |
| Tyr_Fwd_6 | AGAGACACGATACTCA TTGTTGGCAAAAGAATGCTG | AGAGACACGATACTCA |
| Tyr_Fwd_4 | CTGCTAGAGTCTACAG TTGTTGGCAAAAGAATGCTG | CTGCTAGAGTCTACAG |
| Tyr_Fwd_5 | AGCACTCGCGTCAGTG TTGTTGGCAAAAGAATGCTG | AGCACTCGCGTCAGTG |
| Tyr_Fwd_7 | TCATGCACGTCTCGCT TTGTTGGCAAAAGAATGCTG | TCATGCACGTCTCGCT |
| Tyr_Fwd_9 | AGAGCATCTCTGTACT TTGTTGGCAAAAGAATGCTG | AGAGCATCTCTGTACT |
| Tyr_Fwd_8 | CGCATCGACTACGCTA TTGTTGGCAAAAGAATGCTG | CGCATCGACTACGCTA |
| Tyr_Rev_10 | AGAGTACTACATATGA GCTTCATGGGCAAAATCAAT | AGAGTACTACATATGA |
| Tyr_Rev_11 | CGTGTGCATAGATCGC GCTTCATGGGCAAAATCAAT | CGTGTGCATAGATCGC |
| Tyr_Rev_12 | ATGTATCTCGACTGCA GCTTCATGGGCAAAATCAAT | ATGTATCTCGACTGCA |
| Tyr_Rev_1 | GACTCGACGCAGAGTC GCTTCATGGGCAAAATCAAT | GACTCGACGCAGAGTC |
| Tyr_Rev_3 | CGATGACGTCGCTGTA GCTTCATGGGCAAAATCAAT | CGATGACGTCGCTGTA |
| Tyr_Rev_2 | CACACGTAGTCTGCGC GCTTCATGGGCAAAATCAAT | CACACGTAGTCTGCGC |
| Tyr_Rev_6 | GCTGTATCGCAGAGAC GCTTCATGGGCAAAATCAAT | GCTGTATCGCAGAGAC |
| Tyr_Rev_4 | CGAGCTATCTCATACT GCTTCATGGGCAAAATCAAT | CGAGCTATCTCATACT |
| Tyr_Rev_5 | CATGAGTACTCGTCGC GCTTCATGGGCAAAATCAAT | CATGAGTACTCGTCGC |
| Tyr_Rev_7 | CAGCGACTGTGATACT GCTTCATGGGCAAAATCAAT | CAGCGACTGTGATACT |
| Tyr_Rev_9 | TGTCGCATCATATGAT GCTTCATGGGCAAAATCAAT | TGTCGCATCATATGAT |
| Tyr_Rev_8 | GCTGTGATCTACGTCT GCTTCATGGGCAAAATCAAT | GCTGTGATCTACGTCT |

FIG. 9A

| Detected unique reads | | Indel-type |
|---|---|---|
| GCTCAGGCAACTTCATGGGTTTCAA | CTGCGGAAACTGTAAGTTTGGATTT | Reference |
| GCTCAGGCAACTTCATGGGTTTCAAA | CTGCGGAAACTGTAAGTTTGGATTT | insertion |
| GCTCAGGCAACTTCATGGGTTTCAAAA | CTGCGGAAACTGTAAGTTTGGATTT | insertion |
| GCTCAGGCAACTTCATGGGTTTCAAAT | CTGCGGAAACTGTAAGTTTGGATTT | insertion |
| GCTCAGGCAACTTCATGGGTTTCAAT | CTGCGGAAACTGTAAGTTTGGATTT | insertion |
| GCTCAGGCAACTTCATGGGTTT---- | CTGCGGAAACTGTAAGTTTGGATTT | deletion |
| GCTCAGGCAACTTCATGGGTTTC-- | -TGCGGAAACTGTAAGTTTGGATTT | deletion |
| GCTCAGGCAACTTCATGGGTTTC-- | CTGCGGAAACTGTAAGTTTGGATTT | deletion |
| GCTCAGGCAACTTCATGGGTTTCA- | -TGCGGAAACTGTAAGTTTGGATTT | deletion |
| GCTCAGGCAACTTCATGGGTTTCA- | CTGCGGAAACTGTAAGTTTGGATTT | deletion |
| GCTCAGGCAACTTCATGGGTTTCAA | -TGCGGAAACTGTAAGTTTGGATTT | deletion |
| GCTCAGGCAACTTCATGGGTTTCAA | CT--GGAAACTGTAAGTTTGGATTT | deletion |
| GCTCAGGCAACTTCATGGGTTTCAT | CTGCGGAAACTGTAAGTTTGGATTT | alteration |
| ------------------------- | -------------------------G | large deletion |
| ------------------------- | --GCGGAAACTGTAAGTTTGGATTT | large deletion |
| GCTCAGGCAACTTCATGGGTTT--A | CTGCGGAAACTGTAAGTTTGGATTT | complex |
| GCTCAGGCAACTTCATGGGTTTC-T | CTGCGGAAACTGTAAGTTTGGATTT | complex |
| GCTCAGGCAACTTCATGGGTTTCA- | --TTGGAAACTGTAAGTTTGGATTT | complex |
| GCTCAGGCAACTTCATGGGTTTCAA | ----TGAAACTGTAAGTTTGGATTT | complex |
| GCTCAGGCAACTTCATGGGTTTCAA | ---TGGAAACTGTAAGTTTGGATTT | complex |
| GCTCAGGCAACTTCATGGGTTTCAT | ----GGAAACTGTAAGTTTGGATTT | complex |
| GCTCAGGCAACTTCATGGGTTTCAT | CT--GGAAACTGTAAGTTTGGATTT | complex |

FIG. 9B

| Large Scale (Dose) | Small Scale (Dose) | Embryo ID | Edited/ Total Clones | Gene Editing (Frequency) |
| --- | --- | --- | --- | --- |
| rAAV-Cas9 ($1 \times 10^9$ GCs) | rAAV-sgTyr ($1 \times 10^9$ GCs) | 1 | 6/7 | 56/58 (97%) |
| | | 2 | 6/7 | |
| | | 3 | 8/8 | |
| | | 4 | 8/8 | |
| | | 5 | 6/6 | |
| | | 6 | 8/8 | |
| | | 7 | 8/8 | |
| | | 8 | 6/6 | |

| Large Scale (Dose) | Small Scale (Dose) | Embryo ID | Edited/ Total Clones | Gene Editing (Frequency) |
|---|---|---|---|---|
| rAAV6-Cas9 ($3 \times 10^9$ GCs) | rAAV6-sgFahExon ($3 \times 10^9$ GCs) | 1 | 7/7 | 29/29 (100%) |
| | | 2 | 7/7 | |
| | | 3 | 7/7 | |
| | | 4 | 8/8 | |
| rAAV6-Cas9 ($3 \times 10^8$ GCs) | rAAV6-sgFahExon ($3 \times 10^8$ GCs) | 1 | 8/8 | 25/27 (93%) |
| | | 2 | 8/8 | |
| | | 3 | 5/5 | |
| | | 4 | 4/6 | |

SEQUENCE LISTING

```
<160> NUMBER OF SEQ ID NOS: 108

<210> SEQ ID NO 1
<211> LENGTH: 736
<212> TYPE: PRT
<213> ORGANISM: adeno-associated virus 6

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60
```

```
Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
             85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro
    115                 120                 125

Phe Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480
```

```
Gly Pro Cys Tyr Arg Gln Gln Arg Val Ser Lys Thr Lys Thr Asp Asn
                485                 490                 495
Asn Asn Ser Asn Phe Thr Trp Thr Gly Ala Ser Lys Tyr Asn Leu Asn
            500                 505                 510
Gly Arg Glu Ser Ile Ile Asn Pro Gly Thr Ala Met Ala Ser His Lys
        515                 520                 525
Asp Asp Lys Asp Lys Phe Phe Pro Met Ser Gly Val Met Ile Phe Gly
    530                 535                 540
Lys Glu Ser Ala Gly Ala Ser Asn Thr Ala Leu Asp Asn Val Met Ile
545                 550                 555                 560
Thr Asp Glu Glu Glu Ile Lys Ala Thr Asn Pro Val Ala Thr Glu Arg
                565                 570                 575
Phe Gly Thr Val Ala Val Asn Leu Gln Ser Ser Ser Thr Asp Pro Ala
            580                 585                 590
Thr Gly Asp Val His Val Met Gly Ala Leu Pro Gly Met Val Trp Gln
        595                 600                 605
Asp Arg Asp Val Tyr Leu Gln Gly Pro Ile Trp Ala Lys Ile Pro His
    610                 615                 620
Thr Asp Gly His Phe His Pro Ser Pro Leu Met Gly Gly Phe Gly Leu
625                 630                 635                 640
Lys His Pro Pro Pro Gln Ile Leu Ile Lys Asn Thr Pro Val Pro Ala
                645                 650                 655
Asn Pro Pro Ala Glu Phe Ser Ala Thr Lys Phe Ala Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Val Gln Tyr Thr Ser Asn
    690                 695                 700
Tyr Ala Lys Ser Ala Asn Val Asp Phe Thr Val Asp Asn Asn Gly Leu
705                 710                 715                 720
Tyr Thr Glu Pro Arg Pro Ile Gly Thr Arg Tyr Leu Thr Arg Pro Leu
                725                 730                 735

<210> SEQ ID NO 2
<211> LENGTH: 2208
<212> TYPE: DNA
<213> ORGANISM: adeno-associated virus 6

<400> SEQUENCE: 2
atggctgccg atggttatct tccagattgg ctcgaggaca acctctctga gggcattcgc      60
gagtggtggg acttgaaacc tggagccccg aaacccaaag ccaaccagca aaagcaggac     120
gacggccggg gtctggtgct tcctggctac aagtacctcg acccttcaa cggactcgac      180 aagggggagc ccgtcaacgc ggcggatgca gcggccctcg agcacgacaa ggcctacgac     240
cagcagctca agcgggtga caatccgtac ctgcggtata ccacgccga cgccgagttt      300 caggagcgtc tgcaagaaga tacgtctttt ggggggcaacc tcgggcgagc agtcttccag     360
gccaagaaga gggttctcga accttttggt ctggttgagg aaggtgctaa gacggctcct     420
ggaaagaaac gtccggtaga gcagtcgcca caagagccag actcctcctc gggcattggc     480
aagacaggcc agcagcccgc taaaaagaga ctcaattttg gtcagactgg cgactcagag     540
tcagtccccg acccacaacc tctcggagaa cctccagcaa ccccgctgc tgtgggacct     600 actacaatgg cttcaggcgg tggcgcacca atggcagaca taacgaagg cgccgacgga     660 gtgggtaatg cctcaggaaa ttggcattgc gattccacat ggctgggcga cagagtcatc     720
```

```
accaccagca cccgaacatg ggccttgccc acctataaca accacctcta caagcaaatc      780
tccagtgctt caacggggc cagcaacgac aaccactact tcggctacag cacccctgg       840 gggtattttg atttcaacag attccactgc catttctcac cacgtgactg gcagcgactc      900
atcaacaaca attggggatt ccggcccaag agactcaact tcaagctctt caacatccaa      960
gtcaaggagg tcacgacgaa tgatggcgtc acgaccatcg ctaataaccct taccagcacg     1020 gttcaagtct tctcggactc ggagtaccag ttgccgtacg tcctcggctc tgcgcaccag      1080
ggctgcctcc ctccgttccc ggcggacgtg ttcatgattc cgcagtacgg ctacctaacg      1140
ctcaacaatg gcagccaggc agtgggacgg tcatccttt actgcctgga atatttccca      1200
tcgcagatgc tgagaacggg caataacttt accttcagct cacccttcga ggacgtgcct     1260
ttccacagca gctacgcgca cagccagagc ctggaccggc tgatgaatcc tctcatcgac      1320
cagtacctgt attacctgaa cagaactcag aatcagtccg gaagtgccca aaacaaggac      1380
ttgctgttta gccgggggtc tccagctggc atgtctgttc agcccaaaaa ctggctacct      1440
ggaccctgtt accggcagca gcgcgtttct aaaacaaaaa cagacaacaa caacagcaac      1500
tttacctgga ctggtgcttc aaatataac cttaatgggc gtgaatctat aatcaaccct      1560
ggcactgcta tggcctcaca caaagacgac aaagacaagt tctttcccat gagcggtgtc      1620 atgattttg gaaggagag cgccggagct tcaaacactg cattggacaa tgtcatgatc       1680
acagacgaag aggaaatcaa agccactaac cccgtggcca ccgaaagatt tgggactgtg      1740
gcagtcaatc tccagagcag cagcacagac cctgcgaccg gagatgtgca tgttatggga      1800
gccttacctg gaatggtgtg gcaagacaga gacgtatacc tgcagggtcc tatttgggcc      1860
aaaattcctc acacggatgg acactttcac ccgtctcctc tcatgggcgg ctttggactt      1920
aagcacccgc ctcctcagat cctcatcaaa aacacgcctg ttcctgcgaa tcctccggca      1980
gagttttcgg ctacaaagtt tgcttcattc atcacccagt attccacagg acaagtgagc      2040
gtggagattg aatgggagct gcagaaagaa acagcaaac gctggaatcc cgaagtgcag      2100
tatacatcta actatgcaaa atctgccaac gttgatttca ctgtggacaa caatggactt      2160
tatactgagc ctcgccccat ggcacccgt tacctcaccc gtcccctg               2208
```

<210> SEQ ID NO 3
<211> LENGTH: 1965
<212> TYPE: DNA
<213> ORGANISM: Artificial Sequence
<220> FEATURE:
<223> OTHER INFORMATION: Synthetic Polynucleotide

<400> SEQUENCE: 3

```
ctgcgcgctc gctcgctcac tgaggccgcc cgggcaaagc ccgggcgtcg ggcgaccttt       60
ggtcgcccgg cctcagtgag cgagcgagcg cgcagagagg gagtgtagcc atgctctagg     120
aagatcaatt cggtacaatt cacgcgtcga cattgattat tgactagtta ttaatagtaa     180
tcaattacgg ggtcattagt tcatagccca tatatggagt tccgcgttac ataacttacg     240
gtaaatggcc cgcctggctg accgcccaac gacccccgcc cattgacgtc aataatgacg     300
tatgttccca tagtaacgcc aatagggact ttccattgac gtcaatgggt ggagtattta     360
cggtaaactg cccacttggc agtacatcaa gtgtatcata tgccaagtac gccccctatt     420
gacgtcaatg acggtaaatg gcccgcctgg cattatgccc agtacatgac cttatgggac     480
tttcctactt ggcagtacat ctacgtatta gtcatcgcta ttaccatgtc gaggccacgt     540
```

```
tctgcttcac tctccccatc tccccccct cccacccc aattttgtat ttatttattt      600
tttaattatt ttgtgcagcg atggggcgg gggggggg cgcgcgccag gcggggcggg      660
gcggggcgag gggcggggcg gggcgaggcg gagaggtgcg gcggcagcca atcagagcgg   720
cgcgctccga aagtttcctt ttatggcgag gcggcggcgg cggcggccct ataaaaagcg   780
aagcgcgcgg cgggcgggag caagctctag cctcgagaat tacttaatac gactcactat   840
aggctagtaa tacgactcac tatagatggt gagcaagggc gaggagctgt tcaccggggt   900
ggtgcccatc ctggtcgagc tggacggcga cgtaaacggc cacaagttca gcgtgtccgg   960
cgagggcgag ggcgatgcca cctacggcaa gctgaccctg aagttcatct gcaccaccgg  1020
caagctgccc gtgccctggc ccaccctcgt gaccaccctg acctacggcg tgcagtgctt  1080
cagccgctac cccgaccaca tgaagcagca cgacttcttc aagtccgcca tgcccgaagg  1140
ctacgtccag gagcgcacca tcttcttcaa ggacgacggc aactacaaga cccgcgccga  1200
ggtgaagttc gagggcgaca ccctggtgaa ccgcatcgag ctgaagggca tcgacttcaa  1260
ggaggacggc aacatcctgg ggcacaagct ggagtacaac tacaacagcc acaacgtcta  1320
tatcatggcc gacaagcaga agaacggcat caaggtgaac ttcaagatcc gccacaacat  1380
cgaggacggc agcgtgcagc tcgccgacca ctaccagcag aacacccca tcggcgacgg  1440
ccccgtgctg ctgcccgaca accactacct gagcacccag tccgccctga gcaaagaccc  1500
caacgagaag cgcgatcaca tggtcctgct ggagttcgtg accgccgccg ggatcactct  1560
cggcatggac gagctgtaca agtaaagcgg ccctagcgtt taaacgggcc ctctagagtc  1620
gacccgggcg gcctcgagga cggggtgaac tacgcctgag gatccgatct ttttccctct  1680
gccaaaaatt atgggacat catgaagccc cttgagcatc tgacttctgg ctaataaagg  1740
aaatttattt tcattgcaat agtgtgttgg aattttttgt gtctctcact cggcctaggt  1800
agataagtag catggcgggt taatcattaa ctacaaggaa cccctagtga tggagttggc  1860
cactccctct ctgcgcgctc gctcgctcac tgaggccggg cgaccaaagg tcgcccgacg  1920
cccgggcttt gcccgggcgg cctcagtgag cgagcgagcg cgcag                 1965
```

<210> SEQ ID NO 4
<211> LENGTH: 239
<212> TYPE: PRT
<213> ORGANISM: Artificial Sequence
<220> FEATURE:
<223> OTHER INFORMATION: Synthetic Polypeptide

<400> SEQUENCE: 4

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 5
<211> LENGTH: 2648
<212> TYPE: DNA
<213> ORGANISM: Artificial Sequence
<220> FEATURE:
<223> OTHER INFORMATION: Synthetic Polynucleotide

<400> SEQUENCE: 5

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctaccag gtaatgggg     180
atcctctaga actatagcta gtcgacattg attattgact agttattaat agtaatcaat     240
tacgggtca ttagttcata gcccatatat ggagttccgc gttacataac ttacggtaaa     300
tggcccgcct ggctgaccgc ccaacgaccc cgcccattg acgtcaataa tgacgtatgt      360
tcccatagta acgccaatag ggactttcca ttgacgtcaa tgggtggagt atttacggta     420
aactgcccac ttggcagtac atcaagtgta tcatatgcca gtacgccccc ctattgacgt     480
caatgacggt aaatggcccg cctggcatta tgcccagtac atgaccttat gggactttcc     540
tacttggcag tacatctacg tattagtcat cgctattacc atgtcgaggc acgttctgc     600
ttcactctcc ccatctcccc cccctcccca ccccaatttt gtatttatt tattttttaa     660
ttatttgtg cagcgatggg ggcgggggggg gggggcgcgc gccaggcggg gcgggcgggg     720
gcgaggggcg gggcggggcg aggcggagag gtgcggcggc agccaatcag agcggcgcgc     780
tccgaaagtt tccttttatg gcgaggcggc ggcggcggcg gccctataaa aagcgaagcg     840
cgcggcgggc gggagcaagc tttattgcgg tagtttatca cagttaaatt gctaacgcag     900
tcagtgcttc tgacacaaca gtctcgaact taagctgcag aagttggtcg tgaggcactg     960
ggcaggtaag tatcaaggtt acaagacagg tttaaggaga ccaatagaaa ctgggcttgt    1020
cgagacagag aagactcttg cgtttctgat aggcacctat tggtcttact gacatccact    1080
ttgcctttct ctccacaggt gtccactccc agttcaatta cagctcttaa ggctagagta    1140
cttaatacga ctcactatag gctagcctcg agaattgtac actttactta aaaccattat    1200
ctgagtgtga atgtccaat ttactgaccg tacaccaaaa tttgcctgca ttaccggtcg    1260
atgcaacgag tgatgaggtt cgcaagaacc tgatggacat gttcagggat cgccaggcgt    1320
tttctgagca tacctggaaa atgcttctgt ccgtttgccg gtcgtgggcg gcatggtgca    1380
```

```
agttgaataa ccggaaatgg tttcccgcag aacctgaaga tgttcgcgat tatcttctat    1440
atcttcaggc gcgcggtctg gcagtaaaaa ctatccagca acatttgggc cagctaaaca    1500
tgcttcatcg tcggtccggg ctgccacgac caagtgacag caatgctgtt tcactggtta    1560
tgcggcggat ccgaaaagaa aacgttgatg ccggtgaacg tgcaaaacag gctctagcgt    1620
tcgaacgcac tgatttcgac caggttcgtt cactcatgga aaatagcgat cgctgccagg    1680
atatacgtaa tctggcattt ctggggattg cttataacac cctgttacgt atagccgaaa    1740
ttgccaggat cagggttaaa gatatctcac gtactgacgg tgggagaatg ttaatccata    1800
ttggcagaac gaaaacgctg gttagcaccg caggtgtaga aaggcactt agcctggggg    1860 taactaaact ggtcgagcga tggatttccg tctctggtgt agctgatgat ccgaataact    1920
acctgttttg ccgggtcaga aaaaatggtg ttgccgcgcc atctgccacc agccagctat    1980
caactcgcgc cctggaaggg attttgaag caactcatcg attgatttac ggcgctaagg    2040
atgactctgg tcagagatac ctggcctggt ctggacacag tgcccgtgtc ggagccgcgc    2100
gagatatggc ccgcgctgga gtttcaatac cggagatcat gcaagctggt ggctggacca    2160
atgtaaatat tgtcatgaac tatatccgta acctggatag tgaaacaggg gcaatggtgc    2220
gcctgctgga agatggcgat tagccattaa cgcggcgtgg tacctctaga gtcgaggacg    2280
gggtgaacta cgcctgagga tccgatcttt ttccctctgc caaaaattat ggggacatca    2340
tgaagcccct tgagcatctg acttctggct aataaaggaa atttatttc attgcaatag    2400 tgtgttggaa ttttttgtgt ctctcactcg gaagcaattc gttgatctga atttcgacca    2460
cccataatac ccattaccct ggtagataag tagcatggcg ggttaatcat taactacaag    2520 gaaccctag tgatggagtt ggccactccc tctctgcgcg ctcgctcgct cactgaggcc    2580
gggcgaccaa aggtcgcccg acgcccgggc tttgcccggg cggcctcagt gagcgagcga    2640
gcgcgcag                                                              2648
```

<210> SEQ ID NO 6
<211> LENGTH: 343
<212> TYPE: PRT
<213> ORGANISM: Artificial Sequence
<220> FEATURE:
<223> OTHER INFORMATION: Synthetic Polypeptide

<400> SEQUENCE: 6

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

```
Glu Arg Ala Lys Gln Ala Leu Ala Phe Glu Arg Thr Asp Phe Asp Gln
            130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
            195                 200                 205

Val Glu Lys Ala Leu Ser Leu Gly Val Thr Lys Leu Val Glu Arg Trp
210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
            275                 280                 285

His Ser Ala Arg Val Gly Ala Ala Arg Asp Met Ala Arg Ala Gly Val
            290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340

<210> SEQ ID NO 7
<211> LENGTH: 4898
<212> TYPE: DNA
<213> ORGANISM: Artificial Sequence
<220> FEATURE:
<223> OTHER INFORMATION: Synthetic Polynucleotide

<400> SEQUENCE: 7
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggcctct agaatggagg cggtactatg tagatgagaa     180
ttcaggagca aactgggaaa agcaactgct tccaaatatt tgtgattttt acagtgtagt     240
tttggaaaaa ctcttagcct accaattctt ctaagtgttt taaatgtggg agccagtac      300 acatgaagtt atagagtgtt ttaatgaggc ttaaatattt accgtaacta tgaaatgcta     360
cgcatatcat gctgttcagg ctccgtggcc acgcaactca tactaccggt gccaccatgt     420
acccatacga tgttccagat tacgcttcgc gaagaaaaa gcgcaaggtc gaagcgtccg     480
acaagaagta cagcatcggc ctggacatcg gcaccaactc tgtgggctgg gccgtgatca     540
ccgacgagta caaggtgccc agcaagaaat tcaaggtgct gggcaacacc gaccggcaca     600
gcatcaagaa gaacctgatc ggagccctgc tgttcgacag cggcgaaaca gccgaggcca     660
cccggctgaa gagaaccgcc agaagaagat acaccagacg gaagaaccgg atctgctatc     720
tgcaagagat cttcagcaac gagatggcca aggtggacga cagcttcttc cacagactgg     780
aagagtcctt cctggtggaa gaggataaga agcacgagcg gcaccccatc ttcggcaaca     840
```

```
tcgtggacga ggtggcctac cacgagaagt accccaccat ctaccacctg agaaagaaac    900
tggtggacag caccgacaag gccgacctgc ggctgatcta tctggccctg ccccacatga    960
tcaagttccg gggccacttc ctgatcgagg gcgacctgaa ccccgacaac agcgacgtgg   1020
acaagctgtt catccagctg gtgcagacct acaaccagct gttcgaggaa aaccccatca   1080
acgccagcgg cgtggacgcc aaggccatcc tgtctgccag actgagcaag agcagacggc   1140
tggaaaatct gatcgcccag ctgcccggcg agaagaagaa tggcctgttc ggcaacctga   1200
ttgccctgag cctgggcctg accccaaact tcaagagcaa cttcgacctg ccgaggatg    1260 ccaaactgca gctgagcaag gacacctacg acgacgacct ggacaacctg ctggcccaga   1320
tcggcgacca gtacgccgac ctgtttctgg ccgccaagaa cctgtccgac gccatcctgc   1380
tgagcgacat cctgagagtg aacaccgaga tcaccaaggc cccctgagc gcctctatga    1440 tcaagagata cgacgagcac caccaggacc tgaccctgct gaaagctctc gtgcggcagc   1500
agctgcctga agtacaaa gagattttct cgaccagca caagaacggc tacgccggct     1560
acattgacgg cggagccagc caggaagagt tctacaagtt catcaagccc atcctggaaa   1620
agatggacgg caccgaggaa ctgctcgtga agctgaacag agaggacctg ctgcggaagc   1680
agcggacctt cgacaacggc agcatccccc accagatcca cctgggagag ctgcacgcca   1740
ttctgcggcg gcaggaagat ttttacccat tcctgaagga caaccgggaa aagatcgaga   1800
agatcctgac cttccgcatc ccctactacg tgggccctct ggccaggga acagcagat    1860 tcgcctggat gaccagaaag agcgaggaaa ccatcacccc ctggaacttc gaggaagtgg   1920
tggacaaggg cgcttccgcc cagagcttca tcgagcggat gaccaacttc gataagaacc   1980
tgcccaacga aaggtgctg cccaagcaca gcctgctgta cgagtacttc accgtgtata    2040
acgagctgac caaagtgaaa tacgtgaccg agggaatgag aaagcccgcc ttcctgagcg   2100
gcgagcagaa aaaggccatc gtggacctgc tgttcaagac caaccggaaa gtgaccgtga   2160
agcagctgaa agaggactac ttcaagaaaa tcgagtgctt cgactccgtg aaatctccg    2220 gcgtggaaga tcggttcaac gcctccctgg cacataccca cgatctgctg aaaattatca   2280
aggacaagga cttcctggac aatgaggaaa acgaggacat tctggaagat atcgtgctga   2340
ccctgacact gtttgaggac agagagatga tcgaggaacg gctgaaaacc tatgcccacc   2400
tgttcgacga caaagtgatg aagcagctga gcggcggga tacaccggc tggggcaggc    2460 tgagccggaa gctgatcaac ggcatccggg acaagcagtc cggcaagaca atcctggatt   2520
tcctgaagtc cgacggcttc gccaacagaa acttcatgca gctgatccac gacgacagcc   2580
tgacctttaa agaggacatc cagaaagccc aggtgtccgg ccaggggat agcctgcacg    2640 agcacattgc caatctggcc ggcagccccg ccattaagaa gggcatcctg cagacagtga   2700
aggtggtgga cgagctcgtg aaagtgatgg gccggcacaa gcccgagaac atcgtgatcg   2760
aaatggccag agagaaccag accacccaga gggacagaa gaacagccgc gagagaatga   2820
agcggatcga gagggcatc aaagagctgg gcagccagat cctgaaagaa caccccgtgg    2880
aaaacaccca gctgcagaac gagaagctgt acctgtacta cctgcagaat gggcgggata   2940
tgtacgtgga ccaggaactg gacatcaacc ggctgtccga ctacgatgtg gaccatatcg   3000
tgcctcagag ctttctgaag gacgactcca tcgacaacaa ggtgctgacc agaagcgaca   3060
agaaccgggg caagagcgac aacgtgcccct ccgaagaggt cgtgaagaag atgaagaact  3120
actggcggca gctgctgaac gccaagctga ttacccagag aaagttcgac aatctgacca   3180
```

| | |
|---|---|
| aggccgagag aggcggcctg agcgaactgg ataaggccgg cttcatcaag agacagctgg | 3240 |
| tggaaacccg gcagatcaca aagcacgtgg cacagatcct ggactcccgg atgaacacta | 3300 |
| agtacgacga gaatgacaag ctgatccggg aagtgaaagt gatcaccctg aagtccaagc | 3360 |
| tggtgtccga tttccggaag gatttccagt tttacaaagt gcgcgagatc aacaactacc | 3420 |
| accacgccca cgacgcctac ctgaacgccg tcgtgggaac cgccctgatc aaaaagtacc | 3480 |
| ctaagctgga aagcgagttc gtgtacgcg actacaaggt gtacgacgtg cggaagatga | 3540 |
| tcgccaagag cgagcaggaa atcggcaagg ctaccgccaa gtacttcttc tacagcaaca | 3600 |
| tcatgaactt tttcaagacc gagattaccc tggccaacgg cgagatccgg aagcggcctc | 3660 |
| tgatcgagac aaacggcgaa accggggaga tcgtgtggga taagggccgg gattttgcca | 3720 |
| ccgtgcggaa agtgctgagc atgccccaag tgaatatcgt gaaaaagacc gaggtgcaga | 3780 |
| caggcggctt cagcaaagag tctatcctgc ccaagaggaa cagcgataag ctgatcgcca | 3840 |
| gaaagaagga ctgggaccct aagaagtacg gcggcttcga cagccccacc gtggcctatt | 3900 |
| ctgtgctggt ggtggccaaa gtggaaaagg gcaagtccaa gaaactgaag agtgtgaaag | 3960 |
| agctgctggg gatcaccatc atggaaagaa gcagcttcga gaagaatccc atcgactttc | 4020 |
| tggaagccaa gggctacaaa gaagtgaaaa aggacctgat catcaagctg cctaagtact | 4080 |
| ccctgttcga gctggaaaac ggccggaaga atgctggc ctctgccggc gaactgcaga | 4140 |
| agggaaacga actggccctg ccctccaaat atgtgaactt cctgtacctg gccagccact | 4200 |
| atgagaagct gaagggctcc cccgaggata tgagcagaa acagctgttt gtggaacagc | 4260 |
| acaagcacta cctggacgag atcatcgagc agatcagcga gttctccaag agagtgatcc | 4320 |
| tggccgacgc taatctggac aaagtgctgt ccgcctacaa caagcaccgg ataagccca | 4380 |
| tcagagagca ggccgagaat atcatccacc tgtttaccct gaccaatctg ggagcccctg | 4440 |
| ccgccttcaa gtactttgac accaccatcg accggaagag gtacaccagc accaaagagg | 4500 |
| tgctggacgc caccctgatc caccagagca tcaccggcct gtacgagaca cggatcgacc | 4560 |
| tgtctcagct gggaggcgac agccccaaga agaagagaaa ggtggaggcc agctaagaat | 4620 |
| tcgatctttt tccctctgcc aaaaattatg gggacatcat gaagcccctt gagcatctga | 4680 |
| cttctggcta ataaaggaaa tttattttca ttgcaatagt gtgttggaat ttttgtgtc | 4740 |
| tctcactcgg cggccgcagg aacccctagt gatggagttg gccactccct ctctgcgcgc | 4800 |
| tcgctcgctc actgaggccg ggcgaccaaa ggtcgcccga cgcccgggct ttgcccgggc | 4860 |
| ggcctcagtg agcgagcgag cgcgcagctg cctgcagg | 4898 |

<210> SEQ ID NO 8
<211> LENGTH: 1399
<212> TYPE: PRT
<213> ORGANISM: Artificial Sequence
<220> FEATURE:
<223> OTHER INFORMATION: Synthetic Polypeptide

<400> SEQUENCE: 8

Met Tyr Pro Tyr Asp Val Pro Asp Tyr Ala Ser Pro Lys Lys Lys Arg
1               5                   10                  15

Lys Val Glu Ala Ser Asp Lys Lys Tyr Ser Ile Gly Leu Asp Ile Gly
            20                  25                  30

Thr Asn Ser Val Gly Trp Ala Val Ile Thr Asp Glu Tyr Lys Val Pro
        35                  40                  45

Ser Lys Lys Phe Lys Val Leu Gly Asn Thr Asp Arg His Ser Ile Lys
    50                  55                  60

```
Lys Asn Leu Ile Gly Ala Leu Leu Phe Asp Ser Gly Glu Thr Ala Glu
 65                  70                  75                  80

Ala Thr Arg Leu Lys Arg Thr Ala Arg Arg Arg Tyr Thr Arg Arg Lys
                 85                  90                  95

Asn Arg Ile Cys Tyr Leu Gln Glu Ile Phe Ser Asn Glu Met Ala Lys
            100                 105                 110

Val Asp Asp Ser Phe Phe His Arg Leu Glu Glu Ser Phe Leu Val Glu
        115                 120                 125

Glu Asp Lys Lys His Glu Arg His Pro Ile Phe Gly Asn Ile Val Asp
    130                 135                 140

Glu Val Ala Tyr His Glu Lys Tyr Pro Thr Ile Tyr His Leu Arg Lys
145                 150                 155                 160

Lys Leu Val Asp Ser Thr Asp Lys Ala Asp Leu Arg Leu Ile Tyr Leu
                165                 170                 175

Ala Leu Ala His Met Ile Lys Phe Arg Gly His Phe Leu Ile Glu Gly
            180                 185                 190

Asp Leu Asn Pro Asp Asn Ser Asp Val Asp Lys Leu Phe Ile Gln Leu
        195                 200                 205

Val Gln Thr Tyr Asn Gln Leu Phe Glu Glu Asn Pro Ile Asn Ala Ser
    210                 215                 220

Gly Val Asp Ala Lys Ala Ile Leu Ser Ala Arg Leu Ser Lys Ser Arg
225                 230                 235                 240

Arg Leu Glu Asn Leu Ile Ala Gln Leu Pro Gly Glu Lys Lys Asn Gly
                245                 250                 255

Leu Phe Gly Asn Leu Ile Ala Leu Ser Leu Gly Leu Thr Pro Asn Phe
            260                 265                 270

Lys Ser Asn Phe Asp Leu Ala Glu Asp Ala Lys Leu Gln Leu Ser Lys
        275                 280                 285

Asp Thr Tyr Asp Asp Asp Leu Asp Asn Leu Leu Ala Gln Ile Gly Asp
    290                 295                 300

Gln Tyr Ala Asp Leu Phe Leu Ala Ala Lys Asn Leu Ser Asp Ala Ile
305                 310                 315                 320

Leu Leu Ser Asp Ile Leu Arg Val Asn Thr Glu Ile Thr Lys Ala Pro
                325                 330                 335

Leu Ser Ala Ser Met Ile Lys Arg Tyr Asp Glu His His Gln Asp Leu
            340                 345                 350

Thr Leu Leu Lys Ala Leu Val Arg Gln Gln Leu Pro Glu Lys Tyr Lys
        355                 360                 365

Glu Ile Phe Phe Asp Gln Ser Lys Asn Gly Tyr Ala Gly Tyr Ile Asp
    370                 375                 380

Gly Gly Ala Ser Gln Glu Glu Phe Tyr Lys Phe Ile Lys Pro Ile Leu
385                 390                 395                 400

Glu Lys Met Asp Gly Thr Glu Glu Leu Leu Val Lys Leu Asn Arg Glu
                405                 410                 415

Asp Leu Leu Arg Lys Gln Arg Thr Phe Asp Asn Gly Ser Ile Pro His
            420                 425                 430

Gln Ile His Leu Gly Glu Leu His Ala Ile Leu Arg Arg Gln Glu Asp
        435                 440                 445

Phe Tyr Pro Phe Leu Lys Asp Asn Arg Glu Lys Ile Glu Lys Ile Leu
    450                 455                 460

Thr Phe Arg Ile Pro Tyr Tyr Val Gly Pro Leu Ala Arg Gly Asn Ser
465                 470                 475                 480
```

```
Arg Phe Ala Trp Met Thr Arg Lys Ser Glu Glu Thr Ile Thr Pro Trp
                485                 490                 495
Asn Phe Glu Glu Val Val Asp Lys Gly Ala Ser Ala Gln Ser Phe Ile
            500                 505                 510
Glu Arg Met Thr Asn Phe Asp Lys Asn Leu Pro Asn Glu Lys Val Leu
        515                 520                 525
Pro Lys His Ser Leu Leu Tyr Glu Tyr Phe Thr Val Tyr Asn Glu Leu
    530                 535                 540
Thr Lys Val Lys Tyr Val Thr Glu Gly Met Arg Lys Pro Ala Phe Leu
545                 550                 555                 560
Ser Gly Glu Gln Lys Lys Ala Ile Val Asp Leu Leu Phe Lys Thr Asn
                565                 570                 575
Arg Lys Val Thr Val Lys Gln Leu Lys Glu Asp Tyr Phe Lys Lys Ile
            580                 585                 590
Glu Cys Phe Asp Ser Val Glu Ile Ser Gly Val Glu Asp Arg Phe Asn
        595                 600                 605
Ala Ser Leu Gly Thr Tyr His Asp Leu Leu Lys Ile Ile Lys Asp Lys
    610                 615                 620
Asp Phe Leu Asp Asn Glu Glu Asn Glu Asp Ile Leu Glu Asp Ile Val
625                 630                 635                 640
Leu Thr Leu Thr Leu Phe Glu Asp Arg Glu Met Ile Glu Glu Arg Leu
                645                 650                 655
Lys Thr Tyr Ala His Leu Phe Asp Asp Lys Val Met Lys Gln Leu Lys
            660                 665                 670
Arg Arg Arg Tyr Thr Gly Trp Gly Arg Leu Ser Arg Lys Leu Ile Asn
        675                 680                 685
Gly Ile Arg Asp Lys Gln Ser Gly Lys Thr Ile Leu Asp Phe Leu Lys
    690                 695                 700
Ser Asp Gly Phe Ala Asn Arg Asn Phe Met Gln Leu Ile His Asp Asp
705                 710                 715                 720
Ser Leu Thr Phe Lys Glu Asp Ile Gln Lys Ala Gln Val Ser Gly Gln
                725                 730                 735
Gly Asp Ser Leu His Glu His Ile Ala Asn Leu Ala Gly Ser Pro Ala
            740                 745                 750
Ile Lys Lys Gly Ile Leu Gln Thr Val Lys Val Val Asp Glu Leu Val
    755                 760                 765
Lys Val Met Gly Arg His Lys Pro Glu Asn Ile Val Ile Glu Met Ala
770                 775                 780
Arg Glu Asn Gln Thr Thr Gln Lys Gly Gln Lys Asn Ser Arg Glu Arg
785                 790                 795                 800
Met Lys Arg Ile Glu Glu Gly Ile Lys Glu Leu Gly Ser Gln Ile Leu
                805                 810                 815
Lys Glu His Pro Val Glu Asn Thr Gln Leu Gln Asn Glu Lys Leu Tyr
            820                 825                 830
Leu Tyr Tyr Leu Gln Asn Gly Arg Asp Met Tyr Val Asp Gln Glu Leu
        835                 840                 845
Asp Ile Asn Arg Leu Ser Asp Tyr Asp Val Asp His Ile Val Pro Gln
    850                 855                 860
Ser Phe Leu Lys Asp Asp Ser Ile Asp Asn Lys Val Leu Thr Arg Ser
865                 870                 875                 880
Asp Lys Asn Arg Gly Lys Ser Asp Asn Val Pro Ser Glu Glu Val Val
                885                 890                 895
Lys Lys Met Lys Asn Tyr Trp Arg Gln Leu Leu Asn Ala Lys Leu Ile
```

-continued

```
                900             905             910
Thr Gln Arg Lys Phe Asp Asn Leu Thr Lys Ala Glu Arg Gly Gly Leu
            915             920             925
Ser Glu Leu Asp Lys Ala Gly Phe Ile Lys Arg Gln Leu Val Glu Thr
            930             935             940
Arg Gln Ile Thr Lys His Val Ala Gln Ile Leu Asp Ser Arg Met Asn
945             950             955             960
Thr Lys Tyr Asp Glu Asn Asp Lys Leu Ile Arg Glu Val Lys Val Ile
            965             970             975
Thr Leu Lys Ser Lys Leu Val Ser Asp Phe Arg Lys Asp Phe Gln Phe
            980             985             990
Tyr Lys Val Arg Glu Ile Asn Asn Tyr His His Ala His Asp Ala Tyr
            995             1000            1005
Leu Asn Ala Val Val Gly Thr Ala Leu Ile Lys Lys Tyr Pro Lys
        1010            1015            1020
Leu Glu Ser Glu Phe Val Tyr Gly Asp Tyr Lys Val Tyr Asp Val
        1025            1030            1035
Arg Lys Met Ile Ala Lys Ser Glu Gln Glu Ile Gly Lys Ala Thr
        1040            1045            1050
Ala Lys Tyr Phe Phe Tyr Ser Asn Ile Met Asn Phe Phe Lys Thr
        1055            1060            1065
Glu Ile Thr Leu Ala Asn Gly Glu Ile Arg Lys Arg Pro Leu Ile
        1070            1075            1080
Glu Thr Asn Gly Glu Thr Gly Glu Ile Val Trp Asp Lys Gly Arg
        1085            1090            1095
Asp Phe Ala Thr Val Arg Lys Val Leu Ser Met Pro Gln Val Asn
        1100            1105            1110
Ile Val Lys Lys Thr Glu Val Gln Thr Gly Gly Phe Ser Lys Glu
        1115            1120            1125
Ser Ile Leu Pro Lys Arg Asn Ser Asp Lys Leu Ile Ala Arg Lys
        1130            1135            1140
Lys Asp Trp Asp Pro Lys Lys Tyr Gly Gly Phe Asp Ser Pro Thr
        1145            1150            1155
Val Ala Tyr Ser Val Leu Val Val Ala Lys Val Glu Lys Gly Lys
        1160            1165            1170
Ser Lys Lys Leu Lys Ser Val Lys Glu Leu Leu Gly Ile Thr Ile
        1175            1180            1185
Met Glu Arg Ser Ser Phe Glu Lys Asn Pro Ile Asp Phe Leu Glu
        1190            1195            1200
Ala Lys Gly Tyr Lys Glu Val Lys Lys Asp Leu Ile Ile Lys Leu
        1205            1210            1215
Pro Lys Tyr Ser Leu Phe Glu Leu Glu Asn Gly Arg Lys Arg Met
        1220            1225            1230
Leu Ala Ser Ala Gly Glu Leu Gln Lys Gly Asn Glu Leu Ala Leu
        1235            1240            1245
Pro Ser Lys Tyr Val Asn Phe Leu Tyr Leu Ala Ser His Tyr Glu
        1250            1255            1260
Lys Leu Lys Gly Ser Pro Glu Asp Asn Glu Gln Lys Gln Leu Phe
        1265            1270            1275
Val Glu Gln His Lys His Tyr Leu Asp Glu Ile Ile Glu Gln Ile
        1280            1285            1290
Ser Glu Phe Ser Lys Arg Val Ile Leu Ala Asp Ala Asn Leu Asp
        1295            1300            1305
```

```
Lys Val Leu Ser Ala Tyr Asn Lys His Arg Asp Lys Pro Ile Arg
    1310            1315                1320

Glu Gln Ala Glu Asn Ile Ile His Leu Phe Thr Leu Thr Asn Leu
    1325            1330                1335

Gly Ala Pro Ala Ala Phe Lys Tyr Phe Asp Thr Thr Ile Asp Arg
    1340            1345                1350

Lys Arg Tyr Thr Ser Thr Lys Glu Val Leu Asp Ala Thr Leu Ile
    1355            1360                1365

His Gln Ser Ile Thr Gly Leu Tyr Glu Thr Arg Ile Asp Leu Ser
    1370            1375                1380

Gln Leu Gly Gly Asp Ser Pro Lys Lys Lys Arg Lys Val Glu Ala
    1385            1390                1395

Ser

<210> SEQ ID NO 9
<211> LENGTH: 2323
<212> TYPE: DNA
<213> ORGANISM: Artificial Sequence
<220> FEATURE:
<223> OTHER INFORMATION: Synthetic Polynucleotide

<400> SEQUENCE: 9
ctgcgcgctc gctcgctcac tgaggccgcc cgggcaaagc ccgggcgtcg ggcgaccttt      60
ggtcgcccgg cctcagtgag cgagcgagcg cgcagagagg gagtgtagcc atgctctagg     120
aagatcaatt cggtacaatt cacgcgtgag ggcctatttc ccatgattcc ttcatatttg     180
catatacgat acaaggctgt tagagagata attggaatta atttgactgt aaacacaaag     240
atattagtac aaaatacgtg acgtagaaag taataatttc ttgggtagtt tgcagtttta     300
aaattatgtt ttaaaatgga ctatcatatg cttaccgtaa cttgaaagta tttcgatttc     360
ttggctttat atatcttgtg aaaggacgaa acaccgaac ttcatgggtt tcaactggtt     420
ttagagctag aaatagcaag ttaaaataag gctagtccgt tatcaacttg aaaaagtggc     480
accgagtcgg tgcttttta cgcgtcgaca ttgattattg actagttatt aatagtaatc     540
aattacgggg tcattagttc atagcccata tatggagttc cgcgttacat aacttacggt     600
aaatggcccg cctggctgac cgcccaacga ccccgccca ttgacgtcaa taatgacgta     660
tgttcccata gtaacgccaa tagggacttt ccattgacgt caatgggtgg agtatttacg     720
gtaaactgcc cacttggcag tacatcaagt gtatcatatg ccaagtacgc cccctattga     780
cgtcaatgac ggtaaatggc ccgcctggca ttatgcccag tacatgacct tatgggactt     840
tcctacttgg cagtacatct acgtattagt catcgctatt accatgtcga ggccacgttc     900
tgcttcactc tccccatctc ccccccctcc caccccaa ttttgtattt atttattttt     960
taattatttt gtgcagcgat ggggggcgggg ggggggggcg cgcgccaggc ggggcggggc    1020
ggggcgaggg gcggggcggg gcgaggcgga gaggtgcggc ggcagccaat cagagcggcg    1080
cgctccgaaa gtttcctttt atggcgaggc ggcggcggcg gcggccctat aaaaagcgaa    1140
gcgcgcggcg gcgggagca agctctagcc tcgagaatta cttaatacga ctcactatag    1200
gctagtaata cgactcacta tagatggtga gcaagggcga ggagctgttc accgggtgg    1260 tgcccatcct ggtcgagctg gacggcgacg taaacggcca agttcagc gtgtccggcg    1320 agggcgaggg cgatgccacc tacggcaagc tgaccctgaa gttcatctgc accaccggca    1380
agctgcccgt gccctggccc accctcgtga ccaccctgac ctacggcgtg cagtgcttca    1440
```

```
gccgctaccc cgaccacatg aagcagcacg acttcttcaa gtccgccatg cccgaaggct    1500
acgtccagga gcgcaccatc ttcttcaagg acgacggcaa ctacaagacc cgcgccgagg    1560
tgaagttcga gggcgacacc ctggtgaacc gcatcgagct gaagggcatc gacttcaagg    1620
aggacggcaa catcctgggg cacaagctgg agtacaacta caacagccac aacgtctata    1680
tcatggccga caagcagaag aacggcatca aggtgaactt caagatccgc cacaacatcg    1740
aggacggcag cgtgcagctc gccgaccact accagcagaa cacccccatc ggcgacggcc    1800
ccgtgctgct gcccgacaac cactacctga gcacccagtc cgccctgagc aaagacccca    1860
acgagaagcg cgatcacatg gtcctgctgg agttcgtgac cgccgccggg atcactctcg    1920
gcatggacga gctgtacaag taaagcggcc ctagcgttta acgggccct ctagagtcga    1980 cccgggcggc ctcgaggacg gggtgaacta cgcctgagga tccgatcttt ttccctctgc    2040
caaaaattat ggggacatca tgaagcccct tgagcatctg acttctggct aataaaggaa    2100
atttattttc attgcaatag tgtgttggaa ttttttgtgt ctctcactcg gcctaggtag    2160
ataagtagca tggcgggtta atcattaact acaaggaacc cctagtgatg gagttggcca    2220
ctccctctct gcgcgctcgc tcgctcactg aggccgggcg accaaaggtc gcccgacgcc    2280
cgggctttgc ccgggcggcc tcagtgagcg agcgagcgcg cag                      2323
```

<210> SEQ ID NO 10
<211> LENGTH: 239
<212> TYPE: PRT
<213> ORGANISM: Artificial Sequence
<220> FEATURE:
<223> OTHER INFORMATION: Synthetic Polypeptide

<400> SEQUENCE: 10

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205
```

```
Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 11
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 11
ttgttggcaa aagaatgctg                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 12
gcttcatggg caaaatcaat                                              20

<210> SEQ ID NO 13
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 13
tgaagcagtt caccaaaata ac                                           22

<210> SEQ ID NO 14
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 14
ctgtttgaga gtcagcaacg                                              20

<210> SEQ ID NO 15
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 15
tgaagcagtt caccaaaata ac                                           22

<210> SEQ ID NO 16
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 16
gcgagctgat taaggagaac                                              20

```
<210> SEQ ID NO 17
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 17
gctaagaacc tcaagatgcc                                                  20

<210> SEQ ID NO 18
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 18
cgttgctgac tctcaaacag                                                  20

<210> SEQ ID NO 19
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 19
acccctgtgt gatagaccac                                                  20

<210> SEQ ID NO 20
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 20
catgggctgc tatttgtggc                                                  20

<210> SEQ ID NO 21
<211> LENGTH: 30
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Modified by /5Biosg/

<400> SEQUENCE: 21
cttgagcatc tgacttctgg ctaataaagg                                       30

<210> SEQ ID NO 22
<211> LENGTH: 37
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(16)
<223> OTHER INFORMATION: n is a, c, g, or t

<400> SEQUENCE: 22
nnnnnnnnnn nnnnnnagga acccctagtg atggagt                               37
```

<210> SEQ ID NO 23
<211> LENGTH: 35
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(16)
<223> OTHER INFORMATION: n is a, c, g, or t

<400> SEQUENCE: 23
nnnnnnnnnn nnnnnnacta tagggcacgc gtggt              35

<210> SEQ ID NO 24
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 24
tggccactcc              10

<210> SEQ ID NO 25
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 25
aacttcatgg gtttcaactg cgga              24

<210> SEQ ID NO 26
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 26
aacttcatgg gtttcaactg ctga              24

<210> SEQ ID NO 27
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 27

Asn Phe Met Gly Phe Asn Cys
1               5

<210> SEQ ID NO 28
<211> LENGTH: 524
<212> TYPE: DNA
<213> ORGANISM: Artificial Sequence
<220> FEATURE:
<223> OTHER INFORMATION: Synthetic Polynucleotide

<400> SEQUENCE: 28
ttgttggcaa aagaatgctg cccaccatgg atgggtgatg ggagtccctg cggccagctt       60
tcaggcagag gttcctgcca ggatatcctt ctgtccagtg caccatctgg acctcagttc      120

```
cccttcaaag gggtggatga ccgtgagtcc tggccctctg tgttttataa taggacctgc    180
cagtgctcag gcaacttcat gggtttcaac tgcggaaact gtaagtttgg atttgggggc    240
ccaaattgta cagagaagcg agtcttgatt agaagaaaca ttttttgattt gagtgtctcc   300 gaaaagaata agttcttttc ttacctcact ttagcaaaac atactatcag ctcagtctat    360
gtcatcccca caggcaccta tggccaaatg aacaatgggt caacacccat gtttaatgat    420
atcaacatct acgacctctt tgtatggatg cattactatg tgtcaaggga cacactgctt    480
gggggctctg aaatatggag ggacattgat tttgcccatg aagc                    524
```

```
<210> SEQ ID NO 29
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 29
tcagttcccc ttcaaggggg tgg                                              23

<210> SEQ ID NO 30
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 30
ggtcctatta taaaacacag agg                                              23

<210> SEQ ID NO 31
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 31
ggtcatccac ccctttgaag ggg                                              23

<210> SEQ ID NO 32
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 32
aacttcatgg gtttcaactg cgg                                              23

<210> SEQ ID NO 33
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 33
gggtggatga ccgtgagtcc tgg                                              23

<210> SEQ ID NO 34
<211> LENGTH: 11
<212> TYPE: DNA
<213> ORGANISM: Artificial Sequence
```

```
<220> FEATURE:
<223> OTHER INFORMATION: Synthetic Polynucleotide

<400> SEQUENCE: 34
cctggccctc t                                                            11

<210> SEQ ID NO 35
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 35
gggtttcaac tgcggaaa                                                     18

<210> SEQ ID NO 36
<211> LENGTH: 9
<212> TYPE: DNA
<213> ORGANISM: Artificial Sequence
<220> FEATURE:
<223> OTHER INFORMATION: Synthetic Polynucleotide

<400> SEQUENCE: 36 cccaaattg                                                                9

<210> SEQ ID NO 37
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 37
gcgctctgtg tgcagcttgt tggcaaaaga atgctg                                 36

<210> SEQ ID NO 38
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 38
tcatgagtcg acactattgt tggcaaaaga atgctg                                 36

<210> SEQ ID NO 39
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 39
tatctatcgt atacgcttgt tggcaaaaga atgctg                                 36

<210> SEQ ID NO 40
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 40
atcacactgc atctgattgt tggcaaaaga atgctg                                 36
```

<210> SEQ ID NO 41
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 41
acgtacgctc gtcatattgt tggcaaaaga atgctg                                 36

<210> SEQ ID NO 42
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 42
tgtgagtcag tacgcgttgt tggcaaaaga atgctg                                 36

<210> SEQ ID NO 43
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 43
agagacacga tactcattgt tggcaaaaga atgctg                                 36

<210> SEQ ID NO 44
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 44
ctgctagagt ctacagttgt tggcaaaaga atgctg                                 36

<210> SEQ ID NO 45
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 45
agcactcgcg tcagtgttgt tggcaaaaga atgctg                                 36

<210> SEQ ID NO 46
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 46
tcatgcacgt ctcgctttgt tggcaaaaga atgctg                                 36

<210> SEQ ID NO 47
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 47
agagcatctc tgtactttgt tggcaaaaga atgctg                                    36

<210> SEQ ID NO 48
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 48
cgcatcgact acgctattgt tggcaaaaga atgctg                                    36

<210> SEQ ID NO 49
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 49
agagtactac atatgagctt catgggcaaa atcaat                                    36

<210> SEQ ID NO 50
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 50
cgtgtgcata gatcgcgctt catgggcaaa atcaat                                    36

<210> SEQ ID NO 51
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 51
atgtatctcg actgcagctt catgggcaaa atcaat                                    36

<210> SEQ ID NO 52
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 52
gactcgacgc agagtcgctt catgggcaaa atcaat                                    36

<210> SEQ ID NO 53
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 53
cgatgacgtc gctgtagctt catgggcaaa atcaat                                    36

<210> SEQ ID NO 54

<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 54
cacacgtagt ctgcgcgctt catgggcaaa atcaat                                36

<210> SEQ ID NO 55
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 55
gctgtatcgc agagacgctt catgggcaaa atcaat                                36

<210> SEQ ID NO 56
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 56
cgagctatct catactgctt catgggcaaa atcaat                                36

<210> SEQ ID NO 57
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 57
catgagtact cgtcgcgctt catgggcaaa atcaat                                36

<210> SEQ ID NO 58
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 58
cagcgactgt gatactgctt catgggcaaa atcaat                                36

<210> SEQ ID NO 59
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 59
tgtcgcatca tatgatgctt catgggcaaa atcaat                                36

<210> SEQ ID NO 60
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 60
gctgtgatct acgtctgctt catgggcaaa atcaat                                36

<210> SEQ ID NO 61
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 61
gcgctctgtg tgcagc                                                      16

<210> SEQ ID NO 62
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 62
tcatgagtcg acacta                                                      16

<210> SEQ ID NO 63
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 63
tatctatcgt atacgc                                                      16

<210> SEQ ID NO 64
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 64
atcacactgc atctga                                                      16

<210> SEQ ID NO 65
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 65
acgtacgctc gtcata                                                      16

<210> SEQ ID NO 66
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 66
tgtgagtcag tacgcg                                                      16

<210> SEQ ID NO 67
<211> LENGTH: 16
<212> TYPE: DNA

```
<213> ORGANISM: Artificial Sequence
<220> FEATURE:
<223> OTHER INFORMATION: Synthetic Polynucleotide

<400> SEQUENCE: 67
agagacacga tactca                                                    16

<210> SEQ ID NO 68
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 68
ctgctagagt ctacag                                                    16

<210> SEQ ID NO 69
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 69
agcactcgcg tcagtg                                                    16

<210> SEQ ID NO 70
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 70
tcatgcacgt ctcgct                                                    16

<210> SEQ ID NO 71
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 71
agagcatctc tgtact                                                    16

<210> SEQ ID NO 72
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 72
cgcatcgact acgcta                                                    16

<210> SEQ ID NO 73
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 73
agagtactac atatga                                                    16
```

```
<210> SEQ ID NO 74
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 74
cgtgtgcata gatcgc                                                        16

<210> SEQ ID NO 75
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 75
atgtatctcg actgca                                                        16

<210> SEQ ID NO 76
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 76
gactcgacgc agagtc                                                        16

<210> SEQ ID NO 77
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 77
cgatgacgtc gctgta                                                        16

<210> SEQ ID NO 78
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 78
cacacgtagt ctgcgc                                                        16

<210> SEQ ID NO 79
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 79
gctgtatcgc agagac                                                        16

<210> SEQ ID NO 80
<211> LENGTH: 16
<212> TYPE: DNA
<213> ORGANISM: Artificial Sequence
<220> FEATURE:
```

<223> OTHER INFORMATION: Synthetic Polynucleotide

<400> SEQUENCE: 80
cgagctatct catact                                                    16

<210> SEQ ID NO 81
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 81
catgagtact cgtcgc                                                    16

<210> SEQ ID NO 82
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 82
cagcgactgt gatact                                                    16

<210> SEQ ID NO 83
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 83
tgtcgcatca tatgat                                                    16

<210> SEQ ID NO 84
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 84
gctgtgatct acgtct                                                    16

<210> SEQ ID NO 85
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 85
gctcaggcaa cttcatgggt ttcaactgcg aaactgtaa gtttggattt                 50

<210> SEQ ID NO 86
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 86
gctcaggcaa cttcatgggt ttcaaactgc ggaaactgta agtttggatt t              51

```
<210> SEQ ID NO 87
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 87
gctcaggcaa cttcatgggt ttcaaaactg cggaaactgt aagtttggat tt          52

<210> SEQ ID NO 88
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 88
gctcaggcaa cttcatgggt ttcaaatctg cggaaactgt aagtttggat tt          52

<210> SEQ ID NO 89
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 89
gctcaggcaa cttcatgggt ttcaatctgc ggaaactgta agtttggatt t           51

<210> SEQ ID NO 90
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 90
gctcaggcaa cttcatgggt ttctgcggaa actgtaagtt tggattt               47

<210> SEQ ID NO 91
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 91
gctcaggcaa cttcatgggt ttctgcggaa actgtaagtt tggattt               47

<210> SEQ ID NO 92
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 92
gctcaggcaa cttcatgggt ttcctgcgga aactgtaagt ttggattt              48

<210> SEQ ID NO 93
<211> LENGTH: 48
<212> TYPE: DNA
<213> ORGANISM: Artificial Sequence
<220> FEATURE:
<223> OTHER INFORMATION: Synthetic Polynucleotide
```

<400> SEQUENCE: 93
gctcaggcaa cttcatgggt ttcatgcgga aactgtaagt ttggattt            48

<210> SEQ ID NO 94
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 94
gctcaggcaa cttcatgggt ttcactgcgg aaactgtaag tttggattt           49

<210> SEQ ID NO 95
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 95
gctcaggcaa cttcatgggt ttcaatgcgg aaactgtaag tttggattt           49

<210> SEQ ID NO 96
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 96
gctcaggcaa cttcatgggt ttcaactgga aactgtaagt ttggattt            48

<210> SEQ ID NO 97
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 97
gctcaggcaa cttcatgggt ttcatctgcg gaaactgtaa gtttggattt          50

<210> SEQ ID NO 98
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 98
gcggaaactg taagtttgga ttt                                       23

<210> SEQ ID NO 99
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 99
gctcaggcaa cttcatgggt ttactgcgga aactgtaagt ttggattt            48

<210> SEQ ID NO 100
<211> LENGTH: 49

<210> SEQ ID NO 100
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 100
gctcaggcaa cttcatgggt ttctctgcgg aaactgtaag tttggattt         49

<210> SEQ ID NO 101
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 101
gctcaggcaa cttcatgggt ttcattggaa actgtaagtt tggattt           47

<210> SEQ ID NO 102
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 102
gctcaggcaa cttcatgggt ttcaatgaaa ctgtaagttt ggattt            46

<210> SEQ ID NO 103
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 103
gctcaggcaa cttcatgggt ttcaatggaa actgtaagtt tggattt           47

<210> SEQ ID NO 104
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 104
gctcaggcaa cttcatgggt ttcatggaaa ctgtaagttt ggattt            46

<210> SEQ ID NO 105
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 105
gctcaggcaa cttcatgggt ttcatctgga aactgtaagt ttggattt          48

<210> SEQ ID NO 106
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 106

```
gggcgtcggg cgacctttgg aaactgcgga aa                                    32

<210> SEQ ID NO 107
<211> LENGTH: 145
<212> TYPE: DNA
<213> ORGANISM: Artificial Sequence
<220> FEATURE:
<223> OTHER INFORMATION: Synthetic Polynucleotide

<400> SEQUENCE: 107
aggaacccct agtgatggag ttggccactc cctctctgcg cgctcgctcg ctcactgagg      60
ccgcccgggc aaagcccggg cgtcgggcga cctttggtcg cccggcctca gtgagcgagc     120
gagcgcgcag agagggagtg gccaa                                          145

<210> SEQ ID NO 108
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 108
aggcaacttc atgggtttca actgcggaaa ctgtaagt                              38
```

RECOMBINANT ADENO-ASSOCIATED VIRUSES FOR DELIVERING GENE EDITING MOLECULES TO EMBRYONIC CELLS

CROSS-REFERENCE TO RELATED APPLICATION

This application claims the benefit of the filing date of U.S. Provisional Application No. 62/350,358, entitled "STREAMLINED GENE EDITING OF MOUSE EMBRYOS IN EXPLANT CULTURE AND IN VIVO USING RECOMBINANT ADENO-ASSOCIATED VIRUSES," filed Jun. 15, 2017, the contents of which are incorporated herein by reference in its entirety.

STATEMENT OF FEDERALLY SPONSORED RESEARCH

This invention was made with government support under Grant Nos. HD083311, HD089566, 1P01AI100263-01, and 2R01NS076991-0 awarded by the National Institutes of Health. The government has certain rights in the invention.

BACKGROUND

The generation of mice harboring single-gene modifications has traditionally involved on gene targeting in embryonic stem cells, blastocyst microinjection, and germline transmission through chimera intermediates. Although recent advances using CRISPR-Cas9 approaches have dramatically enhanced the ease for genetic manipulation, the generation of transgenic animals (e.g., transgenic mice) still depends on embryo microinjection or electroporation techniques that are laborious and time consuming. Accordingly, new methods and compositions for the generation of transgenic animals (e.g., transgenic mice) are needed.

SUMMARY

Aspects of the disclosure relate to methods for administering molecules to pre-implantation embryos. In some embodiments, methods provided herein involve delivering gene editing molecules (e.g., Cas 9 or related enzymes) into cells of pre-implantation embryos. The present disclosure is based in part on the discovery that recombinant adeno-associated viruses (rAAVs) comprising transgenes encoding gene editing molecules (e.g., Cas 9) can be used to transduce cells of a pre-implantation embryo without the need to remove the zona pellucida, thereby facilitating gene editing in the embryonic cells. In some embodiments, it has been shown that rAAVs can permeate the zona pellucida to transduce pre-implantation embryos. In some embodiments, intact morulae were treated with a range of different rAAV serotypes, all of which were capable of transducing intact morulae. Accordingly, in some embodiments, methods are provided for delivering nucleic acids engineered to express one or more components of a gene editing complex using rAAVs. However, in some embodiments, methods are provided for delivering nucleic acids engineered to express any useful gene product in embryonic cells.

Accordingly, one aspect of the present disclosure provides a method for delivering gene editing molecules to cells of a pre-implantation embryo. In some embodiments, the methods involve contacting the pre-implantation embryo with a recombinant adeno-associated virus (rAAV) having a capsid harboring a nucleic acid comprising a promoter operably linked to a transgene encoding a gene editing molecule.

In some embodiments, the pre-implantation embryo comprises one or more cells. In some embodiments, the pre-implantation embryo is a mammalian pre-implantation embryo. In some embodiments, the pre-implantation embryo is at a zygote, morula, or pre-implantation blastocyst stage. In some embodiments, the pre-implantation embryo is at a one-cell stage, two-cell stage, four-cell stage, or eight-cell stage. In some embodiments, the pre-implantation embryo comprises an intact zona pellucida. In some embodiments, the pre-implantation embryo is in vitro. In some embodiments, the pre-implantation embryo is located within a subject, optionally wherein the subject is a mammal. In some embodiments, the pre-implantation embryo is located in the oviduct of the subject. In some embodiments, the pre-implantation embryo is located in the ampulla of the oviduct.

In some embodiments, the capsid comprises a capsid protein of a serotype selected from: AAV1, AAV2, AAV3b, AAV4, AAV5, AAV6, AAV6.2, AAV7, AAV8, AAV9, AAV.rh39, AAVrh.43, AAVrh.8, and AAVrh.10. In some embodiments, the capsid protein comprises an amino acid sequence that is at least 70%, at least 80%, at least 90%, at least 95%, or at least 99% identical to SEQ ID NO: 1. In some embodiments, the capsid protein is an AAV6 capsid protein having a sequence as set forth in SEQ ID NO: 1.

In some embodiments, the gene editing molecule is a nuclease or a recombinase. In some embodiments, the nuclease is a Transcription Activator-like Effector Nuclease (TALEN), Zinc Finger Nuclease (ZFN), or a CRISPR/Cas-associated protein. In some embodiments, the CRISPR/Cas-associated protein is Cas9, Cas6, dCas9, or Cpf1. In some embodiments, the recombinase is Cre, FLP, R, IntA, Tn3 resolvase, Hin invertase, or Gin invertase. In some embodiments, the recombinase is Cre recombinase, and cells of the pre-implantation embryo comprises at least one genomic location having a LoxP site. In some embodiments, the gene editing molecule is an engineered guide RNA.

In another aspect, the present disclosure provides a method of delivering a transgene across the zona pellucida of a pre-implantation embryo. In some embodiments, the methods involve contacting the pre-implantation embryo with a recombinant adeno-associated virus (rAAV) having a capsid housing a nucleic acid comprising a promoter operably linked to a transgene.

Alternatively or in addition to, the present disclosure provides a method for facilitating genome editing in cells of a pre-implantation embryo. In some embodiments, the methods involve contacting a pre-implantation embryo with a first rAAV comprising a capsid harboring a nucleic acid comprising a promoter operably linked to a transgene encoding a guide RNA. In some embodiments, the methods involve contacting a pre-implantation embryo with a second rAAV comprising a capsid harboring a nucleic acid comprising a promoter operably linked to a transgene encoding a CRISPR/Cas-associated protein.

In yet another embodiment, the present disclosure provides compositions and kits for administering molecules to pre-implantation embryos. In some embodiments, the present disclosure provides a transgenic animal produced by methods disclosed herein. In some embodiments, the present disclosure provides a kit for producing an isolated recombinant adeno-associated virus (rAAV) for genome editing in a pre-implantation embryonic cell, comprising at least one container housing a rAAV vector, wherein the rAAV comprises at least one capsid protein, and a nucleic acid comprising a promoter operably linked to a transgene encoding a gene editing molecule, at least one container housing a rAAV packaging component, and instructions for constructing and packaging the rAAV, wherein the rAAV transduces a pre-implantation embryonic cell. In some embodiments, the present disclosure provides a recombinant adeno-associated virus (rAAV) comprising an AAV capsid protein having a sequence as set forth in SEQ ID NO: 1, and a nucleic acid engineered to express a gene editing molecule.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1A shows a schematic representation of the strategy to transduce C57BL/6NJ zygotes with rAAV vectors designed to target the Tyrosinase (Tyr) locus. Zygotes were placed in KSOM containing rAAV6-Cas9 and rAAV6-sgTyr vectors, rinsed, cultured at 37° C. for 3 days and analyzed for Tyr gene editing at compacted morula or blastocyst stages. Alternatively, they were cultured overnight and transferred at the 2-cell stage into the oviducts of E0.5 pseudo-pregnant females. Transferred embryos were assessed for eye pigmentation at E16.5, or allowed to develop to birth and assessed for eye and coat color pigmentation. FIG. 1B shows a stacked histogram showing the percentage distribution of indel-type frequencies among four rAAV-dosage groups (6E+9, 6E+7, 6E+6 GCs, and non-treated). Alterations indicate base replacements; Large Deletions are defined as removal of >20 bases and compound mutations are combinations of insertions, deletions, and/or alterations. FIG. 1C shows an analysis of eye pigmentation in E16.5 embryos transduced with rAAV6-Cas9 only (left panel) and both rAAV6-Cas9 and rAAV6-sgTyr (right panel). Arrow in the right panel indicates the location of the eye in a transduced albino embryo. FIG. 1D shows an albino litter generated after transduction of C57BL/6NJ zygotes with CRISPR-Cas9 rAAV vectors at $6 \times 10^9$ GCs dose. Shaved area on female indicates site of embryo transfer surgery. FIG. 1E shows a litter obtained after transduction of C57BL/6NJ zygotes with CRISPR-Cas9 rAAV vectors at $6 \times 10^8$ GCs dose. Three out of five pups are albino and two are mosaic as revealed by the variegated coat color pattern. FIG. 1F shows a schematic representation of the strategy to test germline transmission of CRISPR-Cas9-induced alleles of Tyr. Tyr-edited albino mice were mated with albino CD-1 ($Tyr^{c/c}$) animals and the offspring were assessed for the presence of albino coat color. FIG. 1G shows a litter derived from Tyr-edited albino male crossed with a CD-1 female. All pups are albino indicating germline transmission.

FIGS. 2A-2F show homology-directed repair (HDR) mediated by recombinant AAV vectors. FIG. 2A shows a schematic representation of the Tyr locus and location of sgRNA in exon 1. The initiation and termination codons are indicated. The location of the sgRNA used to target Tyr is also indicated. The sequence corresponds to SEQ ID NO: 25. FIG. 2B shows a schematic representation of the strategy to introduce a premature stop codon in the Tyr locus using HDR. The 5' and 3' homology arms are marked by a thick line. The G to T nucleotide transversion in the PAM sequence converts a glycine codon (GGA) into a stop codon (TGA) disrupting translation of Tyr. The solid arrows indicate binding sites of the primers used in PCR-TOPO sequencing. The sequences correspond to SEQ ID NOs: 26 (nucleotide) and 27 (amino acid). FIG. 2C shows a schematic representation of the strategy to insert the blue fluorescent protein (BFP) gene into the Tyr locus using HDR. The solid arrows depict the binding sites of PCR primers used to confirm the insertion of BFP into Tyr locus. P2A, Porcine teschovirus-1 2A peptide; TAA, Stop codon. FIG. 2D shows results from an analysis of single nucleotide transversion in individual embryos or pups using PCR-TOPO sequencing. Each bar represents an individual sample. For pups, only DNA from tail snips and ear punches was analyzed. FIG. 2E shows results confirming BFP insertion using PCR. Four out of seven E3.5 embryos tested showed correct insertion of BFP into the Tyr locus. The left panel shows amplification of the 5'-junction of the targeted Tyr locus using a forward primer that binds to genomic DNA upstream of the homology region and a reverse primer that binds to the BFP gene as shown in FIG. 2C. The right panel shows amplification of the 3'-junction of the Tyr edited allele using a forward primer that binds to the BFP gene and a reverse primer that binds to genomic DNA downstream of the homology region. FIG. 2F shows a table showing the frequency of single nucleotide transversion and BFP insertion by HDR using two different doses of rAAV vectors.

FIGS. 3A-3F show in vivo genome editing by delivery of recombinant AAV vectors into the oviduct of pregnant females. FIG. 3A shows a schematic representation of the strategy to induce in vivo gene editing of the Tyr locus. rAAV vectors carrying SpCas9 and sgTyr expression constructs were injected directly into the oviduct of plugged C57BL/6NJ females mated to C57BL/6NJ males. FIG. 3B shows a close-up view of the reproductive tract showing the process of in vivo delivery of rAAVs into the ampulla of the oviduct. The rAAV injection solution contains a blue tracer dye that is visible at the tip of the glass micropipette. A small pool of the injected solution is evident inside the ampulla. U, uterus; Ov, oviduct; O, ovary. FIG. 3C shows a representative litter born after in vivo genome editing of Tyr. One out of eight pups born was albino. FIG. 3D shows a litter derived from Tyr-edited albino male crossed with a CD-1 female. All pups are albino indicating germline transmission. FIG. 3E shows a stacked histogram showing the percentage distribution of indel-type frequencies in two albino (1 and 2) and two black (3 and 4) pups by SMRT-sequencing. Three C57BL/6NJ control samples (C1-C3) were included in the analysis. Alterations indicate base replacements; compound mutations are combinations of insertions, deletions, and/or alterations. The yellow area in sample C3 is likely the product of sequencing error. FIG. 3F shows a table showing the frequency of Tyr indels in vivo.

FIG. 4A shows a schematic representation of the strategy to transduce 8-cell morulae with rAAVs. FIG. 4B shows analysis of compacted morulae or blastocysts transduced with individual rAAV serotypes. All rAAV serotypes show evidence of transduction as revealed by EGFP expression.

FIGS. 5A-5F show transduction of rAAV vectors into one-cell embryos can induce Cre-LoxP recombination. FIG. 5A shows a schematic representation of the strategy to induce Cre-LoxP recombination using rAAVs. $R26^{mTmG}$ heterozygous zygotes derived from breeding $R26^{mTmG}$ homozygous and wild-type animals were placed in a drop of KSOM media containing rAAV particles, rinsed, cultured in KSOM and analyzed for fluorescence after 3 days in culture or were transferred into pseudo-pregnant females after one day in culture and allowed to develop to term. FIG. 5B shows a schematic representation of the R26$^{mTmG}$ fluorescence reporter. R26$^{mTmG}$ carries a membrane-targeted tdTomato gene (mT) flanked by loxP sites, followed by membrane-targeted EGFP (mG). R26$^{mTmG}$ embryos fluoresce red. Cre-mediated recombination drives expression of mG, making recombined cells fluoresce green. FIG. 5C shows fluorescence analysis of compacted morulae transduced with rAAV6-Cre. Maternal mT protein is present in both non-treated (top row) and treated (bottom row) embryos, making them fluoresce red. Transduction with rAAV6-Cre leads to green fluorescent embryos (bottom row), indicative of Cre-mediated recombination. Inset is a merged image of the embryo marked by arrows to highlight mosaicism evident by the absence of green fluorescence in some cells. FIG. 5D shows fluorescence analysis of pups derived from zygotes transduced with rAAV6-Cre in culture and transferred into pseudo-pregnant females. Two pups show complete Cre-lox recombination (1 and 2), two are mosaic (3 and 4) and one (5) did not undergo recombination. FIG. 5E shows a schematic representation of the strategy to test for germline transmission of the recombined R26$^{mG}$ allele obtained after rAAV6-Cre treatment of R26$^{mTmG/+}$ zygotes in culture. FIG. 5F shows a R26$^{mG/+}$ mother and her offspring derived from a cross to a wild-type male; two R26$^{mG/+}$ pups are visible.

FIGS. 7A-7E show a strategy for Tyr gene editing using CRISPR-Cas9 and validation in cell culture. FIG. 7A shows schematic diagrams showing rAAV.U1a-SpCas9 and AAVsc.U6-sgTyr.CB6-EGFP vector constructs. Each construct is flanked by inverted terminal repeats (ITR, T-shaped structures). pA: polyadenylation signal from rabbit beta-globin gene. FIG. 7B shows a schematic diagram showing the genomic region of mouse Tyr gene targeted by CRISPR-Cas9. The start codon, stop codon, and the region containing targets of sgRNAs are indicated. The solid arrows indicate T7EI PCR primer binding sites. FIG. 7C shows a sequence of mouse Tyr region flanked by PCR primers shown in FIG. 7B (524 bp). The binding site of sgRNA4 is highlighted in bold; PCR primer sites are underlined and PAM location is boxed. The location of previously reported Tyr$^{c-2j}$ and Tyr$^{c}$ mutations are marked with solid and dotted circles, respectively. The sequence corresponds to SEQ ID NO: 28. FIG. 7D shows the sequence of five different sgRNAs designed to target exon1 of Tyr (the sgRNA region indicated in FIG. 7B). The PAM sequence of each sgRNA is underlined. The orientation and predicted sizes of cleavage bands following T7EI assay are shown. The sequences correspond to SEQ ID NOs: 29-33 from top to bottom, respectively. FIG. 7E shows results of the T7EI assay to validate the five different sgRNAs (shown in FIG. 7D) in GreenGo cells, sgRNA4 (bold in FIG. 7D) was the most efficient and was chosen for embryo experiments.

FIG. 8A shows results of T7EI assay to detect indels in E3.5 embryos that were transduced with different doses of rAAV6-Cas9 and rAAV6-sgTyr (1:1 ratio) at zygote stage. The dose is the total genome copies (GCs) of the two rAAV vectors contained in a drop of 15 ml of KSOM. Non-transduced embryos served as negative controls. Each lane represents the result of an individual embryo shown in FIG. 1B. FIG. 8B shows results of T7EI assay to detect indels in E16.5 embryos transduced with 6.0E+9 GCs of rAAV6-Cas9 and rAAV6-sgTyr (SpCas9+sgTyr) at zygote stage. Embryos that were infected with rAAV6-Cas9 only (SpCas9 only) or not infected (no infection) served as negative controls. Each lane represents the result of an individual embryo. FIG. 8C shows TOPO cloning and Sanger sequencing results of PCR products from the four embryos in the SpCas9+sgTyr group shown in FIG. 8B. The PAM sequence is boxed. Coding sequences for amino acid residues phenylalanine (F) and asparagine (N) are labeled. The asterisks represent the same sequence as reference; dashes, deletion mutations and arrowheads, insertion mutations. Eight TOPO clones were picked and sequenced for each embryo. Counts of each unique read are shown far right. The sequences correspond to SEQ ID NOs: 34-36 from left to right, respectively.

FIGS. 9A-9B show SMRT sequencing of CRISPR-Cas9-induced Tyr indel events. FIG. 9A shows a table of asymmetrically indexed primer sets for Tyr gene PCR. Boxed sequences indicate nucleotides that match the Tyr locus. The Barcode and primer sequences correspond to SEQ ID NOs: 37-60 from top to bottom, respectively. The Barcode alone sequences correspond to SEQ ID NOs: 61-84 from top to bottom, respectively. FIG. 9B shows a summary table of unique indel/editing events detected by SMRT sequencing of all sample libraries derived from E3.5 embryos shown in FIG. 1C. The PAM sequence is underlined, hyphens (-) mark deletion events, and italic bases indicate the insertion or alteration of base(s). The sequences correspond to SEQ ID NOs: 85-105 from top to bottom, respectively.

FIG. 11A shows TOPO sequencing analysis of Tyr gene editing in E3.5 embryos that were infected with the large-scale rAAV6-Cas9 and small-scale rAAV6-sgTyr vector preparations. FIG. 11B shows a gel image of silver staining of rAAV6-sgFahExon vectors prepared by the large-scale protocol (far left) and small-scale protocol (far right), together with a standard rAAV2 vector (5.0E+12 viral particles per milliliter, VP/mL) loaded at escalating amounts. Only three viral proteins, VP1, VP2, and VP3, are seen from top to bottom, indicating the purity of all rAAV vectors. FIG. 11C shows T7EI nuclease analysis of Fah gene editing in E3.5 embryos that were infected with the large-scale rAAV6-Cas9 and small-scale rAAV6-sgFahExon at two doses. Embryos that were not infected with rAAV serve as negative control. FIG. 11D shows a summary table showing Fah gene editing efficiency in eight embryo samples as determined by TOPO sequencing. Five to eight TOPO clones were sequenced for each embryo. Gene editing efficiency is calculated as the ratio of edited clones over total clones sequenced within each rAAV dose group.

FIG. 13A shows PCR analysis of tail snip DNA from albino mice shown in FIG. 1B to detect SpCas9 (top row) and EGFP (bottom row). Mouse 1 is positive for both genes, suggesting that it carries the genome of both rAAV6-Cas9 and rAAV6-sgTyr. M, 1 kb plus DNA ladder; N, no template; P, positive control; W, wild type sample. FIG. 13B shows PCR amplification to detect the junction area between ITR and Tyr gene at the predicted SpCas9 cleavage site of samples shown in FIG. 12A. The arrowhead indicates a positive band in mouse 1. FIG. 13C shows TOPO cloning of the highlighted band in FIG. 12B and Sanger sequencing results with chromatogram. The depicted sequence demonstrates fusion of the rAAV-ITR and the Tyr gene. The PAM sequence for sgTyr is also labeled. The sequence corresponds to SEQ ID NO: 106. FIG. 13D shows the integrated ITR adopts a "Flip" configuration. Black-colored sequence: detected in the TOPO sequencing. Gray-colored sequence: not detected in the TOPO sequencing but present in the rAAV vector genome. The sequence corresponds to SEQ ID NO: 107.

FIG. 14A shows results of T7EI assay conducted on tail DNA from pups shown in FIG. 3C. The albino pup (lane 1) and a black pup (lane 2) show evidence of gene editing events. FIG. 14B shows TOPO cloning and Sanger sequencing results of PCR products from four pups (1-4) shown in FIG. 13A. Two different small deletion mutations were detected in Tyr locus of albino pup (lane 1 in FIG. 13A). A small deletion mutation is also evident in one of the black pups (lane 2 in panel FIG. 13A). The PAM sequence is boxed. The sequence corresponds to SEQ ID NO: 108.

DETAILED DESCRIPTION

Figure 1A:
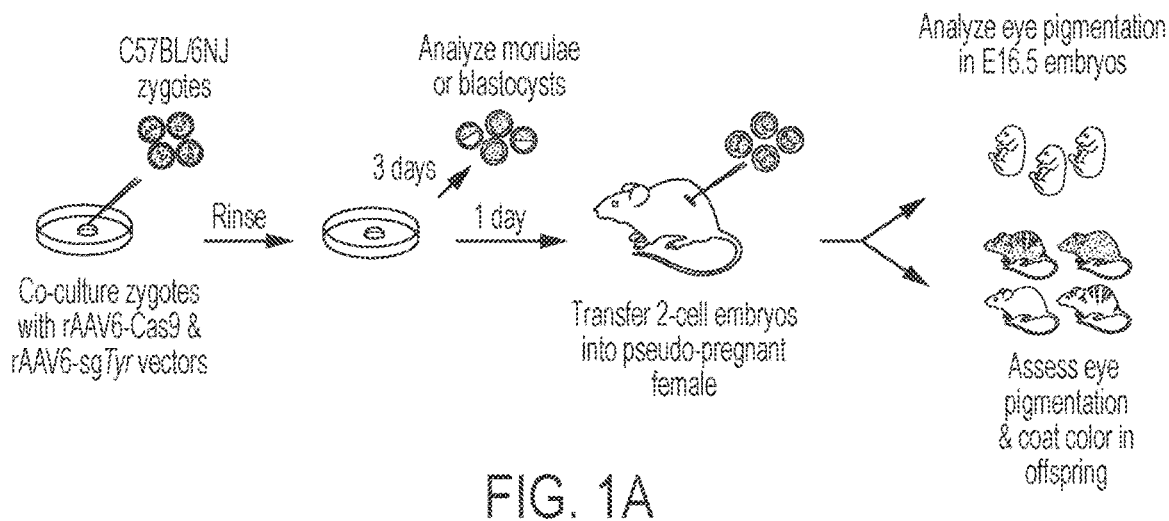
FIGS. 1A-1G show genome editing of intact pre-implantation embryos transduced with rAAV vectors.

Aspects of the invention relate to certain transgenes encoding gene editing molecules that when delivered to a pre-implantation embryo via recombinant adeno-associated viruses (rAAVs) are effective for inducing gene editing in the pre-implantation embryo. Accordingly, methods and compositions described herein are useful, in some embodiments, for gene editing in embryos.

Methods of Genome Editing

Methods for delivering a transgene (e.g., a gene encoding a genome editing molecule) to cells of a pre-implantation embryo are provided by the disclosure. The methods typically involve exposing cells of a pre-implantation embryo to isolated recombinant adeno-associated viral (rAAV) vectors comprising a nucleic acid for expression of a genome editing molecule.

As used herein, "genome editing" refers to adding, disrupting or changing genomic sequences (e.g., a gene sequence). In some embodiments, genome editing is performed using gene editing molecules such as engineered proteins and/or related molecules. In some aspects, genome editing comprises the use of engineered nucleases to cleave a target genomic locus. In some embodiments, genome editing further comprises inserting, deleting, mutating or substituting nucleic acid residues at a cleaved locus. In some embodiments, inserting, deleting, mutating or substituting nucleic acid residues at a cleaved locus is accomplished through endogenous cellular mechanisms such as homologous recombination (HR) and non-homologous end joining (NHEJ).

As used herein, the term a "gene editing molecule" refers to a molecule (e.g., nucleic acid or protein) capable of directing or affecting genome editing. Exemplary genome editing molecules include, but are not limited to, nucleases and recombinases, as well as nucleic acids that guide the activity of such enzymes, e.g., guide RNAs.

As used herein, the terms "endonuclease" and "nuclease" refer to an enzyme that cleaves a phosphodiester bond or bonds within a polynucleotide chain. Nucleases may be naturally occurring or genetically engineered. Genetically engineered nucleases are particularly useful for genome editing and are generally classified into four families: zinc finger nucleases (ZFNs), transcription activator-like effector nucleases (TALENs), engineered meganucleases and CRISPR-associated proteins (Cas nucleases). In some embodiments, the nuclease is a ZFN. In some embodiments, the ZFN comprises a FokI cleavage domain. In some embodiments, the ZFN comprises $Cys_2His_2$ fold group. In some embodiments, the nuclease is a TALEN. In some embodiments, the TALEN comprises a FokI cleavage domain. In some embodiments, the nuclease is an engineered meganuclease.

The term "CRISPR" refers to "clustered regularly interspaced short palindromic repeats," which are DNA loci containing short repetitions of base sequences. CRISPR loci form a portion of a prokaryotic adaptive immune system that confers resistance to foreign genetic material. Each CRISPR loci is flanked by short segments of "spacer DNA," which are derived from viral genomic material. In the Type II CRISPR system, spacer DNA hybridizes to transactivating RNA (tracrRNA) and is processed into CRISPR-RNA (crRNA) and subsequently associates with CRISPR-associated nucleases (Cas nucleases) to form complexes that recognize and degrade foreign DNA. In certain embodiments, the nuclease is a CRISPR-associated nuclease (Cas nuclease).

For the purpose of genome editing, the CRISPR system can be modified to combine the tracrRNA and crRNA in to a single guide RNA (sgRNA) or just (gRNA). As used herein, the term "guide RNA" or "gRNA" refers to a polynucleotide sequence that is complementary to a target sequence in a cell and associates with a Cas nuclease, thereby directing the Cas nuclease to the target sequence. In some embodiments, a gRNA ranges between 1 and 30 nucleotides in length. In some embodiments, a gRNA ranges between 5 and 25 nucleotides in length. In some embodiments, a gRNA ranges between 10 and 20 nucleotides in length. In some embodiments, a gRNA ranges between 14 and 18 nucleotides in length.

Examples of CRISPR nucleases include, but are not limited to Cas9, Cas6 and dCas9. dCas9 is an engineered Cas protein that binds to a target locus but does not cleave said locus. In some embodiments, the nuclease is Cas9. In some embodiments, a catalytically deficient form of the cas9 protein (dCas9) is fused with a C-terminal peptide domain that either activates or represses gene expression. In such embodiments, such a dCas9-effector fusion protein binds DNA in a sgRNA-guided manner. In some embodiments, the Cas9 is a mutated Cas9. In some embodiments, the Cas9 is a truncated Cas9. In some embodiments, the Cas9 is derived from a bacteria. In some embodiments, the Cas9 is derived from the bacteria *S. pyogenes* (SpCas9). In some embodiments, the SpCas9 is encoded in nucleic acid set forth in SEQ ID NO: 7.

Recombinases are enzymes that mediate site-specific recombination by binding to nucleic acids via conserved recognition sites and mediating at least one of the following forms of DNA rearrangement: integration, excision/resolution and/or inversion. Recombinases are generally classified into two families of proteins, tyrosine recombinases and serine recombinases based on the active amino acid of the catalytic domain. Recombinases may further be classified according to their directionality (i.e., bidirectional or unidirectional). Bidirectional recombinases bind to identical recognition sites and therefore mediate reversible recombination. Non-limiting examples of identical recognition sites for bidirectional recombinases include loxP, FRT and RS recognition sites. Unidirectional recombinases bind to non-identical recognition sites and therefore mediate irreversible recombination.

In some embodiments, the methods described herein utilize bidirectional recombinases for gene editing. Examples of bidirectional recombinases include, but are not limited to, Cre, FLP, R, IntA, Tn3 resolvase, Hin invertase and Gin invertase. In some embodiments, the methods described herein utilize unidirectional recombinases for gene editing. Examples of unidirectional recombinases include, but are not limited to, lambda, HK101, and pSAM2.

Aspects of the disclosure relate to delivery of gene editing molecules to embryonic cells via rAAV. In some embodiments, a gene editing molecule is delivered via a nucleic acid that is housed in the rAAV and that is engineered to express the gene editing molecule. However, in some embodiments, a gene editing molecule may be grafted to an rAAV capsid protein for delivery to an embryonic cell. Examples of gene editing molecules grafted to rAAV capsid proteins are described in International Application Publication Number WO/2016/131009, which is entitled COMPOSITIONS AND METHODS FOR TRANSIENT DELIVERY OF NUCLEASES, which was published on Aug. 18, 2016, and the contents of which relating to grafted AAV vectors are incorporated herein by reference.

"Homology" refers to the percent identity between two polynucleotides or two polypeptide moieties. The term "substantial homology", when referring to a nucleic acid, or fragment thereof, indicates that, when optimally aligned with appropriate nucleotide insertions or deletions with another nucleic acid (or its complementary strand), there is nucleotide sequence identity in about 90 to 100% of the aligned sequences. When referring to a polypeptide, or fragment thereof, the term "substantial homology" indicates that, when optimally aligned with appropriate gaps, insertions or deletions with another polypeptide, there is nucleotide sequence identity in about 90 to 100% of the aligned sequences. The term "highly conserved" means at least 80% identity, preferably at least 90% identity, and more preferably, over 97% identity. In some cases, highly conserved may refer to 100% identity. Identity is readily determined by one of skill in the art by, for example, the use of algorithms and computer programs known by those of skill in the art.

As described herein, alignments between sequences of nucleic acids or polypeptides are performed using any of a variety of publicly or commercially available Multiple Sequence Alignment Programs, such as "Clustal W", accessible through Web Servers on the internet. Alternatively, Vector NTI utilities may also be used. There are also a number of algorithms known in the art which can be used to measure nucleotide sequence identity, including those contained in the programs described above. As another example, polynucleotide sequences can be compared using BLASTN, which provides alignments and percent sequence identity of the regions of the best overlap between the query and search sequences. Similar programs are available for the comparison of amino acid sequences, e.g., the "Clustal X" program, BLASTP. Typically, any of these programs are used at default settings, although one of skill in the art can alter these settings as needed. Alternatively, one of skill in the art can utilize another algorithm or computer program which provides at least the level of identity or alignment as that provided by the referenced algorithms and programs. Alignments may be used to identify corresponding amino acids between two proteins or peptides. A "corresponding amino acid" is an amino acid of a protein or peptide sequence that has been aligned with an amino acid of another protein or peptide sequence. Corresponding amino acids may be identical or non-identical. A corresponding amino acid that is a non-identical amino acid may be referred to as a variant amino acid.

Alternatively for nucleic acids, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art.

A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

The skilled artisan will also realize that conservative amino acid substitutions may be made to provide functionally equivalent variants, or homologs of the capsid proteins. In some aspects the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides disclosed herein.

Aspects of the disclosure relate to production of transgenic animals using rAAV-mediated delivery of gene editing molecules. A transgenic animal is a non-human animal (e.g., a mouse). The transgenic animals produced by the methods disclosed herein may be useful as a model of a disease or as a tool for characterizing the effects of a gene for which the function is unknown or not fully understood. In some embodiments, a stable transgenic animal may be produced by multiple doses of an rAAV.

Isolated Nucleic Acids

In some aspects, the disclosure provides isolated nucleic acids that are useful for expressing a gene editing molecule. A "nucleic acid" sequence refers to a DNA or RNA sequence. In some embodiments, proteins and nucleic acids of the disclosure are isolated. As used herein, the term "isolated" means artificially produced. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

The skilled artisan will also realize that conservative amino acid substitutions may be made to provide functionally equivalent variants, or homologs of the capsid proteins. In some aspects the disclosure embraces sequence alterations that result in conservative amino acid substitutions. As used herein, a conservative amino acid substitution refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made among amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the proteins and polypeptides disclosed herein.

The isolated nucleic acids of the invention may be recombinant adeno-associated virus (AAV) vectors (rAAV vectors). In some embodiments, an isolated nucleic acid as described by the disclosure comprises a region (e.g., a first region) comprising a first adeno-associated virus (AAV) inverted terminal repeat (ITR), or a variant thereof. The isolated nucleic acid (e.g., the recombinant AAV vector) may be packaged into a capsid protein and administered to a subject and/or delivered to a selected target cell. "Recombinant AAV (rAAV) vectors" are typically composed of, at a minimum, a transgene and its regulatory sequences, and 5' and 3' AAV inverted terminal repeats (ITRs). The transgene may comprise, as disclosed elsewhere herein, one or more regions that encode one or more gene editing molecules (e.g., Cas9). The transgene may also comprise a region encoding, for example, a miRNA binding site, and/or an expression control sequence (e.g., a poly-A tail), as described elsewhere in the disclosure.

Generally, ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al., "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types. In some embodiments, the isolated nucleic acid (e.g., the rAAV vector) comprises at least one ITR having a serotype selected from AAV1, AAV2, AAV5, AAV6, AAV6.2, AAV7, AAV8, AAV9, AAV10, AAV11, and variants thereof. In some embodiments, the isolated nucleic acid comprises a region (e.g., a first region) encoding an AAV2 ITR.

In some embodiments, the isolated nucleic acid further comprises a region (e.g., a second region, a third region, a fourth region, etc.) comprising a second AAV ITR. In some embodiments, the second AAV ITR has a serotype selected from AAV1, AAV2, AAV5, AAV6, AAV6.2, AAV7, AAV8, AAV9, AAV10, AAV11, and variants thereof. In some embodiments, the second ITR is a mutant ITR that lacks a functional terminal resolution site (TRS). The term "lacking a terminal resolution site" can refer to an AAV ITR that comprises a mutation (e.g., a sense mutation such as a non-synonymous mutation, or missense mutation) that abrogates the function of the terminal resolution site (TRS) of the ITR, or to a truncated AAV ITR that lacks a nucleic acid sequence encoding a functional TRS (e.g., a ΔTRS ITR). Without wishing to be bound by any particular theory, a rAAV vector comprising an ITR lacking a functional TRS produces a self-complementary rAAV vector, for example as described by McCarthy (2008) *Molecular Therapy* 16(10): 1648-1656.

In addition to the major elements identified above for the recombinant AAV vector, the vector also includes conventional control elements which are operably linked with elements of the transgene in a manner that permits its transcription, translation and/or expression in a cell transfected with the vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A number of expression control sequences, including promoters which are native, constitutive, inducible and/or tissue-specific, are known in the art and may be utilized.

As used herein, a nucleic acid sequence (e.g., coding sequence) and regulatory sequences are said to be operably linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., miRNA).

A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene.

For nucleic acids encoding proteins, a polyadenylation sequence generally is inserted following the transgene sequences and before the 3' AAV ITR sequence. A rAAV construct useful in the present disclosure may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available [see, e.g., Sambrook et al., and references cited therein at, for example, pages 3.18 3.26 and 16.17 16.27 and Ausubel et al., Current Protocols in Molecular Biology, John Wiley & Sons, New York, 1989]. In some embodiments, a Foot and Mouth Disease Virus 2A sequence is included in polyprotein; this is a small peptide (approximately 18 amino acids in length) that has been shown to mediate the cleavage of polyproteins (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459). The cleavage activity of the 2A sequence has previously been demonstrated in artificial systems including plasmids and gene therapy vectors (AAV and retroviruses) (Ryan, M D et al., EMBO, 1994; 4: 928-933; Mattion, N M et al., J Virology, November 1996; p. 8124-8127; Furler, S et al., Gene Therapy, 2001; 8: 864-873; and Halpin, C et al., The Plant Journal, 1999; 4: 453-459; de Felipe, P et al., Gene Therapy, 1999; 6: 198-208; de Felipe, P et al., Human Gene Therapy, 2000; 11: 1921-1931; and Klump, H et al., Gene Therapy, 2001; 8: 811-817).

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter is an enhanced chicken β-actin promoter. In some embodiments, a promoter is a U6 promoter. In some embodiments, a promoter is a chicken beta-actin (CBA) promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart cell-specific gene expression capabilities. In some cases, the cell-specific regulatory sequences bind cell-specific transcription factors that induce transcription in a cell specific manner. Such cell-specific regulatory sequences (e.g., promoters, enhancers, etc.) are known in the art. In some embodiments, the cell-specific promoter is an embryonic cell-specific promoter. In some embodiments, the embryonic cell-specific promoter is the EC1.2 promoter.

Recombinant Adeno-Associated Viruses (rAAVs)

In some aspects, the disclosure provides isolated AAVs. As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a transgene of the rAAV will be delivered specifically to one or more predetermined tissue(s). The AAV capsid is an important element in determining these tissue-specific targeting capabilities. Thus, an rAAV having a capsid appropriate for the tissue being targeted can be selected.

Methods for obtaining recombinant AAVs having a desired capsid protein are well known in the art. (See, for example, US 2003/0138772), the contents of which are incorporated herein by reference in their entirety). Typically the methods involve culturing a host cell which contains a nucleic acid sequence encoding an AAV capsid protein; a functional rep gene; a recombinant AAV vector composed of, AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

In some embodiments, an AAV capsid protein is of an AAV serotype selected from the group consisting of AAV2, AAV3, AAV4, AAV5, AAV6, AAV8, AAVrh8, AAV9, and AAV10. In some embodiments, an AAV capsid protein is of a serotype derived from a non-human primate, for example AAVrh8 serotype. In some embodiments, the AAV capsid protein is of a serotype that has tropism for the eye of a subject, for example an AAV (e.g., AAV5, AAV6, AAV6.2, AAV7, AAV8, AAV9, AAVrh.8, AAVrh.10, AAVrh.39 and AAVrh.43) that transduces ocular cells of a subject more efficiently than other vectors. In some embodiments, an AAV capsid protein is of an AAV8 serotype or an AAV5 serotype. In some embodiments, the AAV capsid protein comprises the sequence set forth in SEQ ID NO: 1.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

In some embodiments, the instant disclosure relates to a host cell containing a nucleic acid that comprises a coding sequence encoding a gene editing molecule (e.g., Cas9). In some embodiments, the instant disclosure relates to a composition comprising the host cell as described herein. In some embodiments, the composition comprising the host cell as described herein further comprises a cryopreservative.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., Molecular Cloning: A Laboratory Manual, Cold Spring Harbor Press, Cold Spring Harbor, N.Y. Similarly, methods of generating rAAV virions are well known and the selection of a suitable method is not a limitation on the present disclosure. See, e.g., K. Fisher et al., J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

A "host cell" refers to any cell that harbors, or is capable of harboring, a substance of interest. Often a host cell is a mammalian cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or functional RNA (e.g., guide RNA) from a transcribed gene. The foregoing methods for packaging recombinant vectors in desired AAV capsids to produce the rAAVs of the disclosure are not meant to be limiting and other suitable methods will be apparent to the skilled artisan.

rAAV-Mediated Delivery of Gene Editing Molecules to Embryonic Cells

Methods for delivering a transgene encoding a gene editing molecule to cells of a pre-implantation embryo are provided herein. The methods typically involve administering to cells of a pre-implantation embryo an effective amount of a rAAV comprising a nucleic acid for expressing a transgene (e.g., a Cas9 protein or fragment thereof) in the embryonic cell.

An "effective amount" of a rAAV is an amount sufficient to infect a sufficient number of cells of a pre-implantation embryo. An effective amount of a rAAV may be an amount sufficient to induce gene editing in the cell of a pre-implantation embryo, e.g., to insert, delete, mutate or substitute nucleic acid residues in a gene. The effective amount will depend on a variety of factors such as, for example, the species, age, source of the embryonic cell, and the stage of the embryonic cell to be targeted, and may thus vary among embryonic cells.

An effective amount may also depend on the rAAV used. The invention is based, in part on the recognition that rAAV comprising capsid proteins having a particular serotype (e.g., AAV5, AAV6, AAV6.2, AAV7, AAV8, AAV9, AAVrh.8, AAVrh.10, AAVrh.39, and AAVrh.43) mediate more efficient transduction of cells of a pre-implantation embryo than rAAV comprising capsid proteins having a different serotype. Thus in some embodiments, the rAAV comprises a capsid protein of an AAV serotype selected from the group consisting of: AAV2, AAV5, AAV6, AAV6.2, AAV7, AAV8, AAV9, AAVrh.8, AAVrh.10, AAVrh.39, and AAVrh.43. In some embodiments, the rAAV comprises a capsid protein of AAV6 serotype (SEQ ID NO: 1). In some embodiments, the capsid protein comprises an amino acid sequence that is at least 70%, at least 80%, at least 90%, at least 95%, or at least 99% identical to SEQ ID NO: 1. In some embodiments, the capsid protein is AAV6 capsid protein.

In certain embodiments, the effective amount of rAAV is $10^{10}$, $10^{11}$, $10^{12}$, $10^{13}$, or $10^{14}$ genome copies per kg. In certain embodiments, the effective amount of rAAV is $10^{10}$, $10^{11}$, $10^{12}$, $10^{13}$, $10^{14}$, or $10^{15}$ genome copies per subject.

An effective amount may also depend on the location of the pre-implantation embryo. For example, targeting an in vitro pre-implantation embryo (e.g., a pre-implantation embryo in an in vitro culture) may require different (e.g., higher or lower) doses, in some cases, than targeting an in vivo pre-implantation embryo (e.g., a pre-implantation embryo in the oviduct of a subject). In some embodiments, targeting an in vivo pre-implantation embryo comprises injecting rAAV into the oviduct of a subject. In some embodiments, oviduct injection of rAAV having certain serotypes (e.g., AAV5, AAV6, AAV6.2, AAV7, AAV8, AAV9, AAVrh.8, AAVrh.10, AAVrh.39, and AAVrh.43) mediates efficient transduction of cells of the pre-implantation embryo. In some embodiments, the injection is into the ampulla of the oviduct. In some cases, multiple doses of a rAAV are administered.

Without wishing to be bound by any particular theory, efficient transduction of cells of a pre-implantation embryo by rAAV described herein may be useful for inducing gene editing in the cells of the pre-implantation embryo (e.g., an insertion, a deletion, a mutation or a substitution of nucleic acid residues in a gene). Accordingly, methods and compositions for inducing gene editing are also provided herein.

In some aspects, the disclosure provides a method for inducing gene editing (e.g., an insertion, a deletion, a mutation or a substitution of nucleic acid residues in a gene), the method comprising: administering to a pre-implantation embryo an effective amount of rAAV, wherein the rAAV comprises (i) a capsid protein having a serotype selected from the group consisting of AAV2, AAV5, AAV6, AAV6.2, AAV7, AAV8, AAV9, AAVrh.8, AAVrh.10, AAVrh.39, and AAVrh.43, and (ii) a nucleic acid comprising a promoter operably linked to a transgene (e.g., a transgene encoding a gene editing molecule as described by the disclosure).

In some embodiments, administration of a rAAV (or isolated nucleic acid) as described by the disclosure results in transduction of cell of a pre-implantation embryo. In some embodiments, the pre-implantation embryo is a mammalian pre-implantation embryo. In some embodiments, the pre-implantation embryo is located within a mammalian subject.

The embryonic cell may be at various stages in division. In some embodiments, the pre-implantation embryo is at a zygote, morula, or pre-implantation blastocyst stage. In some embodiments, the pre-implantation embryo is at a two-cell stage, four-cell stage, or eight-cell stage.

The rAAVs may be delivered to a subject in compositions according to any appropriate methods known in the art. The rAAV, preferably suspended in a physiologically compatible carrier (i.e., in a composition), may be administered to a subject, i.e. host animal, such as a human, mouse, rat, cat, dog, sheep, rabbit, horse, cow, goat, pig, guinea pig, hamster, chicken, turkey, or a non-human primate (e.g., Macaque). In some embodiments, a host animal does not include a human.

Delivery of the rAAVs to a mammalian subject includes, but is not limited to, transplantation of a pre-implantation embryo transduced with rAAVs into the subject and injection of rAAVs into the oviduct of the subject. In some embodiments, the delivery of the rAAVs to the mammalian subject comprises combinations of administration methods (e.g., transplantation and injection). In some embodiments, the pre-implantation embryo is transferred to the uterus of a female animal.

The compositions of the disclosure may comprise an rAAV alone, or in combination with one or more other viruses (e.g., a second rAAV encoding having one or more different transgenes). In some embodiments, a composition comprises 1, 2, 3, 4, 5, 6, 7, 8, 9, 10, or more different rAAVs each having one or more different transgenes.

In some embodiments, a composition further comprises a pharmaceutically acceptable carrier. Suitable carriers may be readily selected by one of skill in the art in view of the indication for which the rAAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure.

Optionally, the compositions of the disclosure may contain, in addition to the rAAV and carrier(s), other pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The rAAVs are administered in sufficient amounts to transfect cells of a pre-implantation embryo and to provide sufficient levels of gene transfer and expression without undue adverse effects. Examples of pharmaceutically acceptable routes of administration include, but are not limited to, contacting rAAVs with a pre-implantation embryo in vitro and contacting rAAVs with a pre-implantation embryo in vivo. Routes of administration may be combined, if desired.

The dose of rAAV virions required to achieve a particular "gene editing effect," e.g., the units of dose in genome copies/per kilogram of body weight (GC/kg), will vary based on several factors including, but not limited to: the route of rAAV virion administration, the level of gene or RNA expression required to achieve a gene editing effect, the specific gene being edited, and the stability of the gene or RNA product. One of skill in the art can readily determine a rAAV virion dose range to induce a gene editing effect in an embryonic cell based on the aforementioned factors, as well as other factors.

An effective amount of an rAAV is an amount sufficient to target infect cells of a pre-implantation embryo of a subject (e.g., an animal). The effective amount will depend primarily on factors such as the species, age, weight, and health of the subject, and may thus vary among animals. For example, an effective amount of the rAAV is generally in the range of from about 1 ml to about 100 ml of solution containing from about $10^9$ to $10^{16}$ genome copies. In some cases, a dosage between about $10^{11}$ to $10^{13}$ rAAV genome copies is appropriate. In certain embodiments, $10^9$ rAAV genome copies is effective to target an embryonic cell in a subject (e.g., in the oviduct). In some embodiments, a dose more concentrated than $10^9$ rAAV genome copies is toxic when administered to the oviduct of a subject. In some embodiments, an effective amount is produced by multiple doses of an rAAV.

In some embodiments, a dose of rAAV is administered to a subject no more than once per calendar day (e.g., a 24-hour period). In some embodiments, a dose of rAAV is administered to a subject no more than once per 2, 3, 4, 5, 6, or 7 calendar days. In some embodiments, a dose of rAAV is administered to a subject no more than once per calendar week (e.g., 7 calendar days). In some embodiments, a dose of rAAV is administered to a subject no more than bi-weekly (e.g., once in a two calendar week period). In some embodiments, a dose of rAAV is administered to a subject no more than once per calendar month (e.g., once in 30 calendar days). In some embodiments, a dose of rAAV is administered to a subject no more than once per six calendar months. In some embodiments, a dose of rAAV is administered to a subject no more than once per calendar year (e.g., 365 days or 366 days in a leap year). In some embodiments, a dose of rAAV is administered to a subject no more than once per two calendar years (e.g., 730 days or 731 days in a leap year). In some embodiments, a dose of rAAV is administered to a subject no more than once per three calendar years (e.g., 1095 days or 1096 days in a leap year).

In some embodiments, rAAV compositions are formulated to reduce aggregation of AAV particles in the composition, particularly where high rAAV concentrations are present (e.g., ~$10^{13}$ GC/ml or more). Appropriate methods for reducing aggregation of may be used, including, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments, rAAVs in suitably formulated pharmaceutical compositions disclosed herein are delivered directly to an embryonic cell. However, in certain circumstances it may be desirable to separately or in addition deliver the rAAV-based therapeutic constructs via another route, e.g., subcutaneously, topically, intrapancreatically, intranasally, parenterally, intravenously, intramuscularly, intrathecally, or orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by oviduct injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a suitable sterile aqueous medium may be employed. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active rAAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The rAAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the rAAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Alternatively, nanocapsule formulations of the rAAV may be used. Nanocapsules can generally entrap substances in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use.

Kits and Related Compositions

The agents described herein may, in some embodiments, be assembled into pharmaceutical or diagnostic or research kits to facilitate their use in therapeutic, diagnostic or research applications. A kit may include one or more containers housing the components of the disclosure and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

In some embodiments, the instant disclosure relates to a kit for producing an isolated recombinant Adeno-Associated Virus (rAAV) for genome editing in a cell of a pre-implantation embryo, comprising at least one container housing a rAAV vector, wherein the rAAV comprises at least one capsid protein, and a nucleic acid comprising a promoter operably linked to a transgene encoding a gene editing molecule, at least one container housing a rAAV packaging component, and instructions for constructing and packaging the rAAV, wherein the rAAV transduces a cell of a pre-implantation embryo.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. Exemplary embodiments of the invention will be described in more detail by the following examples. These embodiments are exemplary of the invention, which one skilled in the art will recognize is not limited to the exemplary embodiments.

EXAMPLES

In order that the invention described herein may be more fully understood, the following examples are set forth. The examples described in this application are offered to illustrate the methods, compositions, and systems provided herein and are not to be construed in any way as limiting their scope.

Introduction to Examples

The advent of clustered regularly interspaced short palindromic repeats-Cas9 (CRISPR-Cas9) gene editing technology has revolutionized gene targeting approaches and greatly facilitates the generation of genetically modified mice. However, despite the impressive advances in genome editing technology, methods to deliver nucleic acids into pre-implantation embryos has undergone minimal change. The conventional method, developed more than thirty years ago, relies on microinjection of zygotes to introduce RNA or DNA constructs. This technique requires sophisticated micromanipulation equipment operated by specially trained personnel. An alternative approach is to use lentiviral vectors. However, lentivirus-based vectors have been shown to non-specifically integrate into the genome of the host cells, limiting their utility as an effective tool for generating transgenic mice. Furthermore, they are unable to transduce pre-implantation embryos unless the zona pellucida is removed.

As disclosed herein, it is feasible to use recombinant adeno-associated viral (rAAV) vectors to bypass the zona pellucida and transduce pre-implantation embryos. The disclosed rAAV vectors transduced intact mouse embryos and induced efficient gene editing. The rAAV genomes are predominantly episomal after transduction, and can lead to high levels of transgene expression when delivered into host tissues. The relatively low genotoxicity of rAAVs is also beneficial for its use in human gene therapy applications.

Materials and Methods

Mouse Strains and Embryo Collection

C57BL/6NJ (Stock No. 005304), FVB/NJ (Stock No. 001800), and R26$^{mTmG}$ (Gt(ROSA)-26Sor$^{tm4(ACTB-tdTomato,EGFP)Luo}$, Stock No. 007676) mice were obtained from The Jackson Laboratory. CD-1 mice were obtained from Charles River Laboratories (Strain code 022). R26$^{mTmG}$ mice were maintained in a CD-1 outbred genetic background. Animals were maintained in a 12 h light cycle. The middle of the light cycle of the day when a mating plug was observed was considered embryonic day 0.5 (E0.5) of gestation. Zygotes and morulae were collected according to standard procedures. Briefly, zygotes were collected at E0.5 by tearing the ampulla with forceps and incubation in M2 medium containing hyaluronidase to remove cumulus cells. Eight-cell morulae were collected by flushing the oviduct with M2 medium at E2.5.

Recombinant AAV Vectors

All the rAAV serotypes used in morulae experiments contained the same rAAV.CB6-EGFP construct. The EGFP expression vector consists of the CB6 promoter (cytomegalovirus enhancer fused to the chicken beta-actin promoter) driving EGFP expression. rAAV6.CB6-Cre carries the Cre recombinase gene driven by the CB6 promoter. In rAAV6.U1a-SpCas9, expression of the S. pyogenes Cas9 (SpCas9) is driven by the ubiquitous U1a promoter. scAAV6.U6-sgRNA.CB6-EGFP carries two expression cassettes, one expressing the sgRNA targeting the Tyrosinase (Tyr) gene or the Fah gene under the U6 promoter, and the other expressing EGFP under the CB6 promoter.

rAAV Production and Purification rAAV vectors were produced by calcium phosphate triple-transfection of plasmids in HEK293 cells. For large-scale preparation, approximately $8.5 \times 10^8$ cells were transfected. rAAV was purified by two rounds of CsCl sedimentation followed by dialysis, which took a period of seven days. For small-scale preparation, approximately $1.7 \times 10^8$ cells were transfected. rAAV was purified by iodixanol gradient centrifugation followed by desalting using a Zeba column (ThermoFisher Scientific, Cat. No. 89894) and concentration using an Amicon Filter Unit (EMD Millipore, Cat. No. UFC910024), which took one day to finish. All rAAV vectors were titrated by droplet digital PCR (ddCPR, Biorad) for genomes and silver staining of capsid proteins.

Ex Vivo Transduction of Pre-Implantation Embryos in Explant Culture

Zygotes or 8-cell morulae were incubated in 10 or 15 μl drops of KSOM (Potassium-Supplemented Simplex Optimized Medium, Millipore, Cat. No. MR-020P-5F) containing the following rAAV vectors: scAAV.CB6-EGFP ($9.0 \times 10^9$ GCs); scAAV6.CB6-EGFP ($2.25 \times 10^9$ GCs); rAAV6.CB6-Cre ($3.75 \times 10^9$ GCs); rAAV6.U1a-SpCas9 ($3.0 \times 10^9$ GCs, $1.5 \times 10^9$ GCs, $3.0 \times 10^8$ GCs, $3.0 \times 10^7$ GCs or $3.0 \times 10^6$ GCs); scAAV6.U6-sgTyr.CB6-EGFP ($3.0 \times 10^9$ GCs, $1.5 \times 10^9$ GCs, $3.0 \times 10^8$ GCs, $3.0 \times 10^7$ GCs or $3.0 \times 10^6$ GCs); rAAV6.TyrDonorWithSNT.CB6-mCherry ($3.0 \times 10^9$ GCs); rAAV6.TyrDonorWithP2A-BFP.CB6-mCherry ($3.0 \times 10^9$ GCs); scAAV6.U6-sgFahExon.CB6-EGFP ($3.0 \times 10^9$ GCs, $3.0 \times 10^8$ GCs) for 5~6 hours. Drops were placed in 35 mm plates under mineral oil (Sigma, M8410) at 37° C. in a tissue culture incubator containing 5% CO2 and 5% $O_2$. After the incubation period, the embryos were rinsed once in M2 medium and transferred to fresh KSOM for subsequent culture. Zygotes were cultured for 3 days and morulae for 1 day to reach compacted morula or blastocyst stages. To develop transduced zygotes to term, embryos were cultured overnight and those that advanced to the 2-cell stage were transferred into the oviduct of E0.5 pseudo-pregnant CD-1 females.

Transduction of Zygotes In Vivo Using rAAVs

Recombinant AAVs were injected into the oviduct of females on the day when the mating plug was observed (E0.5). Only the oviduct of the left horn was injected. The untreated right horn served as a hedge for pregnancy loss in the case of embryo lethality on the treated side of the oviduct. The volume injected ranged from 1.5 to 3 μl and was injected using glass needles with tip diameter of 15-30 mm. The tracer dye Chicago sky blue (0.1%) (Sigma Cat. No. C8679) was used to track the site of injection. To generate indels using the CRISPR-Cas9 system, E0.5 C57BL/6NJ females mated to males of the same strain were injected. A 1:1 mixture of rAAV6.U1a-SpCas9 and scAAV6.U6-sgTyr.CB6-EGFP ($4.0 \times 10^9$ GCs/l each) was injected into the ampulla of the left oviduct. The right oviduct was not injected. Operated females were allowed to deliver the pups or were euthanized at E16.5 to obtain embryos for analysis.

Analysis of Embryos or Pups Transduced with rAAV6.CB6-Cre

To determine Cre-mediated recombination in transduced R26$^{mTmG/+}$ embryos, EGFP fluorescence was assessed in morulae, blastocysts, or E16.5 embryos. Fluorescence was assessed qualitatively relative to non-transduced controls using an inverted Leica microscope (DMI4000) or a Leica stereoscope (MZ16F) equipped with epifluorescence. Pups were screened at postnatal day 1 or 2 (P1 or P2) for the presence of EGFP (mG) or tdTomato (mT) fluorescence using a dual fluorescent protein flashlight (Nightsea, Bedford, Mass. USA).

Fluorescence Imaging of Adult Tissue Cryosections

Mice were anesthetized by isoflurane, and transcardially perfused with ice-cold PBS followed by 4% paraformaldehyde (PFA). Organs were dissected and post-fixed in 4% PFA overnight.

Organs were then cryopreserved in 30% sucrose overnight, embedded in Tissue-Tek O.C.T. compound (Sakura Finetek), and sectioned at a thickness of 8-micrometers in a cryostat. Tissue sections were mounted with vectashield mounting medium containing DAPI (Vector Labs, H1200), and imaged using an upright fluorescence microscope (Leica DM5500B).

Analysis of Embryos or Pups Transduced with CRISPR-Cas9 AAV Vectors

To determine the genotype of edited Tyr alleles, individual compacted morulae, blastocysts, or E16.5 embryos were collected and subjected to single-molecule, real-time (SMRT) sequencing analysis or T7EI nuclease assay. The phenotype was assessed at E16.5 or after birth. The levels of eye pigmentation in E16.5 embryos were determined using a dissection microscope (Leica MZ16F) equipped with color camera (Leica DFC420). For P2 or later pups, eye pigmentation and coat color were visually assessed.

Single-Molecule, Real-Time (SMRT) Sequencing and Bioinformatics Analysis

Harvested embryos were subjected to whole genome amplification using the REPLI-g Single Cell Kit (Qiagen, Cat No. 150343). A portion of the Tyr gene was amplified using the KOD Hot Start DNA Polymerase (EMD Millipore, Cat. No. 71086), and purified using the QIAquick PCR purification kit (Qiagen, Cat No. 28106). Primer pairs used for PCR were uniquely indexed for each embryo at the 5' ends with 16-nucleotide asymmetric barcodes (see FIG. 9A for complete primer set list). PCR products were pooled for SMRTbell template preparation and sequenced using a PacBio RS II sequencer following standard guidelines and procedures by the University of Massachusetts Medical School, Deep Sequencing Core. Raw reads were processed by SMRT Analysis software (v2.3.0) pipelines to produce reads-of-inserts representing multiplexed PCR amplicon sequences in fastq format. All downstream workflows were performed using the Galaxy web-based platform for genome data analysis, unless specified. Reads were filtered by length and demultiplexed. Sequences were then aligned with BWA-MEM to a custom reference representing the unedited, wild-type Tyr amplicon sequence.

Imperfect alignments (deletions, insertions, and mismatches) across the predicted edit site (-3 nt of the PAM) were designated as indel events. To determine the distribution of indel-types due to Cas9 editing, only full and intact reads that encompassed both asymmetric barcodes were considered for analysis. Fasta formatted reads were clustered with USEARCH v8.1 sequence analysis tools. Specifically, identical sequences were tabulated with the -derep_fulllength command, followed by sequence clustering using operational taxonomic units (OTU) with the -cluster_otus command with the following options: -fulldp, -otu_radius_pct 0.1, -minsize 5, -gapopen *I/1.0E, and -gapext *I/0.5E. Sequence clusters were manually curated to group and count indel-types. Unique indel types were scored as a percentage of total reads.

DNA Preparation for T7EI Assay

GreenGo cells were co-transfected with pAAV.U1a-SpCas9 and pAAVsc.U6-sgTyr.CB6-EGFP using Lipofectamine 3000 Transfection Reagent (Thermo Fisher Sci. Cat. No. L3000015). Three days later, total DNA was extracted using the QIAamp DNA Mini Kit (Qiagen, Cat. No. 51306). Embryos cultured up to compacted morula or blastocyst stages were harvested and subjected to whole genome amplification using the REPLI-g Single Cell Kit (Qiagen, Cat No. 150343). Whole E16.5 embryos were stored at −80° C. until being powdered in liquid nitrogen. DNA was then extracted from tissue powder using the Blood & Cell Culture DNA Maxi Kit (Qiagen, Cat No. 13362).

T7EI Nuclease Assay

A portion of the Tyr gene or Fah gene was amplified using the KOD Hot Start DNA Polymerase (EMD Millipore, Cat. No. 71086), purified using the QIAquick PCR purification kit (Qiagen, Cat. No. 28106), and subjected to T7EI nuclease assay according to manufacturer's instruction (NEB, Cat. No. M0302L). Digested products were resolved on a 2% agarose gel containing ethidium bromide and imaged. Primers used for PCR are listed in Table 1.

TOPO Sequencing

PCR products were purified using the QIAquick PCR Purification Kit (Qiagen, Cat. No. 28106). Purified PCR products were cloned into the pCR™-Blunt II-TOPO vector using Zero Blunt TOPO PCR Cloning Kit (Thermo Fisher Sci. Cat. No. K280002), and used to transform DH5α E. coli cells. Plasmid from individual colonies was extracted using the QIAcube automated sample preparation station (Qiagen), and subjected to Sanger sequencing.

rAAV Genome Integration Analysis

DNA libraries for integration profiling were generated by Linear Amplification Mediated-PCR (LAM-PCR) and subjected to SMRT-sequencing. The overall protocol design was modified from the high-throughput, genome-wide, translocation sequencing (HTGTS) procedure. Briefly, whole-genomic DNAs were extracted from snap-frozen and powdered tissues from experimental E16.5 embryos, and adult mouse liver treated with rAAV9-SpCas9 and rAAV9.U6-sgAspa.CB6-EGFP as a positive control sample. Genomic material (20 µg total input) was fragmented by $Taq^{\alpha}I$ digestion (NEB, Cat. No. R0149M). Fragmented DNAs were subjected to phenol-chloroform extraction and ethanol precipitation to purify the fragmented material. Template DNAs were next subjected to 80 cycles of LAM-PCR with KOD Hot Start DNA Polymerase and a biotinylated primer with specificity to the rAAV-polyA sequence:

(SEQ ID NO: 21)
5'-/5Biosg/CTTGAGCATCTGACTTCTGGCTAATAAAGG-3'.

Single-strand, biotinylated PCR products were next captured on magnetic beads, enriched, and ligated to a bridge adapter by on-bead ligation. Nested PCR (30-cycles) to generate SMRT-sequencing libraries was next carried out using asymmetrically barcoded forward and reverse primer sets (SEQ ID NOs: 22 and 23, respectively):

Forward:
5'-NNNNNNNNNNNNNNNNNNAGGAACCCCTAGTGATGGAGT-3'

Reverse:
5'-NNNNNNNNNNNNNNNNNNACTATAGGGCACGCGTGGT-3'

Individual libraries were then subjected to 0.6× AMPurePB bead (Pacific Biosciences, Cat. No. 100-265-900) purification, pooled, and submitted for standard SMRT-sequencing analysis as described above. The resulting reads-of-inserts

TABLE 1

List of primers used in PCR analysis.

| Target | Orientation | Sequence | SEQ ID NO: |
|---|---|---|---|
| Tyr | Forward | 5'-TTGTTGGCAAAAGAATGCTG-3' | 11 |
|  | Reverse | 5'-GCTTCATGGGCAAAATCAAT-3' | 12 |
| Tyr G to T Transversion | Forward | 5'-TGAAGCAGTTCACCAAAATAAC-3' | 13 |
|  | Reverse | 5'-CTGTTTGAGAGTCAGCAACG-3' | 14 |
| BFP/Tyr 5' Junction | Forward | 5'-TGAAGCAGTTCACCAAAATAAC-3' | 15 |
|  | Reverse | 5'-GCGAGCTGATTAAGGAGAAC-3' | 16 |
| BFP/Tyr 3' Junction | Forward | 5'-GCTAAGAACCTCAAGATGCC-3' | 17 |
|  | Reverse | 5'-CGTTGCTGACTCTCAAACAG-3' | 18 |
| Fah | Forward | 5'-ACCCCTGTGTGATAGACCAC-3' | 19 |
|  | Reverse | 5'-CATGGGCTGCTATTTGTGGC-3' | 20 |

(ROIs) were filtered by barcode-demultiplexing and screened for the presence of a 10-nt feature that is unique to the rAAV-ITR (5'-TGGCCACTCC-3') (SEQ ID NO: 24). This filtering method ensures that non-specific amplification products are not falsely identified as integration events. The resulting positive reads were then mapped to the mm10 mouse genome using BWA-MEM. Integration events were summarized using a custom R-script (ggbio) to display as a karyogram.

Figure 4A:
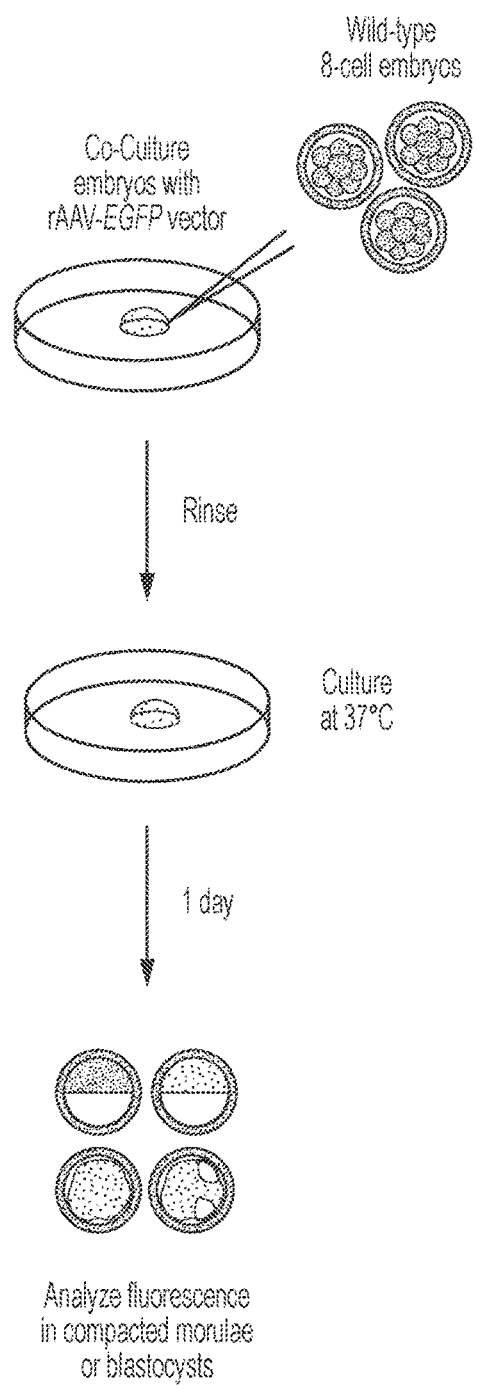
FIGS. 4A-4B show multiple rAAV serotypes can transduce intact pre-implantation embryos.
Figure 4B:
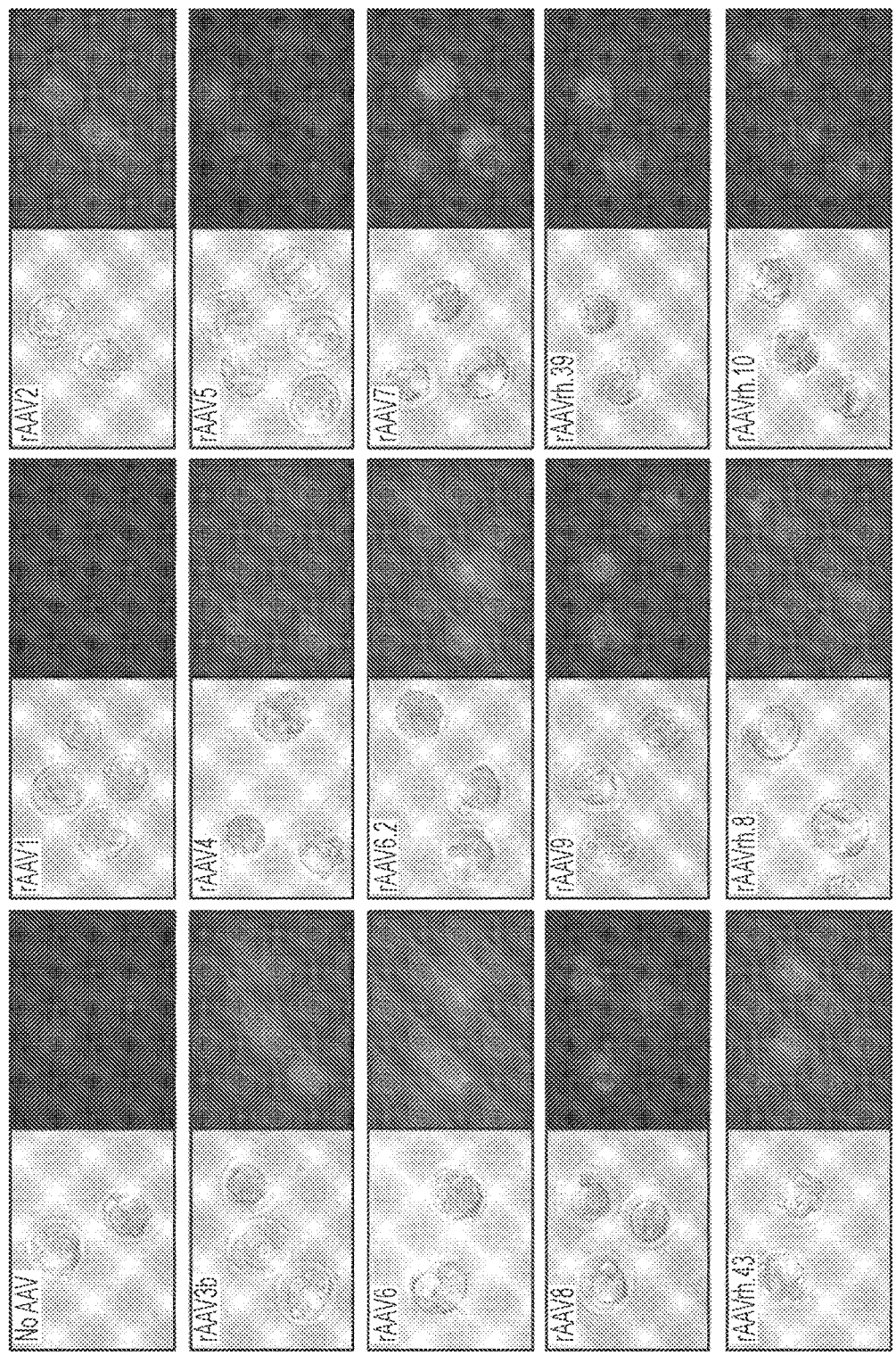

Example 1: rAAV Vectors Transduced Intact Pre-Implantation Embryos and Induced Gene-Editing rAAV Vectors Transduced Intact Mouse Embryos at Multiple Pre-Implantation Stages To determine if rAAV vectors can permeate the zona pellucida, the ability of 14 rAAV serotypes to transduce explanted pre-implantation embryos was evaluated. Intact eight-cell morulae were treated with a panel of rAAV serotypes packaged with an identical EGFP transgene (rAAV.CB6-EGFP) at a dosage of ~9.0×10$^9$ genome copies (GCs) and evaluated after one day in culture. EGFP fluorescence analysis showed that all of the serotypes tested were capable of transducing intact morulae (FIGS. 4A-4B, Table 2). Serotype 6 was one of the most effective AAVs, showing high embryo survival rate, and was therefore used in subsequent experiments. rAAV6.CB6-EGFP was also successfully utilized to transduce zygotes from two inbred strains (C57BL/6NJ and FVB/N) and one outbred strain (CD-1) with 100% efficiency (Table 3).

These results suggest that multiple AAV serotypes can transduce intact mouse embryos at multiple pre-implantation stages, irrespective of mouse strain.

TABLE 2

Analysis of multiple rAAV serotypes for transduction of morulae ex vivo.

| Serotype[a] | Number of treated embryos | Number of surviving[b] embryos (%) | Number of EGFP-positive embryos (%) | EGFP intensity[c] |
|---|---|---|---|---|
| rAAV1 | 8 | 7 (87) | 3 (43) | + |
| rAAV2 | 9 | 9 (100) | 9 (100) | + |
| rAAV3b | 9 | 4 (44) | 1 (25) | ++ |
| rAAV4 | 10 | 9 (90) | 2 (22) | ++ |
| rAAV5 | 9 | 6 (67) | 2 (33) | + |
| rAAV6 | 13 | 13 (100) | 13 (100) | ++++ |
| rAAV6.2 | 11 | 7 (64) | 7 (100) | +++ |
| rAAV7 | 16 | 14 (87) | 14 (100) | ++++ |
| rAAV8 | 17 | 14 (82) | 8 (57) | ++ |
| rAAV9 | 12 | 9 (75) | 2 (22) | ++ |
| rAAVrh.39 | 12 | 11 (92) | 7 (63) | ++++ |
| rAAVrh.43 | 15 | 13 (87) | 13 (100) | ++++ |
| rAAVrh.8 | 10 | 7 (70) | 4 (57) | ++ |
| rAAVrh.10 | 13 | 11 (85) | 9 (81) | + |
| no rAAV | 81 | 74 (91) | 0 (0) | n/a |

[a]Each rAAV serotype carries the same EGFP expressing cassette.
[b]Embryos that developed to compacted morula or blastocyst stage after 1-day in culture.
[c]EGFP intensity was determined relative to non-treated control embryos and evaluated by two observers.

TABLE 3

Transduction efficiency of zygotes from different strains of mice with rAAV6-EGFP.

| Genetic background | Treatment | Number of treated zygotes | Number of surviving[b] embryos (%) | Number of EGFP-positive embryos (%) |
|---|---|---|---|---|
| C57BL/6J | rAAV6-EGFP[a] | 30 | 30 (100) | 30 (100) |
|  | no rAAV | 8 | 5 (63) | 0 (0) |
| FVB/N | rAAV6-EGFP | 24 | 16 (67) | 16 (100) |
|  | no rAAV | 12 | 11 (92) | 0 (0) |
| CD-1 | rAAV6-EGFP | 9 | 9 (100) | 9 (100) |
|  | no rAAV | 8 | 7 (88) | 0 (0) |

Figure 5A:
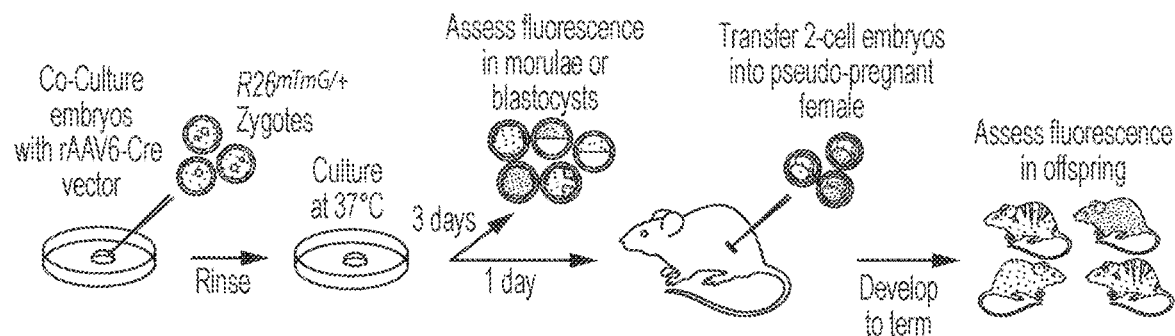
Figure 5B:
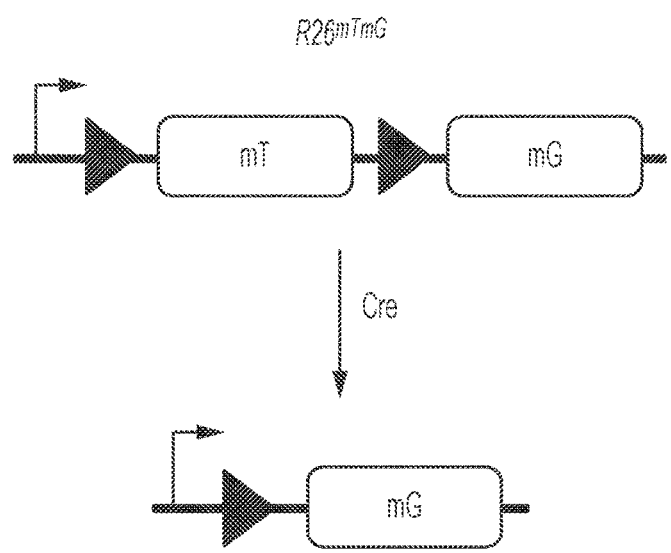
Figure 5C:
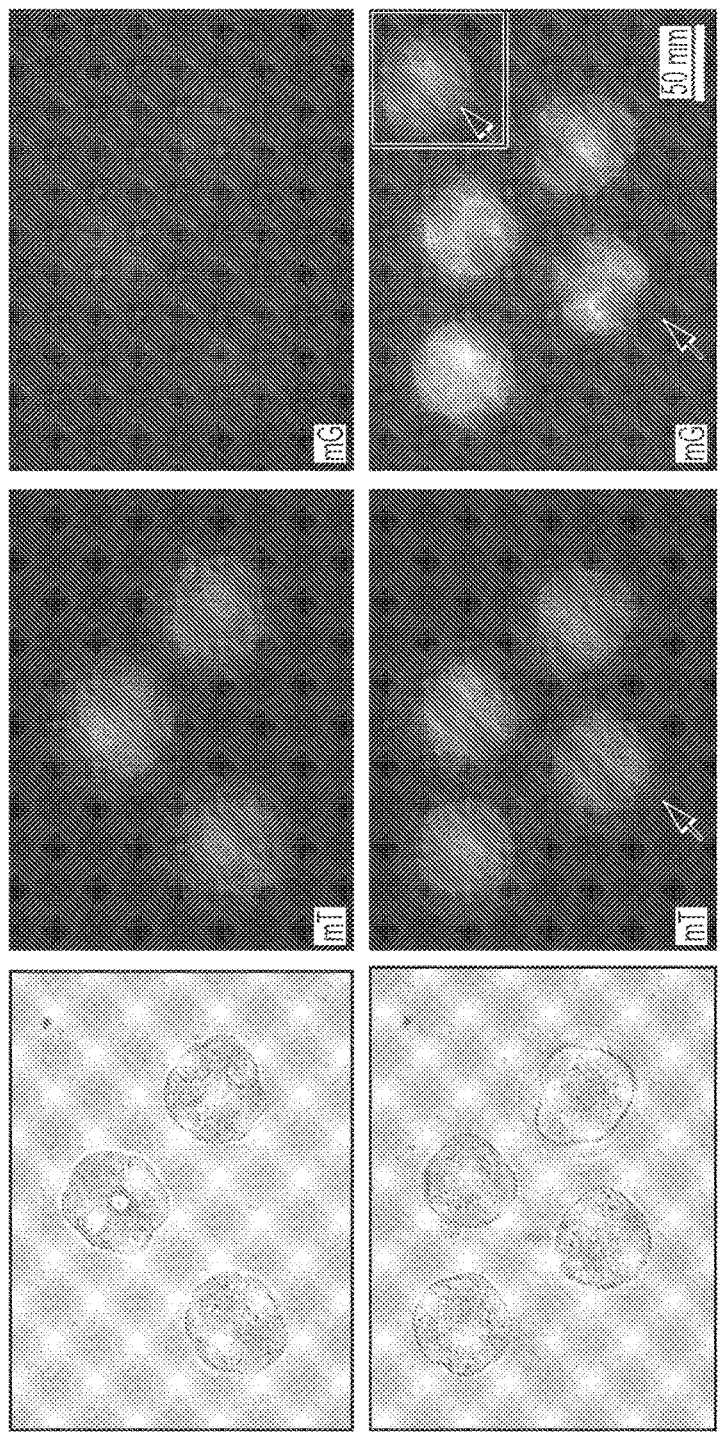
Figure 5E:
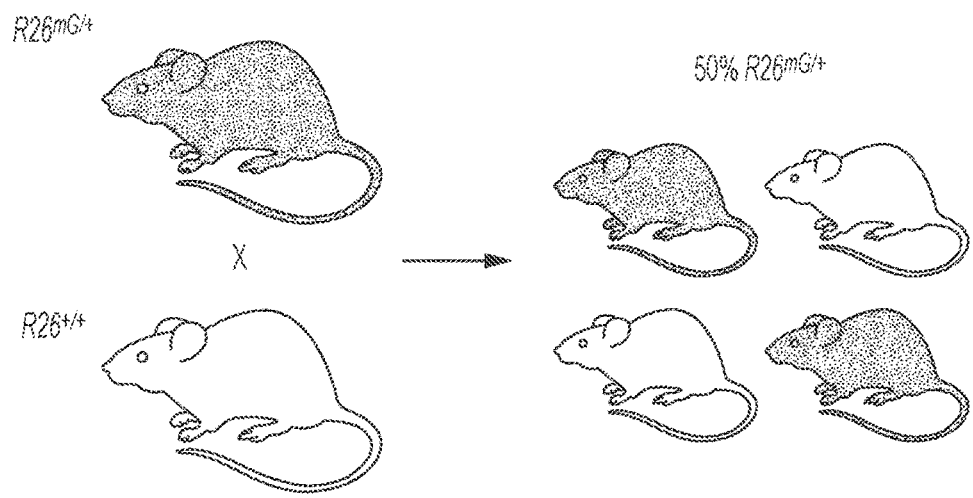
Figure 5F:
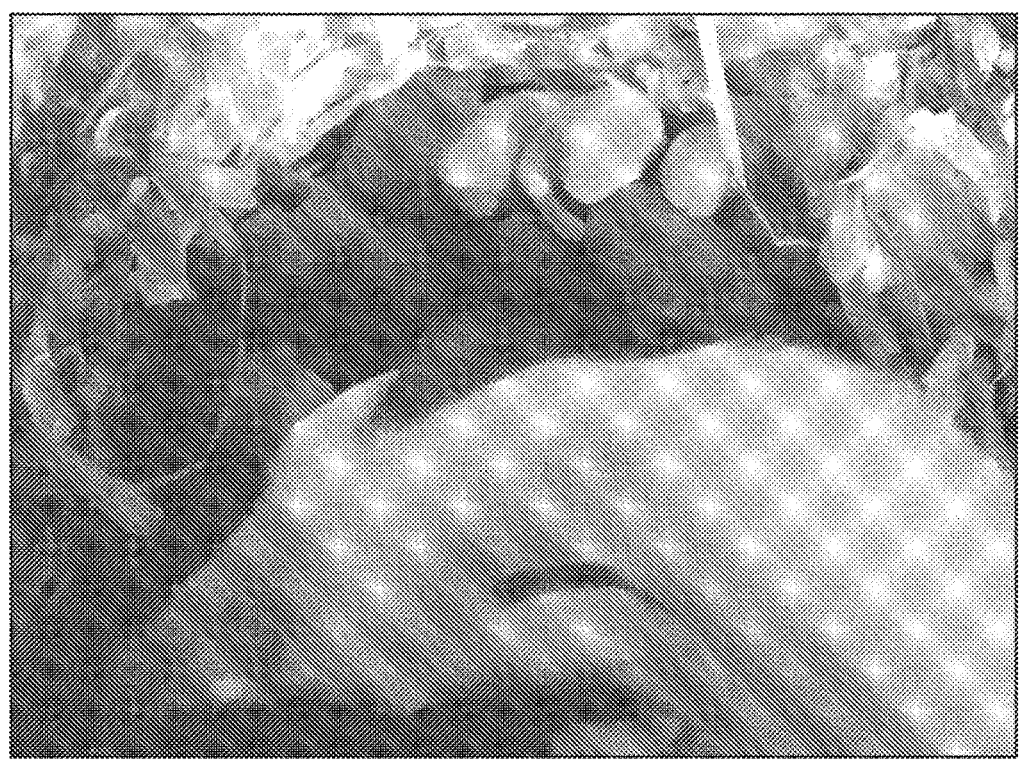
Figure 6:
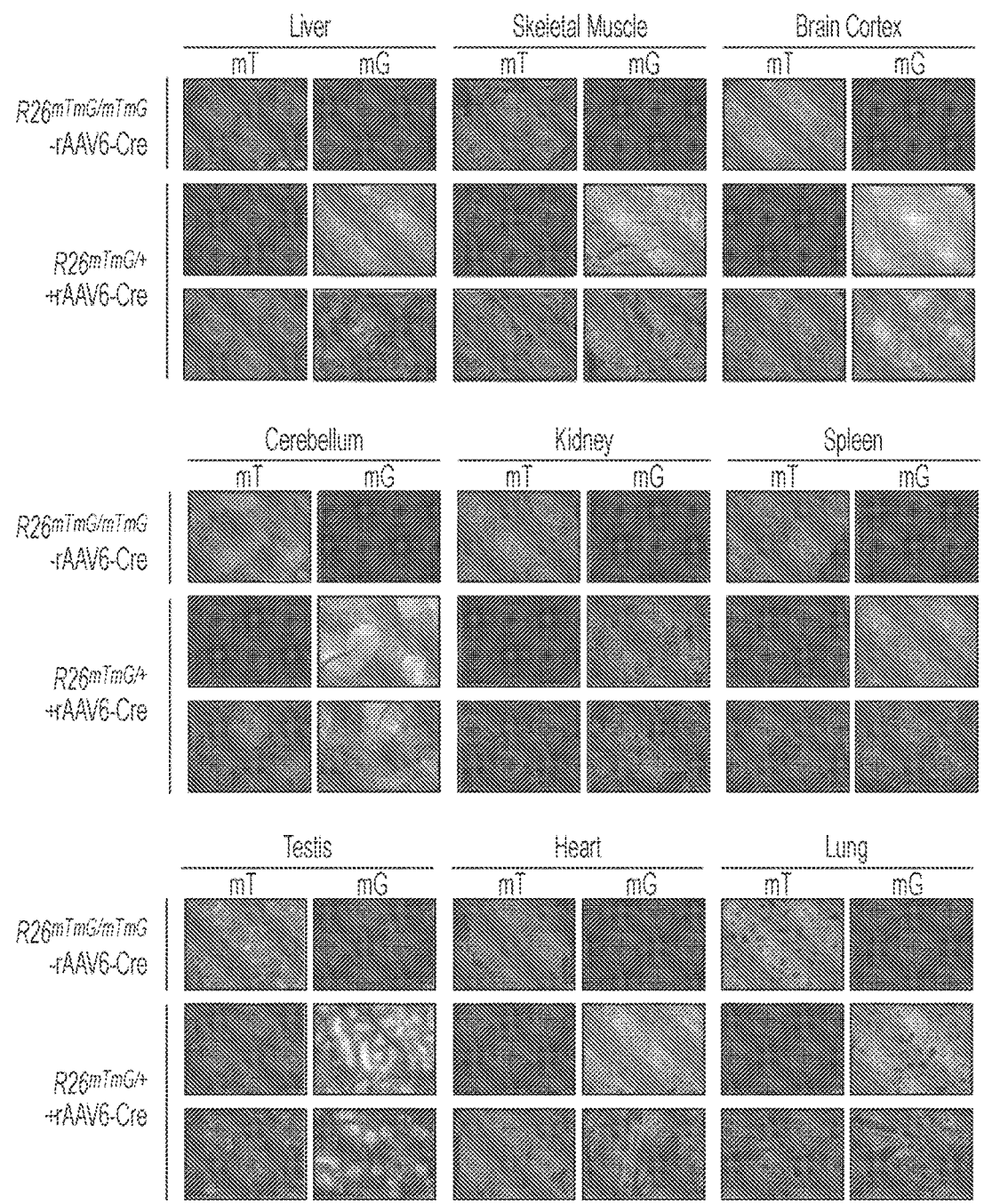
FIG. 6 show histological analysis of tissues of adult R26mTmG reporter mice transduced with rAAV6-Cre at zygote stage. Representative fluorescence images of tissue cryosections from a non-transduced control R26mTmG/mTmG mouse (top rows), R26mTmG/+ mice transduced with rAAV6-Cre with complete Cre recombination (middle rows) and R26mTmG/+ mice transduced with rAAV6-Cre with partial Cre recombination (bottom rows). Derivatives of all three germ layers are shown. Slight fluorescence observed in the middle row of testis section is the result of auto-fluorescence. This was also observed in sections of control testis (not shown).

[a]Experimental embryos were exposed to viral particles for 5-6 h.
[b]Embryos that developed to compacted morula or blastocyst stage after 3 days in culture.

rAAV Vectors Delivered Cre Recombinase in Pre-Implantation Embryos to Induce Gene Recombination To demonstrate the feasibility of rAAVs to mediate germline transgenesis, R26$^{mTmG}$ heterozygous zygotes were transduced with rAAV6.CB6-Cre (rAAV6-Cre) (FIG. 5A). The R26$^{mTmG}$ reporter drives ubiquitous expression of membrane-bound tdTomato fluorescent protein. After Cre recombination, the tdTomato gene is excised and the EGFP gene is expressed (FIG. 5B). After treatment with rAAV6-Cre and three days in culture, the majority of R26$^{mTmG}$ zygotes (32/38, 84%) underwent Cre recombination (FIG. 5C). In addition, transfer of treated embryos into pseudopregnant females resulted in 37 out of 38 pups (97%) showing green fluorescence (FIG. 5D, Table 4). Two of these animals produced multiple green fluorescent pups after matings to wild-type CD-1 mice, at a frequency close to the expected 50% Mendelian ratio (7/15 and 6/14) (FIGS. 5E-5F).

These results show that rAAV particles can efficiently deliver Cre recombinase to pre-implantation embryos to induce genetic recombination that is germline transmissible.

TABLE 4

Ex vivo Cre recombination after transduction of R26$^{mTmG}$ zygotes with rAAV6-Cre.

| Number of treated zygotes | Time of Analysis | Number of surviving embryos[a] or pups (%) | Number of EGFP-positive embryos or pups (%) | Number of mosaic embryos or pups (%) |
|---|---|---|---|---|
| 40 | E3.5 | 38 (95) | 32 (84) | 5 (16) |
| 74 | P2[b] | 38 (51) | 37 (98) | 15 (37) |

Figure 7A:
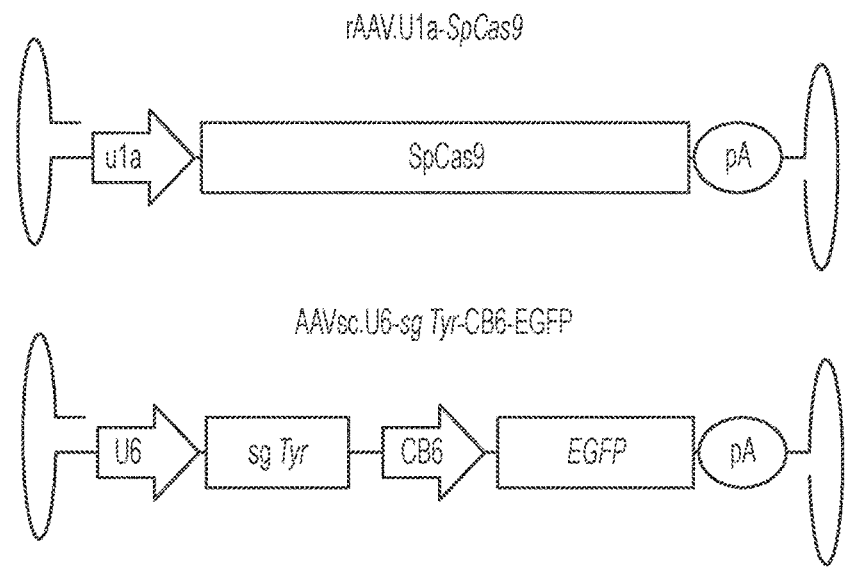
Figure 7B:
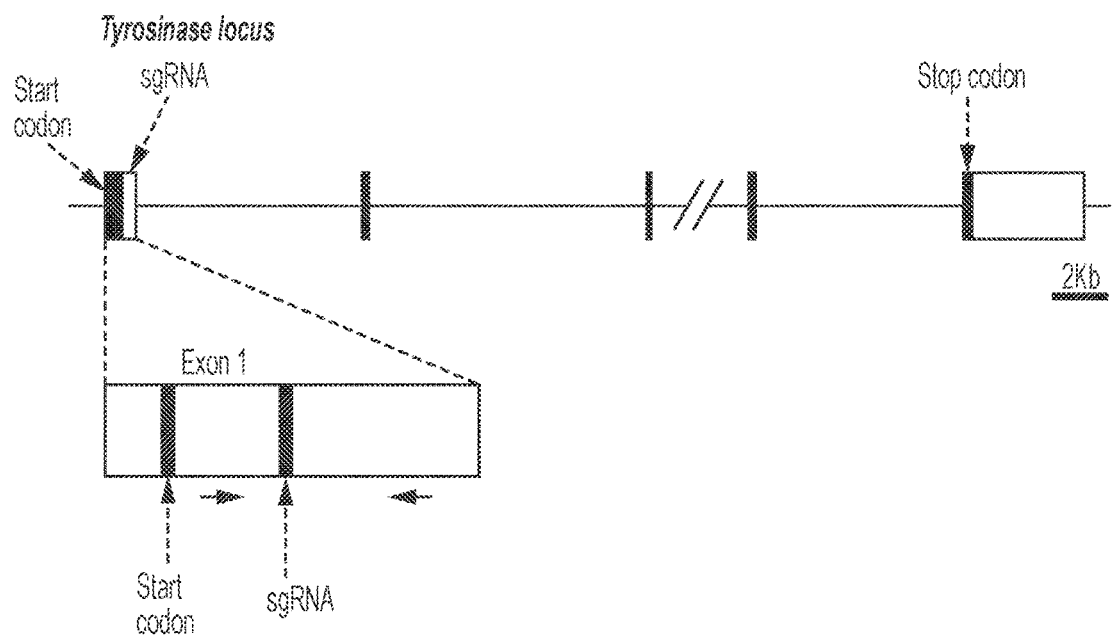
Figures 7D, 7E:
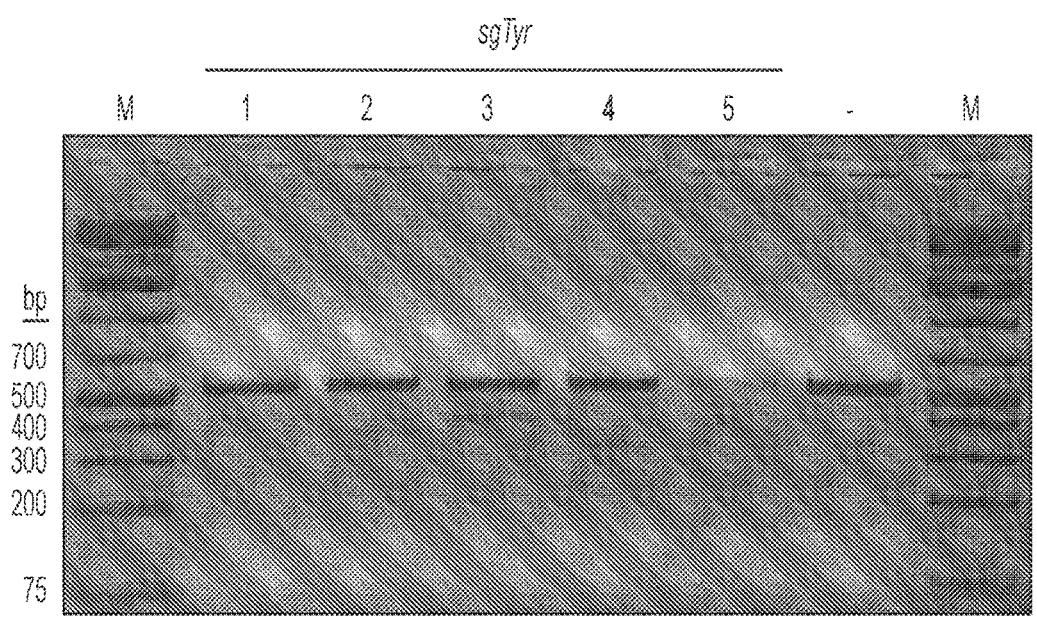

[a]Embryos that developed to compacted morula or blastocysts after three days in culture.
[b]Embryos were cultured overnight, transferred into pseudopregnant females and analyzed at post-natal day 2.

rAAV Vectors Delivered Cas9 and sgRNA Transgenes into Pre-Implantation Embryos to Induce Gene Editing The ability of rAAV vectors to deliver Cas9 and sgRNA transgenes into intact embryos to drive genome editing was assessed. Tyrosinase (Tyr), a gene essential for the synthesis of melanin was targeted. This strategy provides an easy way to visualize gene editing events, since the bi-allelic inactivation of Tyr leads to albinism. To express Cas9, rAAV6.U1a-SpCas9 (rAAV6-Cas9), a vector containing the *Streptococcus pyogenes* Cas9 (SpCas9) gene driven by the mouse U1a snRNA promoter was used. A second vector, rAAV6.U6-sgTyr-CB6-EGFP (rAAV6-sgTyr), was used to drive the expression of a single-guide RNA (sgRNA) under the control of the U6 promoter (FIG. 7A). The rAAV6-sgTyr vector also contains a cassette expressing EGFP under the control of the CB6 promoter to monitor transduction efficiency. Five sgRNAs targeting Tyr exon 1 were screened, and the most effective guide, which targets a site located between the Tyr$^{c-2J}$ mutation and the classic Tyr$^c$ albino point mutation, was used for subsequent experiments (FIGS. 7B-7E).

Figure 1B:
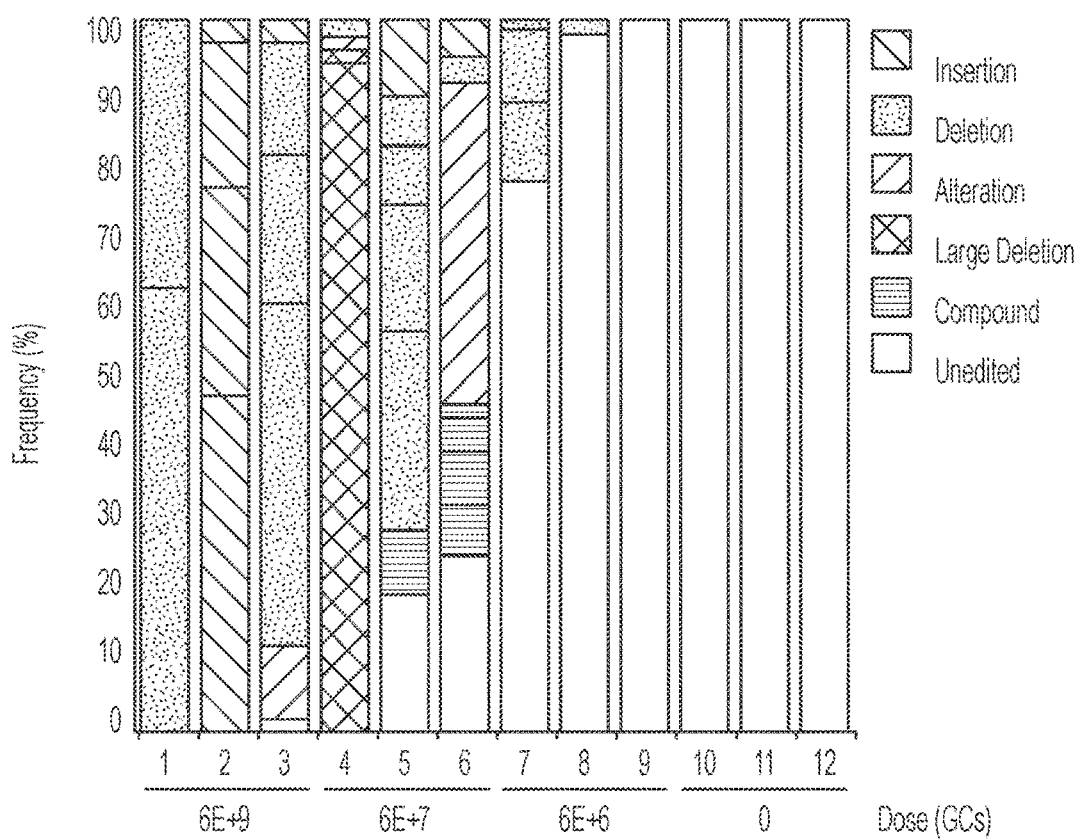
Figure 1C:
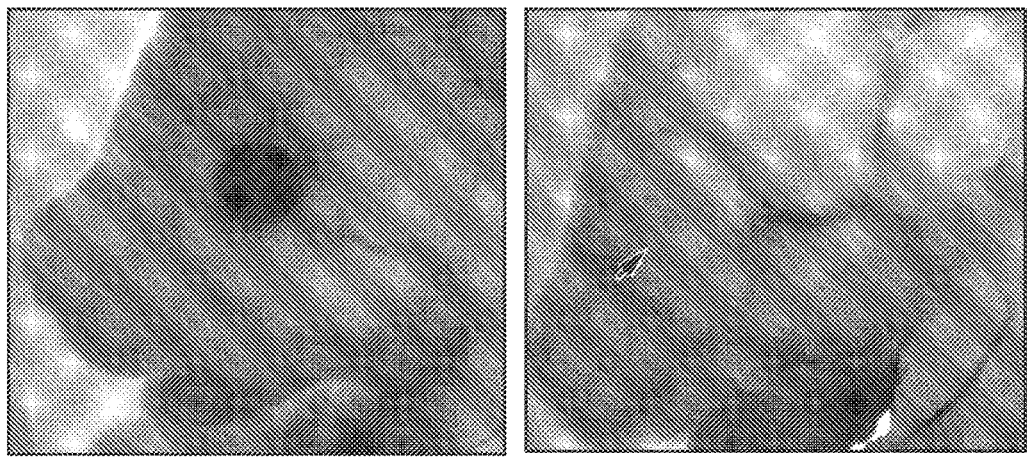
Figure 1D:
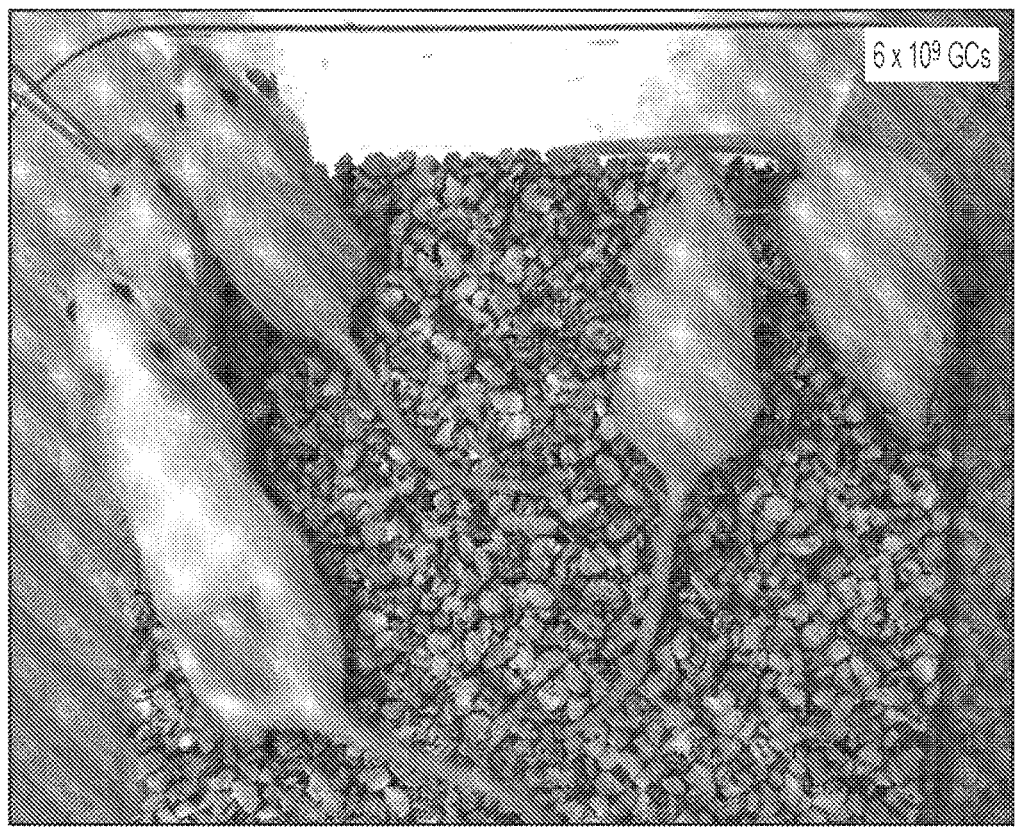
Figure 8A:
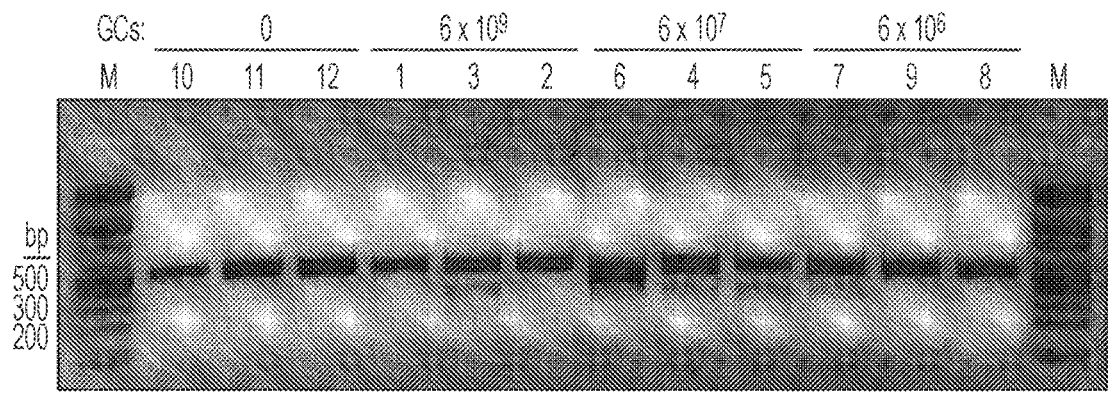
FIGS. 8A-8C show analysis of Tyr gene editing in mouse embryos using sgRNA4.
Figure 8B:
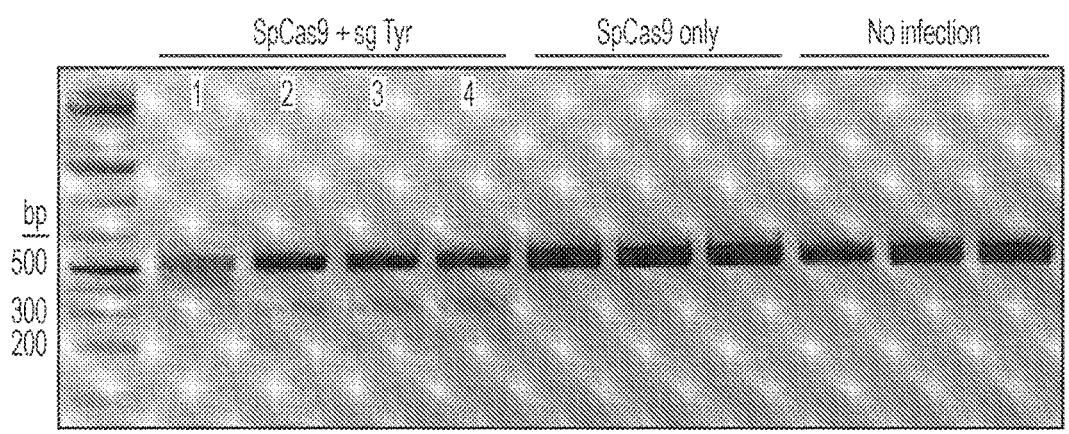
Figure 8C:
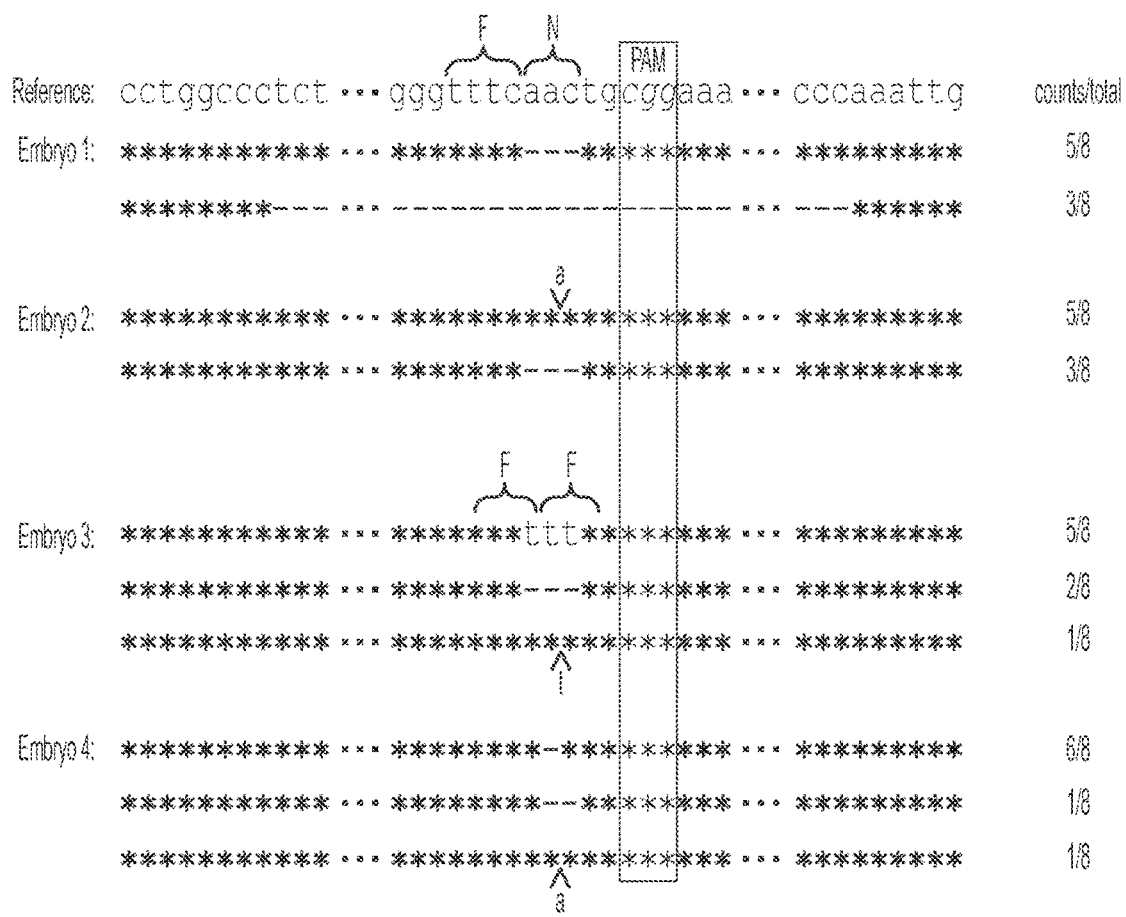

C57BL/6NJ zygotes were infected with a 1:1 mixture of rAAV6-Cas9 and rAAV6-sgTyr at three vector dosages (6×10$^9$, 6×10$^7$, and 6×10$^6$ GCs) and cultured for three days until they reached the compacted morula or blastocyst stages (FIG. 1A). The prevalence of gene editing in embryos was examined by T7EI nuclease analysis and single molecule, real-time (SMRT) sequencing (FIG. 8A and FIGS. 9A-9B). Evidence of gene editing in all experimental groups was found. Sequencing data indicated that the penetrance of gene editing was dose-related (FIG. 1B). Embryos treated with 6×10$^9$ GCs dose exhibited >99% editing, while embryos treated with 6×10$^6$ GCs showed <23% editing. Embryos treated with the intermediate dose (6×10$^7$ GCs) showed the highest diversity of indel types among the set (upwards of eight types within a single embryo) (FIG. 1B). These results suggest that higher dosages lead to earlier gene editing events while lower dosages lead to editing at later stages of development, and consequentially, a greater variety of mutations. In fact, the presence of eight different mutations in two of the embryos from the mid-range dosage suggests that CRISPR-Cas9 activity occurs at or beyond the 4-cell stage.

Figure 1E:
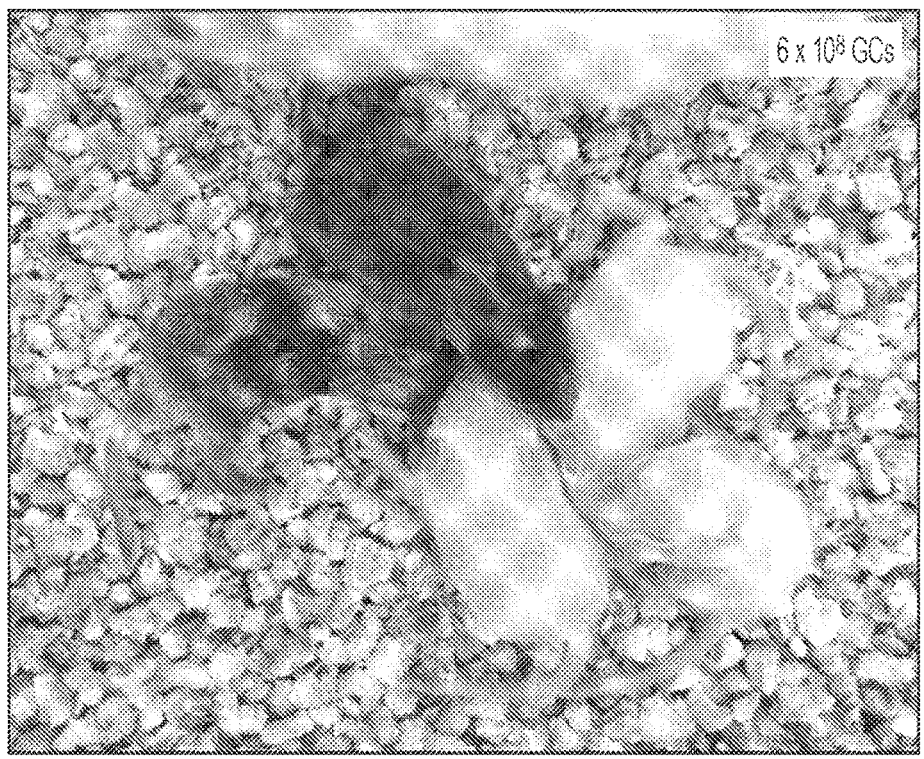
Figure 10:
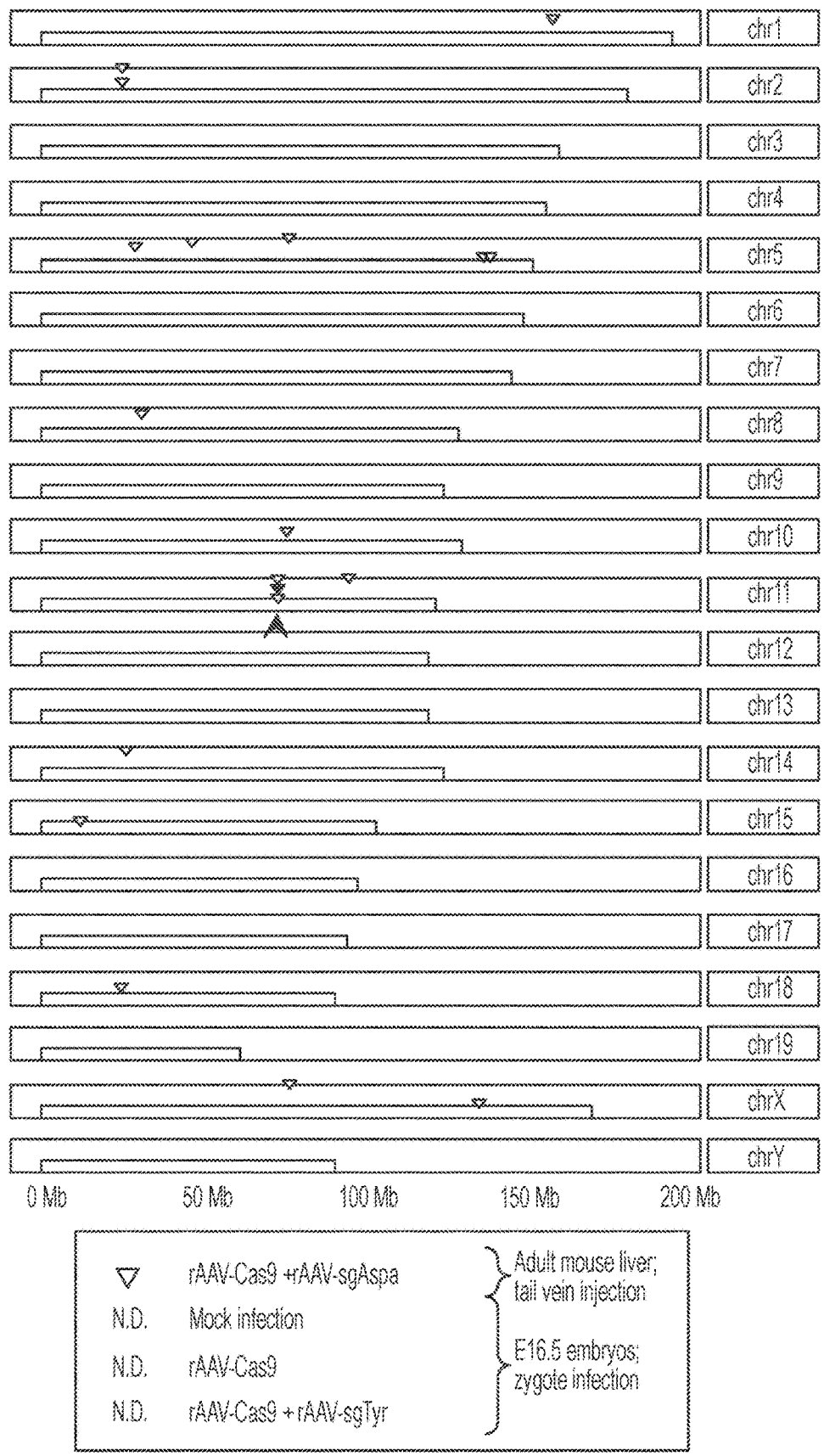
FIG. 10 show treatment of embryos with rAAV-Cas9/sgTyr does not lead to detectable levels of rAAV integration. Karyogram display showing the detection of integration events across the mouse genome in a control sample targeted at the Aspartoacylase (Aspa) gene. Tail vein injection of rAAV9-Cas9/sgAspa into an adult mouse results in the detection of multiple integration events in the liver (triangles, n=1), serving as positive control for the rAAV integration analysis method. Location of the Aspa gene on chromosome 11 is indicated by the arrowhead. To detect possible rAAV integration following zygote infection, DNA from whole E16.5 embryos was analyzed. Mock infection, infection with Cas9 vector alone, and coinfection with Cas9 and sgTyr vectors did not result in detectable levels of integration when analyzed in E16.5 embryos (N.D.=not detected). n=3.
Figures 11A, 11B:
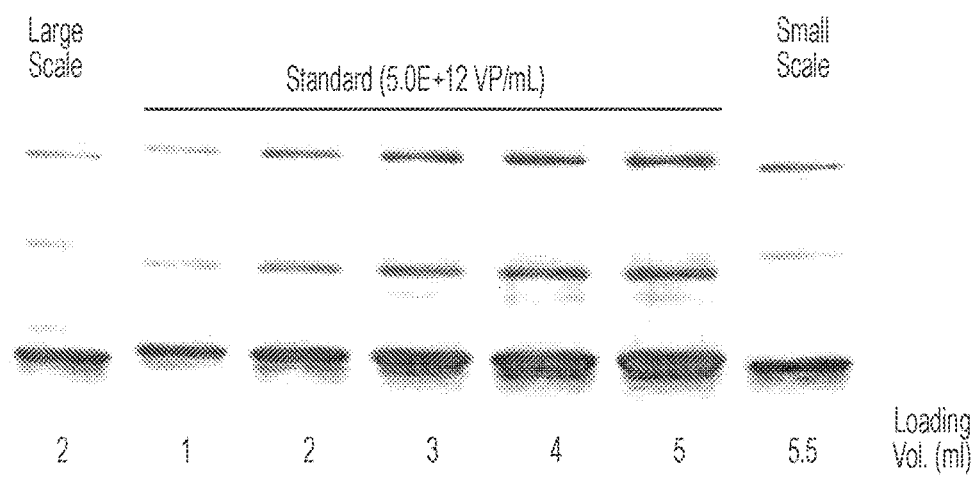
FIGS. 11A-11D show genome editing using small scale preparation of rAAV vector.
Figures 11C, 11D:
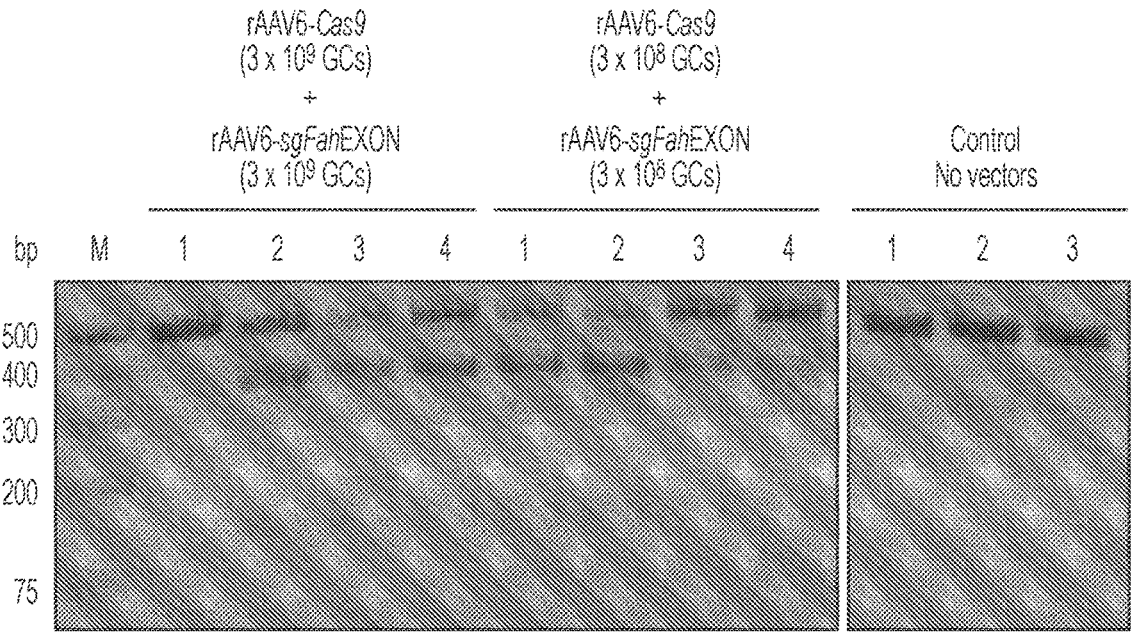
Figure 12:
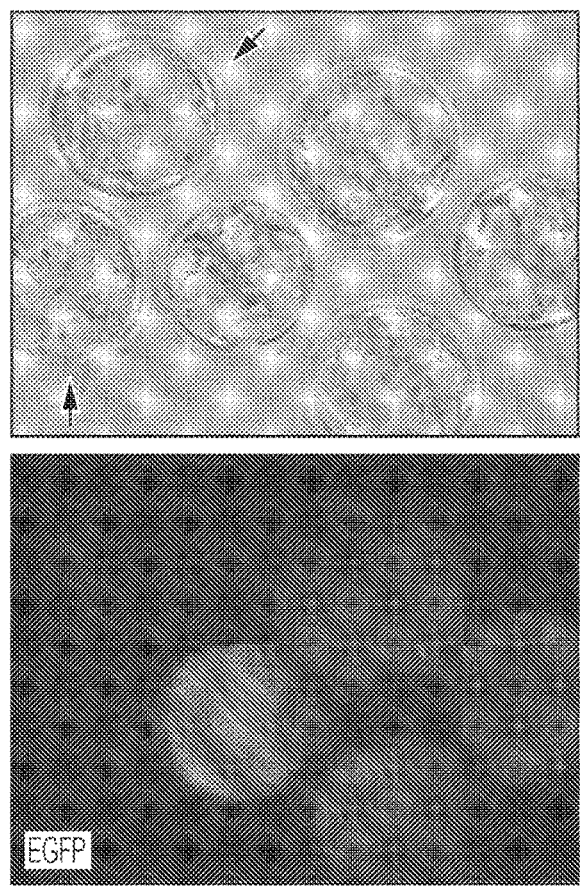
FIG. 12 shows fluorescence analysis of control (arrowheads) and transduced blastocysts with rAAV1-EGFP at the 8-cell stage.
Figure 13A:
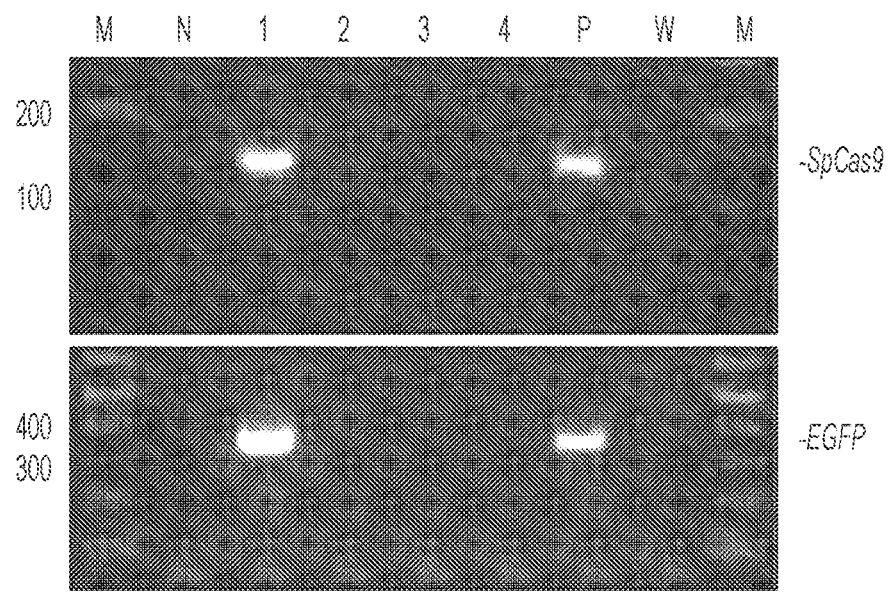
FIGS. 13A-13D show detection of rAAV vector integration into the Tyr gene.
Figure 13B:
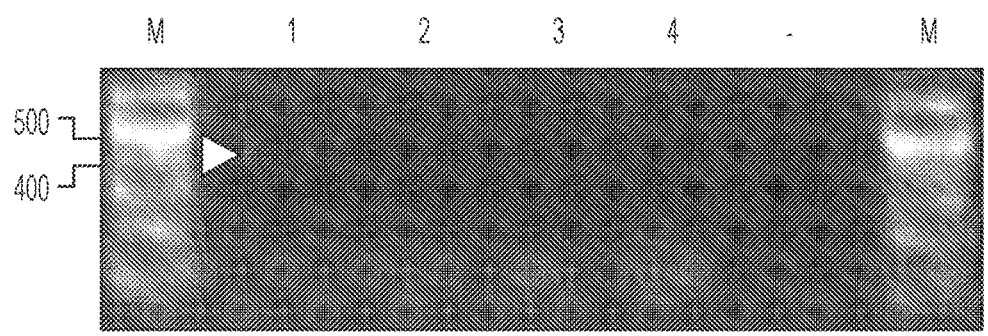
Figure 13C:
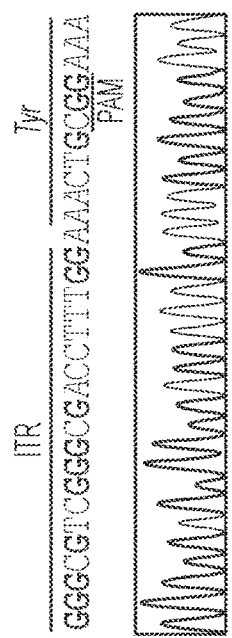
Figure 13D:
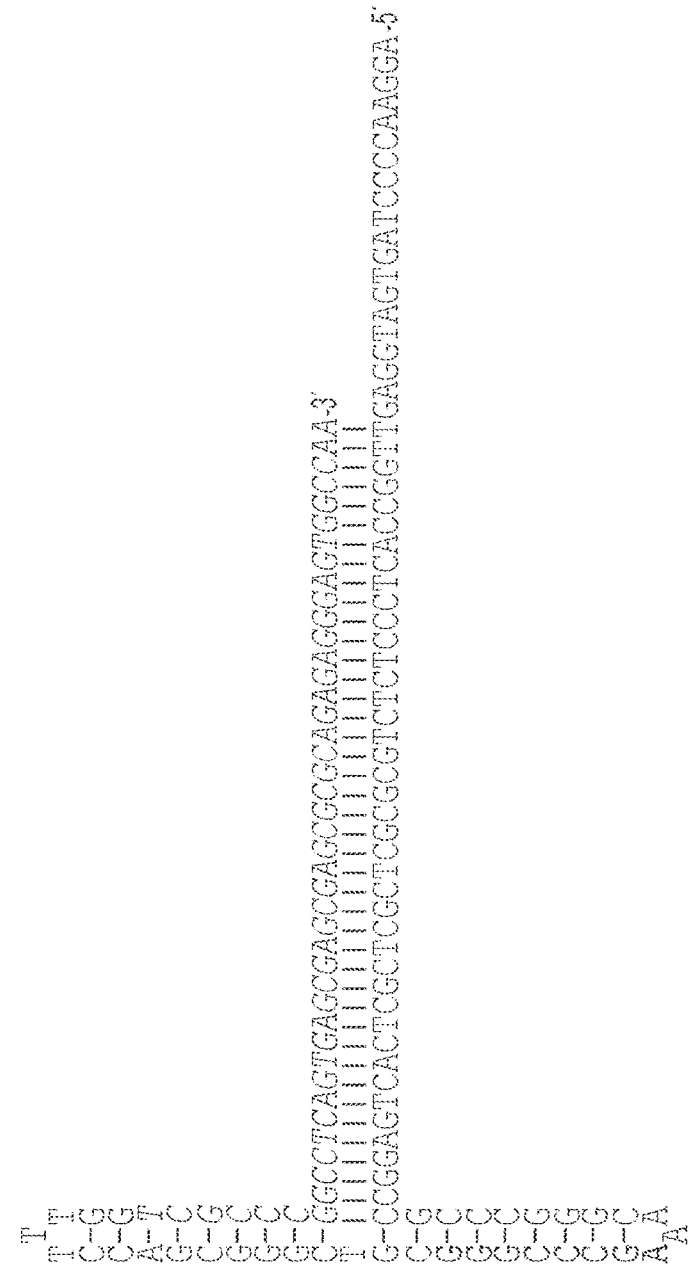
Figures 14A, 14B:
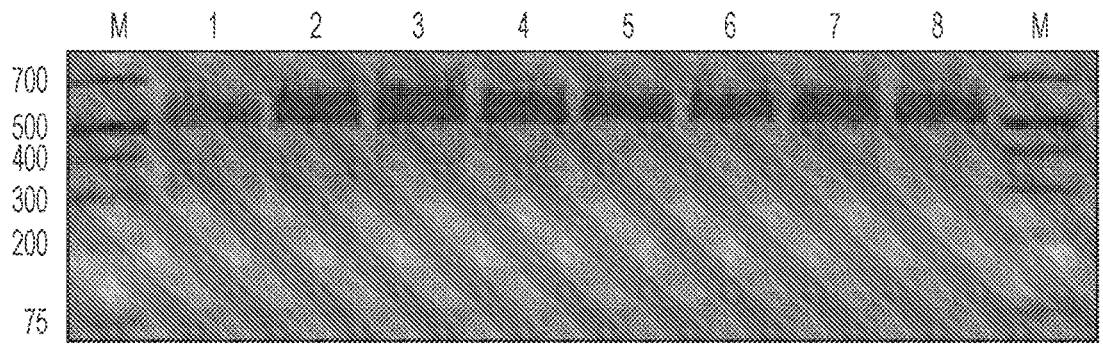
FIGS. 14A-14B show analysis of Tyr gene editing in mice generated by in vivo delivery of CRISPR-Cas9 vectors into the oviduct of E0.5 pregnant female.

To determine the ability of rAAV-CRISPR-Cas9 treated embryos to develop to birth, transduced zygotes were cultured overnight and those that advanced to the 2-cell stage were transferred into pseudo-pregnant recipients. Embryos at E16.5 and newborns were assessed for the absence of eye pigmentation. One-week old pups or older were also evaluated for albino coat color (Table 5). The frequency of mutation was 100% in embryos and newborns for the 6×10$^9$ GCs dosage group. All of the pups generated at this concentration were albino (FIGS. 1C-1D, FIGS. 8B-8C, and Table 5). Zygotes treated with 6×10$^8$ GCs also resulted in 100% editing frequency but produced only 80% albino pups (FIG. 1E and Table 5). The editing efficiency dropped to 25% of embryos and 20% of newborns at 6×10$^7$ GCs and no edited animals were detected from the 6×10$^6$ GCs treatment group. Integration events in rAAV6-Cas9 or rAAV6-Cas9+ rAAV6-sgTyr treatment groups (FIG. 10) were not detected using linear amplification mediated-PCR (LAM-PCR) and SMRT sequencing.

TABLE 5

Ex vivo gene editing after transduction of C57BL/6NJ zygotes with CRISPR-Cas9 rAAV vectors.

| rAAV dosage (GCs) | Number of zygotes transferred | Time of Analysis | Number of embryos or pups recovered (%) | Tyr edited embryos or pups (albino)$^a$ | Tyr editing frequency (%) |
|---|---|---|---|---|---|
| 6E+9 | 17 | E16.5 | 7 (41) | 7 (6) | 100 |
|  | 28 | P10 | 5 (18) | 5 (5) | 100 |
| 6E+8 | 17 | E16.5 | 9 (53) | 7 (7) | 78$^b$ |
|  | 46 | P10 | 10 (22) | 10 (8) | 100 |
| 6E+7 | 35 | E16.5 | 16 (48) | 4 (0) | 25 |
|  | 83 | P10 | 25 (30) | 5 (3) | 20 |
| 6E+6 | 16 | P10 | 6 (38) | 0 | 0 |
| 0 | 55 | P10 | 19 (35) | 0 | 0 |

$^a$Gene editing evidence obtained by assessing eye pigmentation in embryos or coat color in pups and by genome analysis.
$^b$Two pigmented embryos were not assessed for gene editing at the genomic level.

Figure 1F:
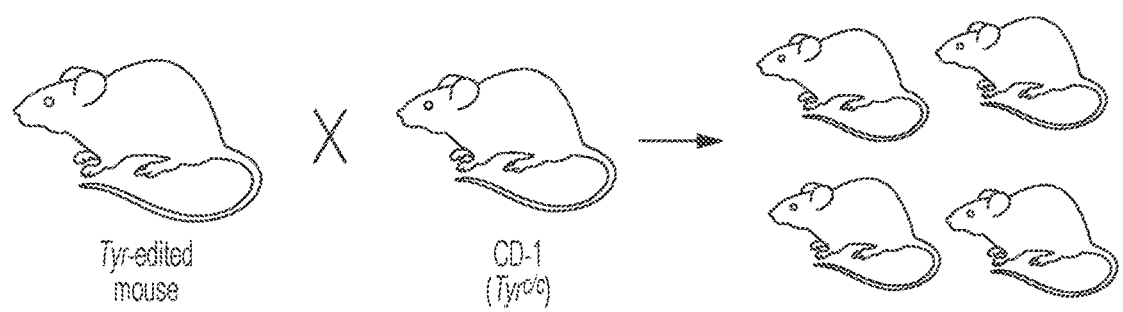
Figure 1G:
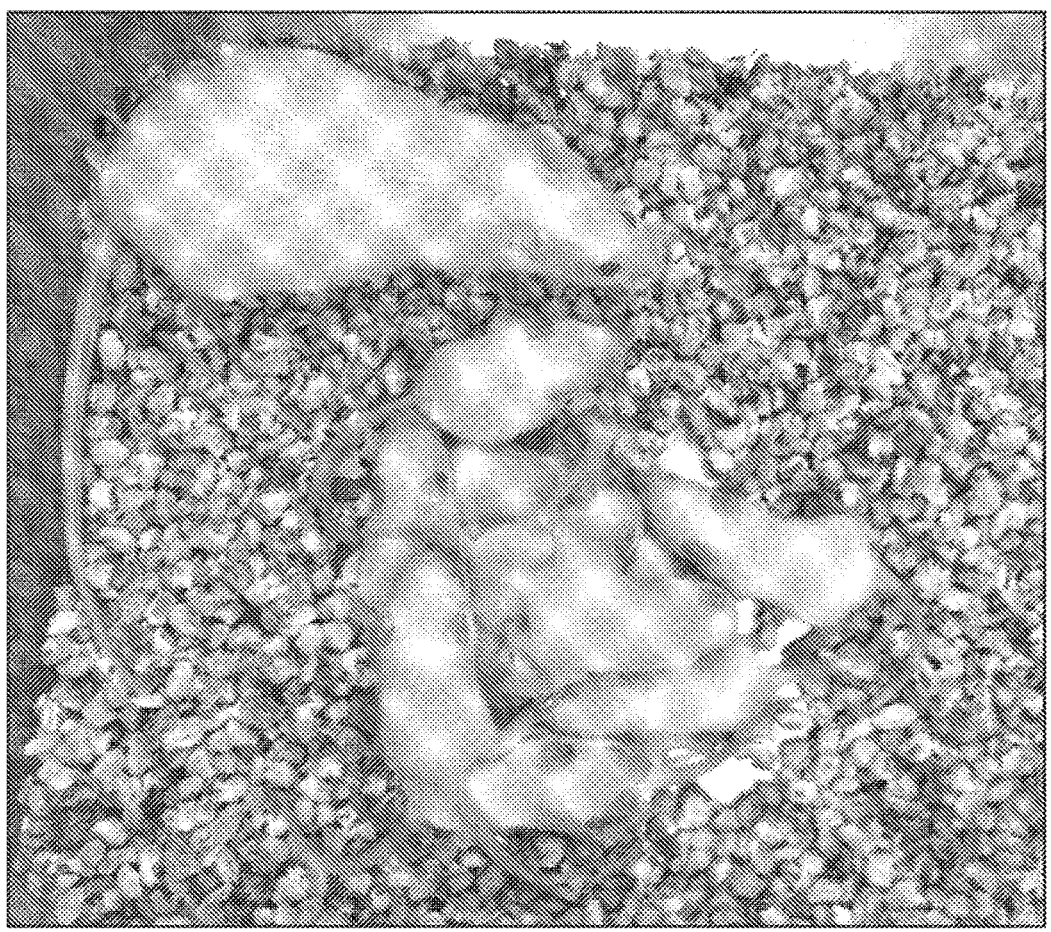

To test for germline transmission, one albino male derived from the 6×10$^9$ GCs dosage group was mated to an albino CD-1 female (Tyr$^{c/c}$). From this cross, 11 healthy albino pups were obtained, indicating successful germline transmission (FIGS. 1F-1G).

Taken together, these results show that gene editing mediated by rAAV delivery of Cas9 and sgRNA transgenes is highly efficient and can result in germline transmission. Genome Editing in Mouse Embryos Using Small Scale Preparation of rAAV Vectors The experiments shown above were achieved using a traditional large-scale rAAV vector production procedure that requires specialized equipment and skills. As disclosed herein, the quality and titers of rAAVs produced using a simplified protocol and in a conventional laboratory setting also efficiently generated indels in the Tyr and the Fumarylacetoacetate hydrolase (Fah) gene loci (FIGS. 11A-11D). Thus, genome editing can be done efficiently using small-scale preparation of rAAV vectors and can be applied to more than one genomic locus.

Example 2: rAAV Vectors Transduced Intact Pre-Implantation Embryos and Induced Homology-Directed Repair (HDR)

Figure 2A:
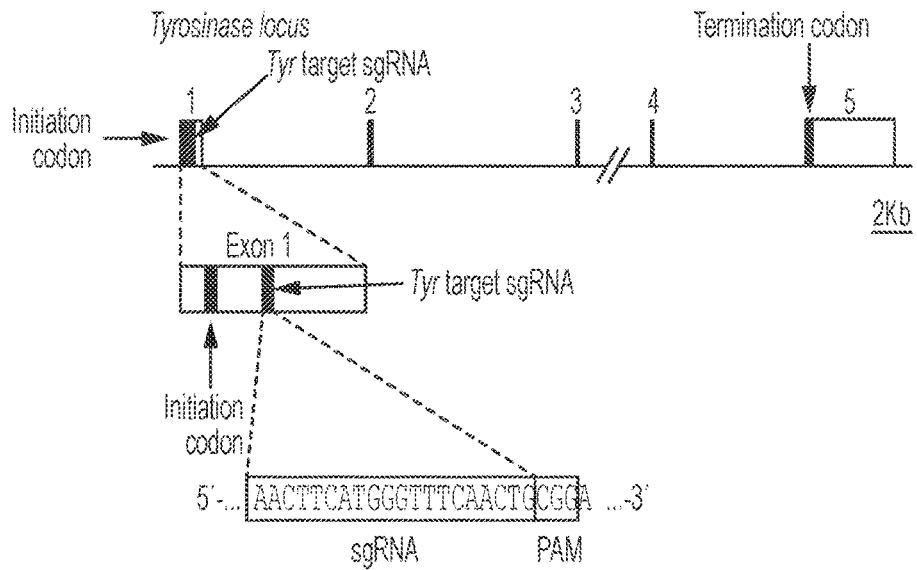
Figure 2B:
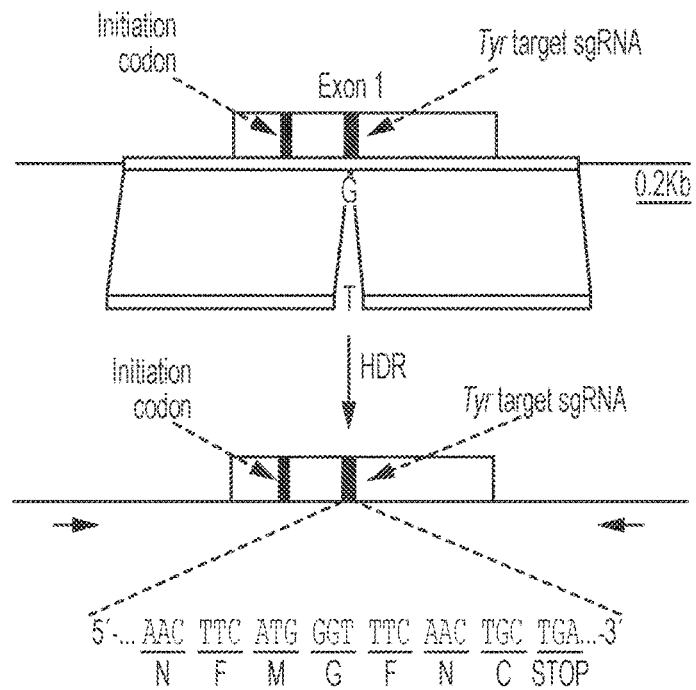
Figure 2C:
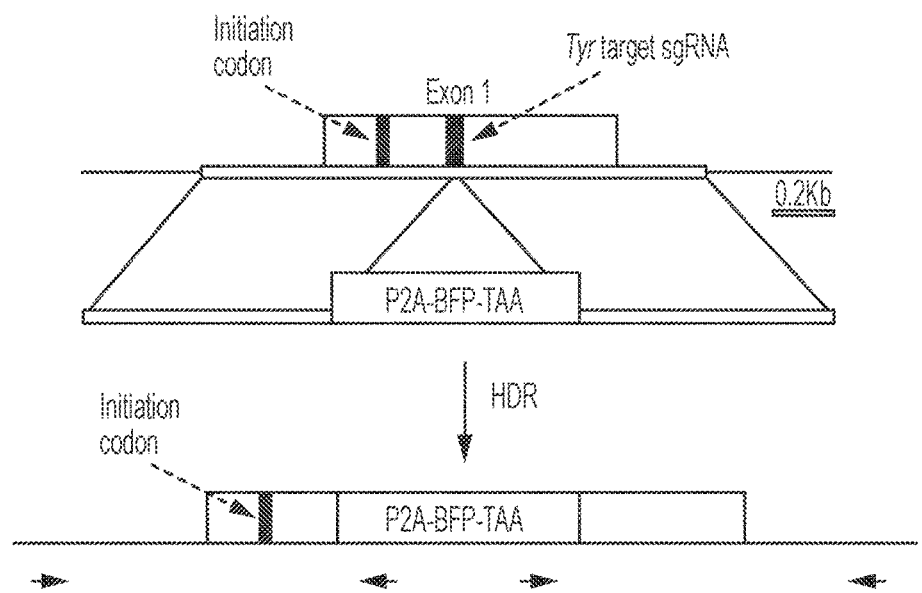
Figure 2D:
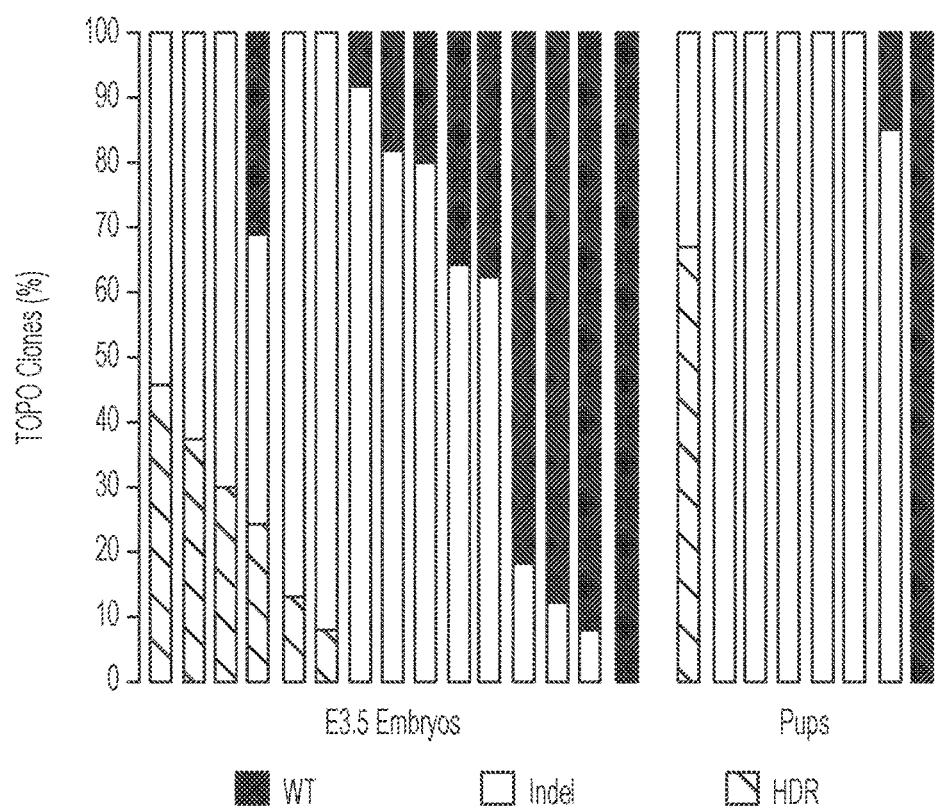

An important feature of genome editing protocols is to generate precise genetic changes. Therefore, the ability of rAAV vectors to induce homology-directed repair (HDR) was tested. To achieve this goal, two donor rAAV vectors were designed for use in combination with rAAV6-SpCas9 and rAAV6-sgTyr vectors. The donor vectors carry a DNA construct that consists of ~800-bp homology arms on either side of the sgTyr target site (FIGS. 2A-2C). A single nucleotide transversion (SNT) strategy was used to generate a premature stop codon in Tyr for an albino phenotype (FIG. 2B). A donor vector was also designed to introduce a 771 bp blue fluorescent protein (BFP) cassette containing a porcine teschovirus-1 2A peptide and a stop codon (P2A-BFP-TAA) (FIG. 2C). Zygotes were incubated with these three vectors, rinsed in fresh media, and cultured for three days until the compacted morulae or blastocyst stage for analysis. DNA obtained from SNT embryos was subjected to PCR and TOPO sequencing to determine the frequency of the G to T transversion. Results demonstrated that 40% of all E3.5 embryos analyzed were SNT-positive using a low dose of rAAVs, and that the HDR frequency in individual SNT-positive embryos ranged from 8-45% (FIGS. 2D and 2F). One live pup was identified with 68% SNT after analysis of DNA extracted from tail snip and ear punch in this animal (FIG. 2D).

Figure 2E:
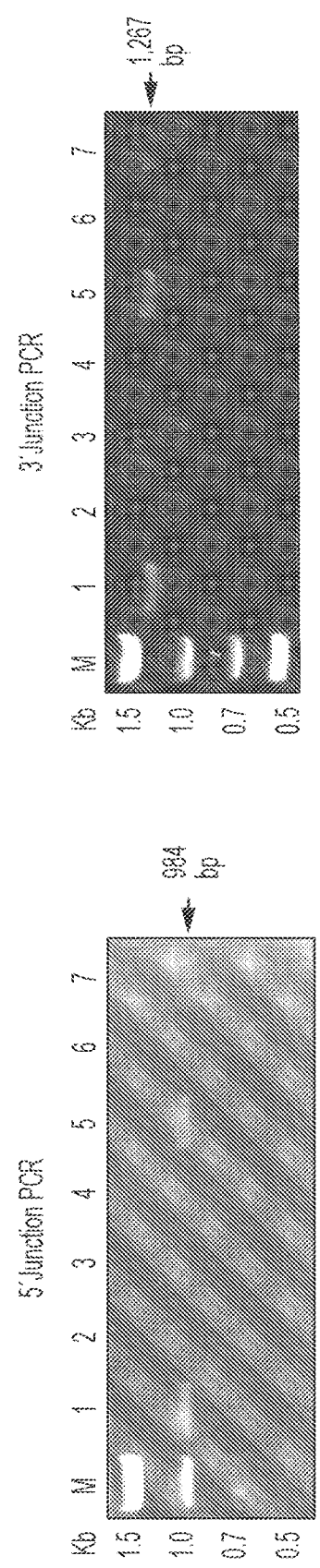

The insertion of the BFP cassette was determined using PCR (FIG. 2E), and the resulting amplicons were sequenced to confirm the recombination event (data not shown). The frequency of BFP insertion was as high as 57%, depending on the vector dosage (FIG. 2F). Two live pups were generated carrying the BFP insertion (2/24) as determined by PCR analysis. One of these mice was assessed for germline transmission by crossing to wild-type females. Thirty five percent (9/26) of the pups generated inherited the BFP insertion.

These experiments indicate that it is feasible to induce HDR-mediated genome editing in early embryos with high efficiency by transduction of three independent rAAV vectors and generate transgenic mice that exhibit germline transmission.

Example 3: rAAV Vectors Transduced Intact Pre-Implantation Embryos and Induced Homology-Directed Repair (HDR)

Figure 3A:
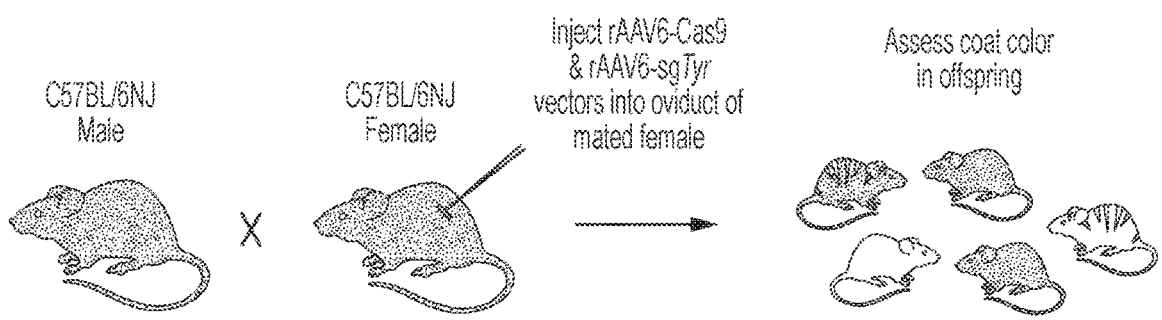
Figure 3B:
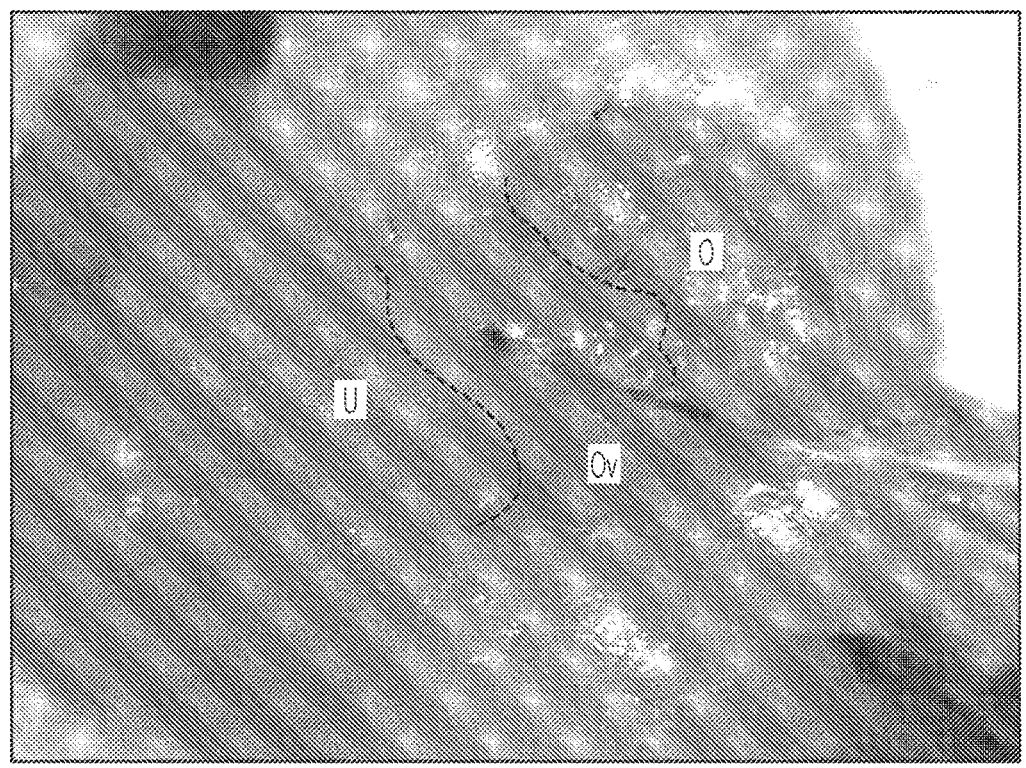
Figure 3C:
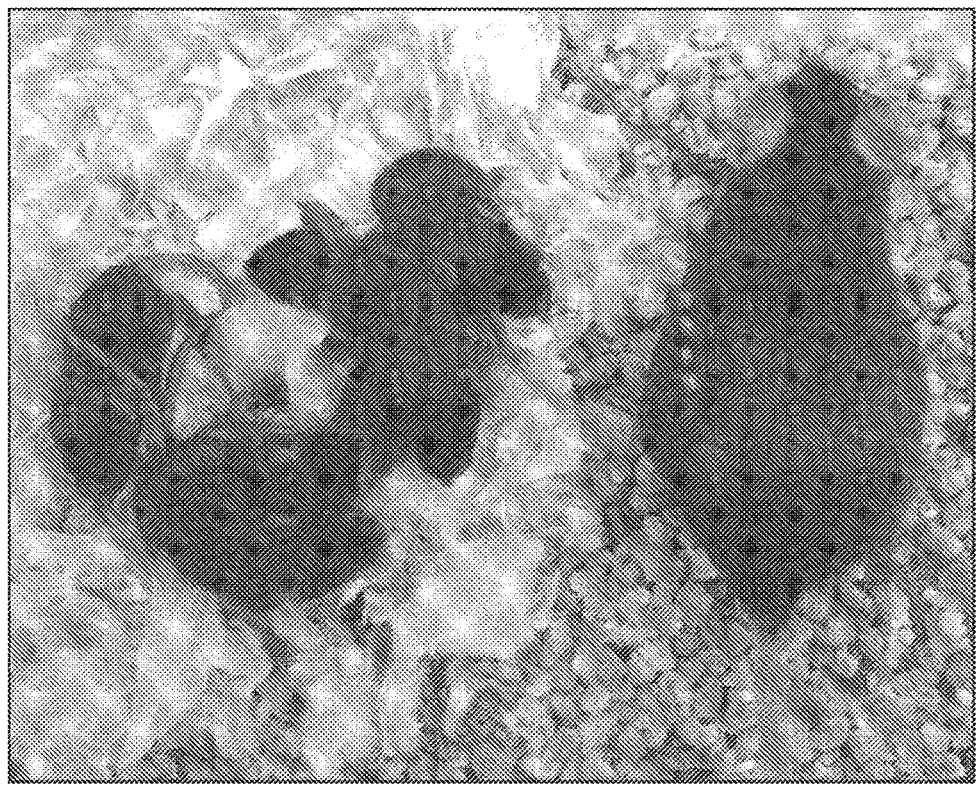
Figure 3D:
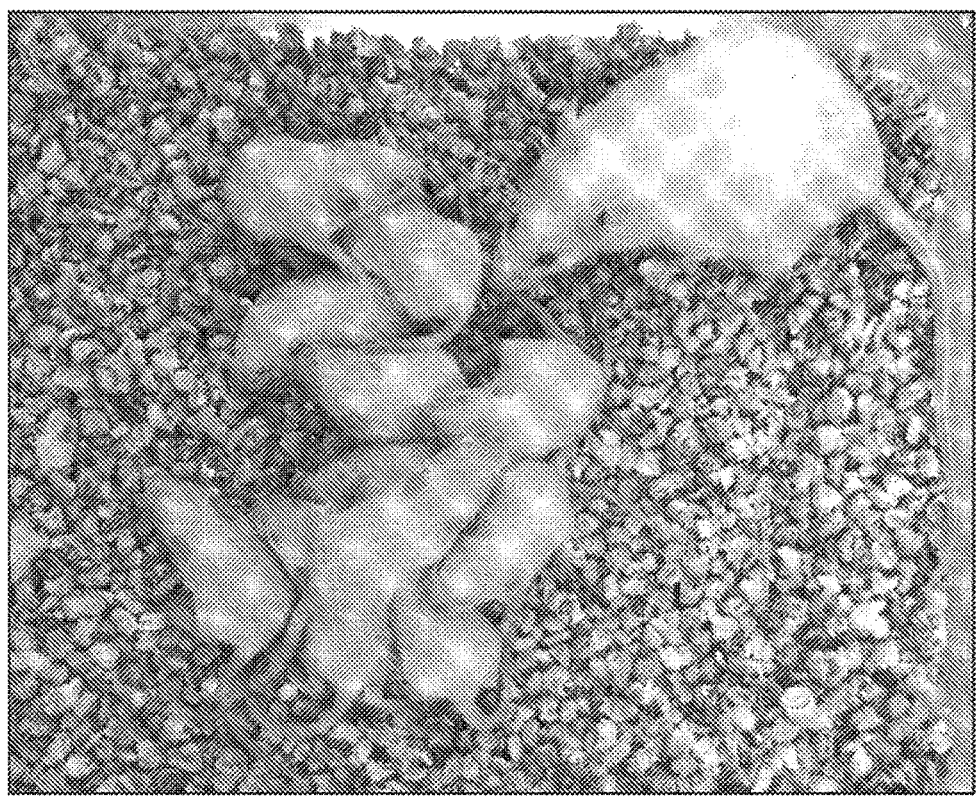

The ability to modify intact pre-implantation embryos ex vivo prompted the question of whether injection of viral particles into the oviduct of pregnant females could also result in genome editing of pre-implantation embryos. At E0.5, zygote stage embryos are located in the ampulla, a swollen region of the oviduct where fertilization occurs. The feasibility of gene editing in vivo was assessed by injecting rAAV6-Cas9 and rAAV6-sgTyr vectors into one of the oviducts of E0.5 C57BL/6NJ females mated with C57BL/6NJ males (FIGS. 3A-3B). Two albino pups out of 29 animals were generated from 5 injected females (FIG. 3C). One of albino mice fathered albino offspring after mating with an albino CD-1 female demonstrating germline transmission (FIG. 3D).

Figure 3E:
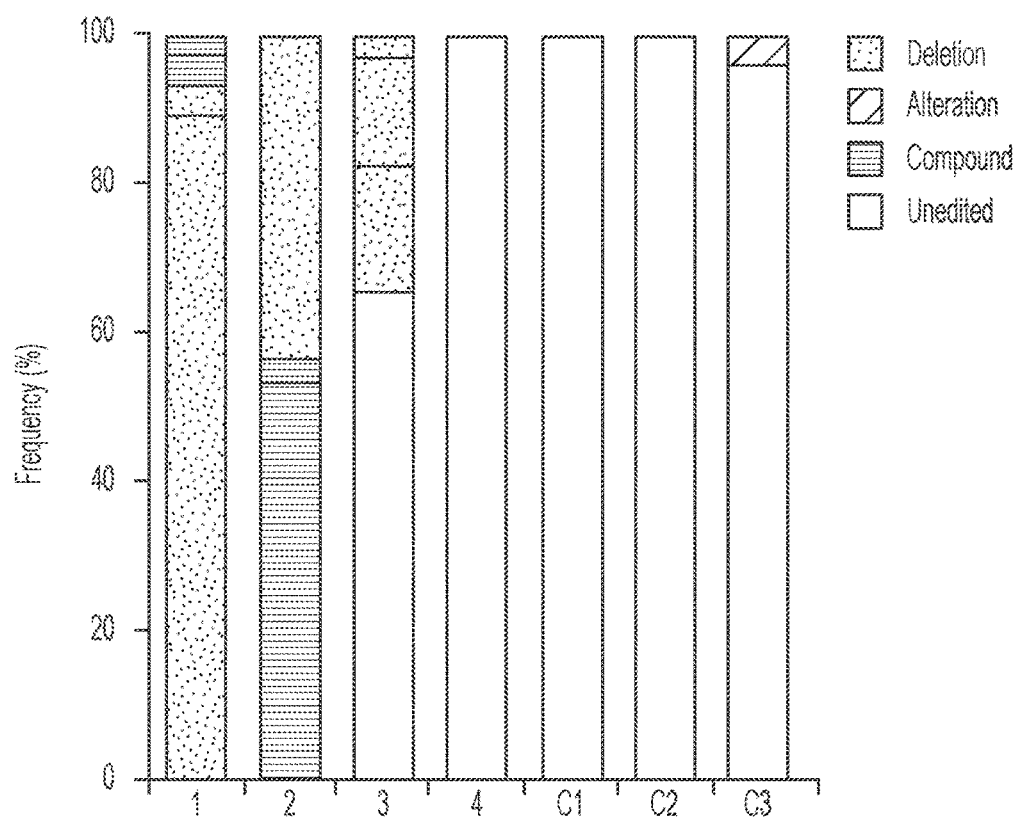

The phenotypic analysis was confirmed by SMRT sequencing and allowed detecting of deletions in one of the black littermates (FIG. 3E). Hence, 3 out of 29 mice derived from in vivo transduction with rAAV vectors showed gene editing at the Tyr locus, a frequency of 10% (FIG. 3F). Since only one oviduct was injected per female, the gene editing frequency is likely to be an underestimation.

These experiments suggest that rAAV particles can access pre-implantation embryos in the oviduct and induce genome editing in vivo.

SEQUENCES

SEQ ID NO: 1 - AAV6 capsid protein amino acid sequence
MAADGYLPDWLEDNLSEGIREWWDLKPGAPKPKANQQKQDDGRGLVLPGYKYLGPFNGLDKGEP
VNAADAAALEHDKAYDQQLKAGDNPYLRYNHADAEFQERLQEDTSFGGNLGRAVFQAKKRVLEP
FGLVEEGAKTAPGKKRPVEQSPQEPDSSSGIGKTGQQPAKKRLNFGQTGDSESVPDPQPLGEPP
ATPAAVGPTTMASGGGAPMADNNEGADGVGNASGNWHCDSTWLGDRVITTSTRTWALPTYNNHL
YKQISSASTGASNDNHYFGYSTPWGYFDFNRFHCHFSPRDWQRLINNNWGFRPKRLNFKLFNIQ
VKEVTTNDGVTTIANNLTSTVQVFSDSEYQLPYVLGSAHQGCLPPFPADVFMIPQYGYLTLNNG
SQAVGRSSFYCLEYFPSQMLRTGNNFTFSYTFEDVPFHSSYAHSQSLDRLMNPLIDQYLYYLNR
TQNQSGSAQNKDLLFSRGSPAGMSVQPKNWLPGPCYRQQRVSKTKTDNNNSNFTWTGASKYNLN
GRESIINPGTAMASHKDDKDKFFPMSGVMIFGKESAGASNTALDNVMITDEEEIKATNPVATER
FGTVAVNLQSSSTDPATGDVHVMGALPGMVWQDRDVYLQGPIWAKIPHTDGHFHPSPLMGGFGL
KHPPPQILIKNTPVPANPPAEFSATKFASFITQYSTGQVSVEIEWELQKENSKRWNPEVQYTSN
YAKSANVDFTVDNNGLYTEPRPIGTRYLTRPL SEQ ID NO: 2 - AAV6 capsid nucleic acid sequence
ATGGCTGCCGATGGTTATCTTCCAGATTGGCTCGAGGACAACCTCTCTGAGGGCATTCGCGAGT
GGTGGGACTTGAAACCTGGAGCCCGAAACCCAAAGCCAACCAGCAAAAGCAGGACGACGGCCG
GGGTCTGGTGCTTCCTGGCTACAAGTACCTCGGACCCTTCAACGGACTCGACAAGGGGGAGCCC
GTCAACGCGGCGGATGCAGCGGCCCTCGAGCACGACAAGGCCTACGACCAGCAGCTCAAAGCGG
GTGACAATCCGTACCTGCGGTATAACCACGCCGACGCCGAGTTTCAGGAGCGTCTGCAAGAAGA
TACGTCTTTTGGGGGCAACCTCGGGCGAGCAGTCTTCCAGGCCAAGAAGAGGGTTCTCGAACCT
TTTGGTCTGGTTGAGGAAGGTGCTAAGACGGCTCCTGGAAAGAAACGTCCGGTAGAGCAGTCGC
CACAAGAGCCAGACTCCTCCTCGGGCATTGGCAAGACAGGCCAGCAGCCCGCTAAAAAGAGACT
CAATTTTGGTCAGACTGGCGACTCAGAGTCAGTCCCCGACCCACAACCTCTCGGAGAACCTCCA
GCAACCCCCGCTGCTGTGGGACCTACTACAATGGCTTCAGGCGGTGGCGCACCAATGGCAGACA
ATAACGAAGGCGCCGACGGAGTGGGTAATGCCTCAGGAAATTGGCATTGCGATTCCACATGGCT
GGGCGACAGAGTCATCACCAGCACCCGAACATGGGCCTTGCCCACCTATAACAACCACCTC
TACAAGCAAATCTCCAGTGCTTCAACGGGGGCCAGCAACGACAACCACTACTTCGGCTACAGCA
CCCCCTGGGGGTATTTTGATTTCAACAGATTCCACTGCCATTTCTCACCACGTGACTGGCAGCG
ACTCATCAACAACAATTGGGGATTCCGGCCCAAGAGACTCAACTTCAAGCTCTTCAACATCCAA
GTCAAGGAGGTCACGACGAATGATGGCGTCACGACCATCGCTAATAACCTTACCAGCACGGTTC
AAGTCTTCTCGGACTCGGAGTACCAGTTGCCGTACGTCCTCGGCTCTGCGCACCAGGGCTGCCT
CCCTCCGTTCCCGGCGGACGTGTTCATGATTCCGCAGTACGGCTACCTAACGCTCAACAATGGC
AGCCAGGCAGTGGGACGGTCATCCTTTTACTGCCTGGAATATTTCCCATCGCAGATGCTGAGAA
CGGGCAATAACTTTACCTTCAGCTACACCTTCGAGGACGTGCCTTTCCACAGCAGCTACGCGCA
CAGCCAGAGCCTGGACCGGCTGATGAATCCTCTCATCGACCAGTACCTGTATTACCTGAACAGA
ACTCAGAATCAGTCCGGAAGTGCCCAAAACAAGGACTTGCTGTTTAGCCGGGGGTCTCCAGCTG
GCATGTCTGTTCAGCCCAAAAACTGGCTACCTGGACCCTGTTACCGGCAGCAGCGCGTTTCTAA
AACAAAAACAGACAACAACAACAGCAACTTTACCTGGACTGGTGCTTCAAAATATAACCTTAAT
GGGCGTGAATCTATAATCAACCCTGGCACTGCTATGGCCTCACACAAAGACGACAAAGACAAGT
TCTTTCCCATGAGCGGTGTCATGATTTTTGGAAAGGAGAGCGCCGGAGCTTCAAACACTGCATT
GGACAATGTCATGATCACAGACGAAGAGGAAATCAAAGCCACTAACCCCGTGGCCACCGAAAGA
TTTGGGACTGTGGCAGTCAATCTCCAGAGCAGCAGCACGAAGACCCTGCGACCGGAGATGTGCATG
TTATGGGAGCCTTACCTGGAATGGTGTGGCAAGACAGAGACGTATACCTGCAGGGTCCTATTTG
GGCCAAAATTCCTCACACGGATGGACACTTTCACCCGTCTCCTCTCATGGGCGGCTTTGGACTT
AAGCACCCGCCTCCTCAGATCCTCATCAAAAACACGCCTGTTCCTGCGAATCCTCCGGCAGAGT
TTTCGGCTACAAAGTTTGCTTCATTCATCACCCAGTATTCCACAGGACAAGTGAGCGTGGAGAT
TGAATGGGAGCTGCAGAAAGAAAACAGCAAACGCTGGAATCCCGAAGTGCAGTATACATCTAAC
TATGCAAAATCTGCCAACGTTGATTTCACTGTGGACAACAATGGACTTTATACTGAGCCTCGCC
CCATTGGCACCCGTTACCTCACCCGTCCCCTG SEQ ID NO: 3 - rAAV.CB6-EGFP
CTGCGCGCTCGCTCGCTCACTGAGGCGCGCCCGGGCAAAGCCCGGGCGTCGGGCGACCTTTGGTC
GCCCGGCCTCAGTGAGCGAGCGAGCGCGCAGAGAGGGAGTGTAGCCATGCTCTAGGAAGATCAA
TTCGGTACAATTCACGCGTCGACATTGATTATTGACTAGTTATTAATAGTAATCAATTACGGGG
TCATTAGTTCATAGCCCATATATGGAGTTCCGCGTTACATAACTTACGGTAAATGGCCCGCCTG
GCTGACCGCCCAACGACCCCCGCCCATTGACGTCAATAATGACGTATGTTCCCATAGTAACGCC
AATAGGGACTTTCCATTGACGTCAATGGGTGGAGTATTTACGGTAAACTGCCCACTTGGCAGTA
CATCAAGTGTATCATATGCCAAGTACGCCCCCTATTGACGTCAATGACGGTAAATGGCCCGCCT
GGCATTATGCCCAGTACATGACCTTATGGGACTTTCCTACTTGGCAGTACATCTACGTATTAGT
CATCGCTATTACCATGTCGAGGCCACGTTCTGCTTCACTCTCCCCATCTCCCCCCCCTCCCCAC
CCCCAATTTTGTATTTATTTATTTTTTAATTATTTTGTGCAGCGATGGGGGCGGGGGGGGGGG
CGCGCGCCAGGCGGGGCGGGGCGGGGCGAGGGGCGGGGCGGGGCGAGGCGGAGAGGTGCGGCGG

| SEQUENCES |
|---|
| CAGCCAATCAGAGCGGCGCGCTCCGAAAGTTTCCTTTTATGGCGAGGCGGCGGCGGCGGCC
CTATAAAAAGCGAAGCGCGCGGCGGGCGGGAGCAAGCTCTAGCCTCGAGAATTACTTAATACGA
CTCACTATAGGCTAGTAATACGACTCACTATAGATGGTGAGCAAGGGCGAGGAGCTGTTCACCG
GGGTGGTGCCCATCCTGGTCGAGCTGGACGGCGACGTAAACGGCCACAAGTTCAGCGTGTCCGG
CGAGGGCGAGGGCGATGCCACCTACGGCAAGCTGACCCTGAAGTTCATCTGCACCACCGGCAAG
CTGCCCGTGCCCTGGCCCACCCTCGTGACCACCCTGACCTACGGCGTGCAGTGCTTCAGCCGCT
ACCCCGACCACATGAAGCAGCACGACTTCTTCAAGTCCGCCATGCCCGAAGGCTACGTCCAGGA
GCGCACCATCTTCTTCAAGGACGACGGCAACTACAAGACCCGCGCCGAGGTGAAGTTCGAGGGC
GACACCCTGGTGAACCGCATCGAGCTGAAGGGCATCGACTTCAAGGAGGACGGCAACATCCTGG
GGCACAAGCTGGAGTACAACTACAACAGCCACAACGTCTATATCATGGCCGACAAGCAGAAGAA
CGGCATCAAGGTGAACTTCAAGATCCGCCACAACATCGAGGACGGCAGCGTGCAGCTCGCCGAC
CACTACCAGCAGAACACCCCCATCGGCGACGGCCCCGTGCTGCTGCCCGACAACCACTACCTGA
GCACCCAGTCCGCCCTGAGCAAAGACCCCAACGAGAAGCGCGATCACATGGTCCTGCTGGAGTT
CGTGACCGCCGCCGGGATCACTCTCGGCATGGACGAGCTGTACAAGTAAAGCGGCCCTAGCGTT
TAAACGGGCCCTCTAGAGTCGACCCGGGCGGCCTCGAGGACGGGGTGAACTACGCCTGAGGATC
CGATCTTTTTCCCTCTGCCAAAAATTATGGGGACATCATGAAGCCCCTTGAGCATCTGACTTCT
GGCTAATAAAGGAAATTTATTTTCATTGCAATAGTGTGTTGGAATTTTTTGTGTCTCTCACTCG
GCCTAGGTAGATAAGTAGCATGGCGGGTTAATCATTAACTACAAGGAACCCCTAGTGATGGAGT
TGGCCACTCCCTCTCTGCGCGCTCGCTCGCTCACTGAGGCCGGGCGACCAAAGGTCGCCCGACG
CCCGGGCTTTGCCCGGGCGGCCTCAGTGAGCGAGCGAGCGCGCAG |

SEQ ID NO: 4 - EGFP in rAAV.CB6-EGFP
MVSKGEELFTGVVPILVELDGDVNGHKFSVSGEGEGDATYGKLTLKFICTTGKLPVPWPTLVTT
LTYGVQCFSRYPDHMKQHDFFKSAMPEGYVQERTIFFKDDGNYKTRAEVKFEGDTLVNRIELKG
IDFKEDGNILGHKLEYNYNSHNVYIMADKQKNGIKVNFKIRHNIEDGSVQLADHYQQNTPIGDG
PVLLPDNHYLSTQSALSKDPNEKRDHMVLLEFVTAAGITLGMDELYK

SEQ ID NO: 5 - rAAV6.CB6-Cre
CTGCGCGCTCGCTCGCTCACTGAGGCCGCCCGGGCAAAGCCCGGGCGTCGGGCGACCTTTGGTC
GCCCGGCCTCAGTGAGCGAGCGAGCGCGCAGAGAGGGAGTGGCCAACTCCATCACTAGGGGTTC
CTTGTAGTTAATGATTAACCCGCCATGCTACTTATCTACCAGGGTAATGGGGATCCTCTAGAAC
TATAGCTAGTCGACATTGATTATTGACTAGTTATTAATAGTAATCAATTACGGGGTCATTAGTT
CATAGCCCATATATGGAGTTCCGCGTTACATAACTTACGGTAAATGGCCCGCCTGGCTGACCGC
CCAACGACCCCCGCCCATTGACGTCAATAATGACGTATGTTCCCATAGTAACGCCAATAGGGAC
TTTCCATTGACGTCAATGGGTGGAGTATTTACGGTAAACTGCCCACTTGGCAGTACATCAAGTG
TATCATATGCCAAGTACGCCCCCTATTGACGTCAATGACGGTAAATGGCCCGCCTGGCATTATG
CCCAGTACATGACCTTATGGGACTTTCCTACTTGGCAGTACATCTACGTATTAGTCATCGCTAT
TACCATGTCGAGGCCACGTTCTGCTTCACTCTCCCCATCTCCCCCCCTCCCCACCCCCAATTT
TGTATTTATTTATTTTTTAATTATTTTGTGCAGCGATGGGGGCGGGGGGGGGGCGCGCGCCA
GGCGGGGCGGGGCGGGGCGAGGGGCGGGGCGGGGCGAGGCGGAGAGGTGCGGCGGCAGCCAATC
AGAGCGGCGCGCTCCGAAAGTTTCCTTTTATGGCGAGGCGGCGGCGGCGGCCCCTATAAAAA
GCGAAGCGCGCGGCGGGCGGGAGCAAGCTTTATTGCGGTAGTTTATCACAGTTAAATTGCTAAC
GCAGTCAGTGCTTCTGACACAACAGTCTCGAACTTAAGCTGCAGAAGTTGGTCGTGAGGCACTG
GGCAGGTAAGTATCAAGGTTACAAGACAGGTTTAAGGAGACCAATAGAAACTGGGCTTGTCGAG
ACAGAGAAGACTCTTGCGTTTCTGATAGGCACCTATTGGTCTTACTGACATCCACTTTGCCTTT
CTCTCCACAGGTGTCCACTCCCAGTTCAATTACAGCTCTTAAGGCTAGAGTACTTAATACGACT
CACTATAGGCTAGCCTGAGAATTGTACACTTTACTTAAAACCATTATCTGAGTGTGAAATGTC
CAATTTACTGACCGTACACCAAAATTTGCCTGCATTACCGGTCGATGCAACGAGTGATGAGGTT
CGCAAGAACCTGATGGACATGTTCAGGGATCGCCAGGCGGTTTTCTGAGCATACCTGGAAAATGC
TTCTGTCCGTTTGCCGGTCGTGGGCGGCATGGTGCAAGTTGAATAACCGGAAATGGTTTCCCGC
AGAACCTGAAGATGTTCGCGATTATCTTCTATATCTTCAGGCGCGCGGTCTGGCAGTAAAAACT
ATCCAGCAACATTTGGGCCAGCTAAACATGCTTCATCGTCGGTCCGGGCTGCCACGACCAAGTG
ACAGCAATGCTGTTTCACTGGTTATGCGGCGGATCCGAAAAGAAAACGTTGATGCCGGTGAACG
TGCAAAACAGGCTCTAGCGTTCGAACGCACTGATTTCGACCAGGTTCGTTCACTCATGGAAAAT
AGCGATCGCTGCCAGGATATACGTAATCTGGCATTTCTGGGGATTGCTTATAACACCCTGTTAC
GTATAGCCGAAATTGCCAGGATCAGGGTTAAAGATATCTCACGTACTGACGGTGGGAGAATGTT
AATCCATATTGGCAGAACGAAAACGCTGGTTAGCACCGCAGGTGTAGAGAAGGCACTTAGCCTG
GGGGTAACTAAACTGGTCGAGCGATGGATTTCCGTCTCTGGTGTAGCTGATGATCCGAATAACT
ACCTGTTTTGCCGGGTCAGAAAAAATGGTGTTGCCGCGCCATCTGCCACCAGCCAGCTATCAAC
TCGCGCCCTGGAAGGGATTTTTGAAGCAACTCATCGATTGATTTACGGCGCTAAGGATGACTCT
GGTCAGAGATACCTGGCCTGGTCTGGACACAGTGCCCGTGTCGGAGCCGCGCGAGATATGGCCC
GCGCTGGAGTTTCAATACCGGAGATCATGCAAGCTGGTGGCTGGACCAATGTAAATATTGTCAT
GAACTATATCCGTAACCTGGATAGTGAAACAGGGGCAATGGTGCGCCTGCTGGAAGATGGCGAT
TAGCCATTAACGCGGCGTGGTACCTCTAGAGTCGAGGACGGGGTGAACTACGCCTGAGGATCCG
ATCTTTTTCCCTCTGCCAAAAATTATGGGGACATCATGAAGCCCCTTGAGCATCTGACTTCTGG
CTAATAAAGGAAATTTATTTTCATTGCAATAGTGTGTTGGAATTTTTTGTGTCTCTCACTCGGA
AGCAATTCGTTGATCTGAATTTCGACCACCCATAATACCCATTACCCTGGTAGATAAGTAGCAT
GGCGGGTTAATCATTAACTACAAGGAACCCCTAGTGATGGAGTTGGCCACTCCCTCTCTGCGCG
CTCGCTCGCTCACTGAGGCCGGGCGACCAAAGGTCGCCCGACGCCCGGGCTTTGCCCGGGCGGC
CTCAGTGAGCGAGCGAGCGCGCAG

SEQ ID NO: 6 - Cre in rAAV6.CB6-Cre
MSNLLTVHQNLPALPVDATSDEVRKNLMDMFRDRQAFSEHTWKMLLSVCRSWAAWCKLNNRKWF
PAEPEDVRDYLYLQARGLAVKTIQQHLGQLNMLHRRSGLPRPSDSNAVSLVMRRIRKENVDAG
ERAKQALAFERTDFDQVRSLMENSDRCQDIRNLAFLGIAYNTLLRIAEIARIRVKDISRTDGGR

| SEQUENCES |
| --- |
| MLIHIGRTKTLVSTAGVEKALSLGVTKLVERWISVSGVADDPNNYLFCRVRKNGVAAPSATSQL STRALEGIFEATHRLIYGAKDDSGQRYLAWSGHSARVGAARDMARAGVSIPEIMQAGGWTNVNI VMNYIRNLDSETGAMVRLLEDGD |
| SEQ ID NO: 7 - rAAV6.U1a-SpCas9 CCTGCAGGCAGCTGCGCGCTCGCTCGCTCACTGAGGCCGCCCGGGCAAAGCCCGGGCGTCGGGC GACCTTTGGTCGCCCGGCCTCAGTGAGCGAGCGAGCGCGCAGAGAGGGAGTGGCCAACTCCATC ACTAGGGGTTCCTGCGGCCTCTAGAATGGAGGCGGTACTATGTAGATGAGAATTCAGGAGCAAA CTGGGAAAAGCAACTGCTTCCAAATATTTGTGATTTTTACAGTGTAGTTTTGGAAAAACTCTTA GCCTACCAATTCTTCTAAGTGTTTTAAAATGTGGGAGCCAGTACACATGAAGTTATAGAGTGTT TTAATGAGGCTTAAATATTTACCGTAACTATGAAATGCTACGCATATCATGCTGTTCAGGCTCC GTGGCCACGCAACTCATACTACCGGTGCCACCATGTACCCATACGATGTTCCAGATTACGCTTC GCCGAAGAAAAGCGCAAGGTCGAAGCGTCCGACAAGAAGTACAGCATCGGCCTGGACATCGGC ACCAACTCTGTGGGCTGGGCCGTGATCACCGACGAGTACAAGGTGCCCAGCAAGAAATTCAAGG TGCTGGGCAACACCGACCGGCACAGCATCAAGAAGAACCTGATCGGAGCCCTGCTGTTCGACAG CGGCGAAACAGCCGAGGCCACCCGGCTGAAGAGAACCGCCAGAAGAAGATACACCAGACGGAAG AACCGGATCTGCTATCTGCAAGAGATCTTCAGCAACGAGATGGCCAAGGTGGACGACAGCTTCT TCCACAGACTGGAAGAGTCCTTCCTGGTGGAAGAGGATAAGAAGCACGAGCGGCACCCCATCTT CGGCAACATCGTGGACGAGGTGGCCTACCACGAGAAGTACCCCACCATCTACCACCTGAGAAAG AAACTGGTGGACAGCACCGACAAGGCCGACCTGCGGCTGATCTATCTGGCCCTGGCCCACATGA TCAAGTTCCGGGGCCACTTCCTGATCGAGGGCGACCTGAACCCCGACAACAGCGACGTGGACAA GCTGTTCATCCAGCTGGTGCAGACCTACAACCAGCTGTTCGAGGAAAACCCCATCAACGCCAGC GGCGTGGACGCCAAGGCCATCCTGTCTGCCAGACTGAGCAAGAGCAGACGGCTGGAAAATCTGA TCGCCCAGCTGCCCGGCGAGAAGAAGAATGGCCTGTTCGGCAACCTGATTGCCCTGAGCCTGGG CCTGACCCCCAACTTCAAGAGCAACTTCGACCTGGCCGAGGATGCCAAACTGCAGCTGAGCAAG GACACCTACGACGACGACCTGGACAACCTGCTGGCCCAGATCGGCGACCAGTACGCCGACCTGT TTCTGGCCGCCAAGAACCTGTCCGACGCCATCCTGCTGAGCGACATCCTGAGAGTGAACACCGA GATCACCAAGGCCCCCCTGAGCGCCTCTATGATCAAGAGATACGACGAGCACCACCAGGACCTG ACCCTGCTGAAAGCTCTCGTGCGGCAGCAGCTGCCTGAGAAGTACAAAGAGATTTTCTTCGACC AGAGCAAGAACGGCTACGCCGGCTACATTGACGGCGGAGCCAGCCAGGAAGAGTTCTACAAGTT CATCAAGCCCATCCTGGAAAAGATGGACGGCACCGAGGAACTGCTCGTGAAGCTGAACAGAGAG GACCTGCTGCGCAAGCAGCGGACCTTCGACAACGGCAGCATCCCCCACCAGATCCACCTGGGAG AGCTGCACGCCATTCTGCGGCGGCAGGAAGATTTTTACCCATTCCTGAAGGACAACCGGGAAAA GATCGAGAAGATCCTGACCTTCCGCATCCCCTACTACGTGGGCCCTCTGGCCAGGGGAAACAGC AGATTCGCCTGGATGACCAGAAAGAGCGAGGAAACCATCACCCCCTGGAACTTCGAGGAAGTGG TGGACAAGGGCGCTTCCGCCCAGAGCTTCATCGAGCGGATGACCAACTTCGATAAGAACCTGCC CAACGAGAAGGTGCTGCCCAAGCACAGCCTGCTGTACGAGTACTTCACCGTGTATAACGAGCTG ACCAAAGTGAAATACGTGACCGAGGGAATGAGAAAGCCCGCCTTCCTGAGCGGCGAGCAGAAAA AGGCCATCGTGGACCTGCTGTTCAAGACCAACCGGAAAGTGACCGTGAAGCAGCTGAAAGAGGA CTACTTCAAGAAAATCGAGTGCTTCGACTCCGTGGAAATCTCCGGCGTGGAAGATCGGTTCAAC GCCTCCCTGGGCACATACCACGATCTGCTGAAAATTATCAAGGACAAGGACTTCCTGGACAATG AGGAAAACGAGGACATTCTGGAAGATATCGTGCTGACCCTGACACTGTTTGAGGACAGAGAGAT GATCGAGGAACGGCTGAAAACCTATGCCCACCTGTTCGACGACAAAGTGATGAAGCAGCTGAAG CGGCGGAGATACACCGGCTGGGGCAGGCTGAGCCGGAAGCTGATCAACGGCATCCGGGACAAGC AGTCCGGCAAGACAATCCTGGATTTCCTGAAGTCCGACGGCTTCGCCAACAGAAACTTCATGCA GCTGATCCACGACGACAGCCTGACCTTTAAAGAGGACATCCAGAAAGCCCAGGTGTCCGGCCAG GGCGATAGCCTGCACGAGCACATTGCCAATCTGGCCGGCAGCCCCGCCATTAAGAAGGGCATCC TGCAGACAGTGAAGGTGGTGGACGAGCTCGTGAAAGTGATGGGCCGGCACAAGCCCGAGAACAT CGTGATCGAAATGGCCAGAGAGAACCAGACCACCCAGAAGGGACAGAAGAACAGCCGCGAGAGA ATGAAGCGGATCGAAGAGGGCATCAAAGAGCTGGGCAGCCAGATCCTGAAAGAACACCCCGTGG AAAACACCCAGCTGCAGAACGAGAAGCTGTACCTGTACTACCTGCAGAATGGGCGGGATATGTA CGTGGACCAGGAACTGGACATCAACCGGCTGTCCGACTACGATGTGGACCATATCGTGCCTCAG AGCTTTCTGAAGGACGACTCCATCGACAACAAGGTGCTGACCAGAAGCGACAAGAACCGGGGCA AGAGCGACAACGTGCCCTCCGAAGAGGTCGTGAAGAAGATGAAGAACTACTGGCGGCAGCTGCT GAACGCCAAGCTGATTACCCAGAGAAAGTTCGACAATCTGACCAAGGCCGAGAGAGGCGGCCTG AGCGAACTGGATAAGGCCGGCTTCATCAAGAGACAGCTGGTGGAAACCCGGCAGATCACAAAGC ACGTGGCACAGATCCTGGACTCCCGGATGAACACTAAGTACGACGAGAATGACAAGCTGATCCG GGAAGTGAAAGTGATCACCCTGAAGTCCAAGCTGGTGTCCGATTTCCGGAAGGATTTCCAGTTT TACAAAGTGCGCGAGATCAACAACTACCACCACGCCCACGACGCCTACCTGAACGCCGTCGTGG GAACCGCCCTGATCAAAAAGTACCCTAAGCTGGAAAGCGAGTTCGTGTACGGCGACTACAAGGT GTACGACGTGCGGAAGATGATCGCCAAGAGCGAGCAGGAAATCGGCAAGGCTACCGCCAAGTAC TTCTTCTACAGCAACATCATGAACTTTTTCAAGACCGAGATTACCCTGGCCAACGGCGAGATCC GGAAGCGGCCTCTGATCGAGACAAACGGCGAAACCGGGGAGATCGTGTGGGATAAGGGCCGGGA TTTTGCCACCGTGCGGAAAGTGCTGAGCATGCCCCAAGTGAATATCGTGAAAAAGACCGAGGTG CAGACAGGCGGCTTCAGCAAAGAGTCTATCCTGCCCAAGAGGAACAGCGATAAGCTGATCGCCA GAAAGAAGGACTGGGACCCTAAGAAGTACGGCGGCTTCGACAGCCCCACCGTGGCCTATTCTGT GCTGGTGGTGGCCAAAGTGGAAAAGGGCAAGTCCAAGAAACTGAAGAGTGTGAAAGAGCTGCTG GGGATCACCATCATGGAAAGAAGCAGCTTCGAGAAGAATCCCATCGACTTTCTGGAAGCCAAGG GCTACAAAGAAGTGAAAAAGGACCTGATCATCAAGCTGCCTAAGTACTCCCTGTTCGAGCTGGA AAACGGCCGAAAGAGAATGCTGGCCTCTGCCGGCGAACTGCAGAAGGGAAACGAACTGGCCCTG CCCTCCAAATATGTGAACTTCCTGTACCTGGCCAGCCACTATGAGAAGCTGAAGGGCTCCCCCG AGGATAATGAGCAGAAACAGCTGTTTGTGGAACAGCACAAGCACTACCTGGACGAGATCATCGA GCAGATCAGCGAGTTCTCCAAGAGAGTGATCCTGGCCGACGCTAATCTGGACAAAGTGCTGTCC GCCTACAACAAGCACCGGGATAAGCCCATCAGAGAGCAGGCCGAGAATATCATCCACCTGTTTA CCCTGACCAATCTGGGAGCCCCTGCCGCCTTCAAGTACTTTGACACCACCATCGACCGGAAGAG GTACACCAGCACCAAAGAGGTGCTGGACGCCACCCTGATCCACCAGAGCATCACCGGCCTGTAC GAGACACGGATCGACCTGTCTCAGCTGGGAGGCGACAGCCCCAAGAAGAAGAGAAAGGTGGAGG |

| SEQUENCES |
|---|
| CCAGCTAAGAATTCGATCTTTTTCCCTCTGCCAAAAATTATGGGGACATCATGAAGCCCCTTGA<br>GCATCTGACTTCTGGCTAATAAAGGAAATTTATTTTCATTGCAATAGTGTGTTGGAATTTTTTG<br>TGTCTCTCACTCGGCGGCCGCAGGAACCCCTAGTGATGGAGTTGGCCACTCCCTCTCTGCGCGC<br>TCGCTCGCTCACTGAGGCCGGGCGACCAAAGGTCGCCCGACGCCCGGGCTTTGCCCGGGCGGCC<br>TCAGTGAGCGAGCGAGCGCGCAGCTGCCTGCAGG<br><br>SEQ ID NO: 8 - SpCas9 in rAAV6.U1a-SpCas9<br>MYPYDVPDYASPKKKRKVEASDKKYSIGLDIGTNSVGWAVITDEYKVPSKKFKVLGNTDRHSIK<br>KNLIGALLFDSGETAEATRLKRTARRRYTRRKNRICYLQEIFSNEMAKVDDSFFHRLEESFLVE<br>EDKKHERHPIFGNIVDEVAYHEKYPTIYHLRKKLVDSTDKADLRLIYLALAHMIKFRGHFLIEG<br>DLNPDNSDVDKLFIQLVQTYNQLFEENPINASGVDAKAILSARLSKSRRLENLIAQLPGEKKNG<br>LFGNLIALSLGLTPNFKSNFDLAEDAKLQLSKDTYDDDLDNLLAQIGDQYADLFLAAKNLSDAI<br>LLSDILRVNTEITKAPLSASMIKRYDEHHQDLTLLKALVRQQLPEKYKEIFFDQSKNGYAGYID<br>GGASQEEFYKFIKPILEKMDGTEELLVKLNREDLLRKQRTFDNGSIPHQIHLGELHAILRRQED<br>FYPFLKDNREKIEKILTFRIPYYVGPLARGNSRFAWMTRKSEETITPWNFEEVVDKGASAQSFI<br>ERMTNFDKNLPNEKVLPKHSLLYEYFTVYNELTKVKYVTEGMRKPAFLSGEQKKAIVDLLFKTN<br>RKVTVKQLKEDYFKKIECFDSVEISGVEDRFNASLGTYHDLLKIIKDKDFLDNEENEDILEDIV<br>LTLTLFEDREMIEERLKTYAHLFDDKVMKQLKRRRYTGWGRLSRKLINGIRDKQSGKTILDFLK<br>SDGFANRNFMQLIHDDSLTFKEDIQKAQVSGQGDSLHEHIANLAGSPAIKKGILQTVKVVDELV<br>KVMGRHKPENIVIEMARENQTTQKGQKNSRERMKRIEEGIKELGSQILKEHPVENTQLQNEKLY<br>LYYLQNGRDMYVDQELDINRLSDYDVDHIVPQSFLKDDSIDNKVLTRSDKNRGKSDNVPSEEVV<br>KKMKNYWRQLLNAKLITQRKFDNLTKAERGGLSELDKAGFIKRQLVETRQITKHVAQILDSRMN<br>TKYDENDKLIREVKVITLKSKLVSDFRKDFQFYKVREINNYHHAHDAYLNAVVGTALIKKYPKL<br>ESEFVYGDYKVYDVRKMIAKSEQEIGKATAKYFFYSNIMNFFKTEITLANGEIRKRPLIETNGE<br>TGEIVWDKGRDFATVRKVLSMPQVNIVKKTEVQTGGFSKESILPKRNSDKLIARKKDWDPKKYG<br>GFDSPTVAYSVLVVAKVEKGKSKKLKSVKELLGITIMERSSFEKNPIDFLEAKGYKEVKKDLII<br>KLPKYSLFELENGRKRMLASAGELQKGNELALPSKYVNFLYLASHYEKLKGSPEDNEQKQLFVE<br>QHKHYLDEIIEQISEFSKRVILADANLDKVLSAYNKHRDKPIREQAENIIHLFTLTNLGAPAAF<br>KYFDTTIDRKRYTSTKEVLDATLIHQSITGLYETRIDLSQLGGDSPKKKRKVEAS<br><br>SEQ ID NO: 9 - rAAV6.U6-sgTyr.CB6-EGFP<br>CTGCGCGCTCGCTCGCTCACTGAGGCCGCCCGGGCAAAGCCCGGGCGTCGGGCGACCTTTGGTC<br>GCCCGGCCTCAGTGAGCGAGCGAGCGCGCAGAGAGGGAGTGTAGCCATGCTCTAGGAAGATCAA<br>TTCGGTACAATTCACGCGTGAGGGCCTATTTCCCATGATTCCTTCATATTTGCATATACGATAC<br>AAGGCTGTTAGAGAGATAATTGGAATTAATTTGACTGTAAACACAAAGATATTAGTACAAAATA<br>CGTGACGTAGAAAGTAATAATTTCTTGGGTAGTTTGCAGTTTTAAAATTATGTTTTAAAATGGA<br>CTATCATATGCTTACCGTAACTTGAAAGTATTTCGATTTCTTGGCTTTATATATCTTGTGGAAA<br>GGACGAAACACCGAACTTCATGGGTTTCAACTGGTTTTAGAGCTAGAAATAGCAAGTTAAAATA<br>AGGCTAGTCCGTTATCAACTTGAAAAAGTGGCACCGAGTCGGTGCTTTTTTACGCGTCGACATT<br>GATTATTGACTAGTTATTAATAGTAATCAATTACGGGGTCATTAGTTCATAGCCCATATATGGA<br>GTTCCGCGTTACATAACTTACGGTAAATGGCCCGCCTGGCTGACCGCCCAACGACCCCCGCCCA<br>TTGACGTCAATAATGACGTATGTTCCCATAGTAACGCCAATAGGGACTTTCCATTGACGTCAAT<br>GGGTAGTATTTACGGTAAACTGCCCACTTGGCAGTACATCAAGTGTATCATATGCCAAGTAC<br>GCCCCCTATTGACGTCAATGACGGTAAATGGCCCGCCTGGCATTATGCCCAGTACATGACCTTA<br>TGGGACTTTCCTACTTGGCAGTACATCTACGTATTAGTCATCGCTATTACCATGTCGAGGCCAC<br>GTTCTGCTTCACTCTCCCCATCTCCCCCCCCTCCCCACCCCCAATTTTGTATTTATTTATTTTT<br>TAATTATTTTGTGCAGCGATGGGGGCGGGGGGGGGGCGCGCGCCAGGCGGGGCGGGGCGGGG<br>CGAGGGGCGGGGCGGGGCGAGGCGGAGAGGTGCGGCGGCAGCCAATCAGAGCGGCGCGCTCCGA<br>AAGTTTCCTTTTATGGCGAGGCGGCGGCGGCGGCGGCCCTATAAAAAGCGAAGCGCGCGGCGGG<br>CGGGAGCAAGCTCTAGCCTCGAGAATTACTTAATACGACTCACTATAGGCTAGTAATACGACTC<br>ACTATAGATGGTGAGCAAGGGCGAGGAGCTGTTCACCGGGGTGGTGCCCATCCTGGTCGAGCTG<br>GACGGCGACGTAAACGGCCACAAGTTCAGCGTGTCCGGCGAGGGCGAGGGCGATGCCACCTACG<br>GCAAGCTGACCCTGAAGTTCATCTGCACCACCGGCAAGCTGCCCGTGCCCTGGCCCACCCTCGT<br>GACCACCCTGACCTACGGCGTGCAGTGCTTCAGCCGCTACCCCGACCACATGAAGCAGCACGAC<br>TTCTTCAAGTCCGCCATGCCCGAAGGCTACGTCCAGGAGCGCACCATCTTCTTCAAGGACGACG<br>GCAACTACAAGACCCGCGCCGAGGTGAAGTTCGAGGGCGACACCCTGGTGAACCGCATCGAGCT<br>GAAGGGCATCGACTTCAAGGAGGACGGCAACATCCTGGGGCACAAGCTGGAGTACAACTACAAC<br>AGCCACAACGTCTATATCATGGCCGACAAGCAGAAGAACGGCATCAAGGTGAACTTCAAGATCC<br>GCCACAACATCGAGGACGGCAGCGTGCAGCTCGCCGACCACTACCAGCAGAACACCCCCATCGG<br>CGACGGCCCCGTGCTGCTGCCCGACAACCACTACCTGAGCACCCAGTCCGCCCTGAGCAAAGAC<br>CCCAACGAGAAGCGCGATCACATGGTCCTGCTGGAGTTCGTGACCGCCGCCGGGATCACTCTCG<br>GCATGGACGAGCTGTACAAGTAAAGCGGCCCTAGCGTTTAAACGGGCCCTCTAGAGTCGACCCG<br>GGCGGCCTCGAGGACGGGGTGAACTACGCCTGAGGATCCGATCTTTTTCCCTCTGCCAAAAATT<br>ATGGGGACATCATGAAGCCCCTTGAGCATCTGACTTCTGGCTAATAAAGGAAATTTATTTTCAT<br>TGCAATAGTGTGTTGGAATTTTTTGTGTCTCTCACTCGGCCTAGGTAGATAAGTAGCATGGCGG<br>GTTAATCATTAACTACAAGGAACCCCTAGTGATGGAGTTGGCCACTCCCTCTCTGCGCGCTCGC<br>TCGCTCACTGAGGCCGGGCGACCAAAGGTCGCCCGACGCCCGGGCTTTGCCCGGGCGGCCTCAG<br>TGAGCGAGCGAGCGCGCAG<br><br>SEQ ID NO: 10 - EGFP in rAAV6.U6-sgTyr.Cb6-EGFP<br>MVSKGEELFTGVVPILVELDGDVNGHKFSVSGEGEGDATYGKLTLKFICTTGKLPVPWPTLVTT<br>LTYGVQCFSRYPDHMKQHDFFKSAMPEGYVQERTIFFKDDGNYKTRAEVKFEGDTLVNRIELKG<br>IDFKEDGNILGHKLEYNYNSHNVYIMADKQKNGIKVNFKIRHNIEDGSVQLADHYQQNTPIGDG<br>PVLLPDNHYLSTQSALSKDPNEKRDHMVLLEFVTAAGITLGMDELYK |

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present disclosure, and without departing from the spirit and scope thereof, can make various changes and modifications of the present disclosure to adapt it to various usages and conditions. Thus, other embodiments are also within the claims.

EQUIVALENTS AND SCOPE

Those skilled in the art will recognize, or be able to ascertain using no more than routine experimentation, many equivalents to the specific embodiments of the present disclosure described herein. The scope of the present disclosure is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

Furthermore, the present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A method for delivering a gene editing molecule to cells of a pre-implantation embryo comprising an intact zona pellucida, the method comprising transducing the pre-implantation embryo in an oviduct of a subject with a recombinant adeno-associated virus (rAAV) having a capsid harboring a nucleic acid comprising a promoter operably linked to a transgene encoding a gene editing molecule, wherein the transducing does not comprise injection of the rAAVs into the pre-implantation embryo, and wherein the transducing comprises direct injection of the rAAV into the oviduct of the subject.

2. The method of claim 1, wherein the pre-implantation embryo is a mammalian pre-implantation embryo.

3. The method of claim 1, wherein the capsid comprises a capsid protein of a serotype selected from: AAV1, AAV2, AAV3b, AAV4, AAV5, AAV6, AAV6.2, AAV7, AAV8, AAV9, AAVrh.39, AAVrh.43, AAVrh.8, and AAVrh.10.

4. The method of claim 1, wherein the gene editing molecule is a nuclease or a recombinase.

5. The method of claim 1, wherein the gene editing molecule comprises an engineered guide RNA.

6. A method for facilitating genome editing in cells of a pre-implantation embryo comprising an intact zona pellucida, the method comprising transducing the pre-implantation embryo in an oviduct of a subject with:
- a first rAAV comprising a capsid harboring a nucleic acid comprising a promoter operably linked to a transgene encoding a guide RNA; and
- a second rAAV comprising a capsid harboring a nucleic acid comprising a promoter operably linked to a transgene encoding a CRISPR/Cas-associated protein, wherein the transducing does not comprise injection of the first rAAV and second rAAVs into the pre-implantation embryo, and wherein the transducing comprises direct injection of the first and second rAAVs into the oviduct of the subject.

7. The method of claim 6, wherein the CRISPR/Cas-associated protein is a Cas9 enzyme or variant thereof.

8. The method of claim 1, wherein the method comprises administering to the subject at least $6 \times 10^9$ gene copies (GCs) of the rAAV.

9. The method of claim 1, wherein the pre-implantation embryo is at a morula or pre-implantation blastocyst stage.

10. The method of claim 1, wherein the pre-implantation embryo is located in the ampulla of the oviduct.

11. The method of claim 4, wherein the nuclease is a CRISPR-associated (Cas) nuclease.

* * * * *